(12) United States Patent
Bernuetz et al.

(10) Patent No.: US 11,795,469 B2
(45) Date of Patent: Oct. 24, 2023

(54) SCAEVOLA PLANTS WITH RADIALLY SYMMETRICAL FLOWERS

(71) Applicant: Bonza Botanicals Pty Ltd, Yellow Rock (AU)

(72) Inventors: Andrew Bernuetz, Silverdale (AU); Koichi Tomomatsu, Shiga (JP); Kenichi Suzuki, Osaka (JP)

(73) Assignee: Bonza Botanicals Pty Ltd, Yellow Rock (AU)

( * ) Notice: Subject to any disclaimer, the term of this patent is extended or adjusted under 35 U.S.C. 154(b) by 62 days.

(21) Appl. No.: 17/339,079

(22) Filed: Jun. 4, 2021

(65) Prior Publication Data

US 2021/0388368 A1    Dec. 16, 2021

(30) Foreign Application Priority Data

Jun. 4, 2020   (AU) ................................ 2020901841

(51) Int. Cl.
    *C12N 15/82*    (2006.01)
    *C12Q 1/6895*   (2018.01)

(52) U.S. Cl.
    CPC ......... *C12N 15/827* (2013.01); *C12Q 1/6895* (2013.01); *C12Q 2600/13* (2013.01); *C12Q 2600/158* (2013.01)

(58) Field of Classification Search
    CPC ................ C12N 15/827; C12Q 1/6895; C12Q 2600/13; C12Q 2600/158
    See application file for complete search history.

(56) References Cited

PUBLICATIONS

Han (2018 PhD Dissertation, St. John's University New York; 90 total pages) entitled "Duplications and Expression of Cycloidea-Like Genes in Goodeniaceae". (Year: 2018).*
Sweeney (1999 M.S. Thesis, The University of Melbourne; 156 pages in total) entitled "Application of in vitro breeding techniques for the improvement of the Australian native Fanflower, Scaevola" available at https://minerva-access.unimelb.edu.au/items/639c920a-828d-50f8-a3a6-a1415467bbb3. (Year: 1999).*
Chen et al. (2018). "Patterning the Asteraceae capitulum: Duplications and differential expression of the flower symmetry CYC2-like genes," Frontiers in Plant Science, vol. 9, Article 551, pp. 1-14.

(Continued)

*Primary Examiner* — Matthew R Keogh
*Assistant Examiner* — Rebecca Stephens
(74) *Attorney, Agent, or Firm* — MORRISON & FOERSTER LLP

(57) ABSTRACT

The invention provides *Scaevola* plants that produce at least one flower with a floral phenotype characterised by at least one of: a fused, or partially fused, dorsal slit, a radially, or near radially symmetrical, arrangement of petals, and delayed senescence. The phenotype is a result of reduced or eliminated expression or activity of a CYCLOIDEA2 (CYC2) gene or protein, and or presence of a novel allele designated the FUSED allele. The invention further provides plant cells, plant parts, propagules, seeds and tissue cultures of such plants. The invention further provides methods for the productions and selection of such plants, plant cells, plant parts, propagules, seeds and tissue cultures.

16 Claims, 16 Drawing Sheets
(10 of 16 Drawing Sheet(s) Filed in Color)
Specification includes a Sequence Listing.

(56) References Cited

PUBLICATIONS

Citerne et al. (2006). "An apparent reversal in floral symmetry in the legume Cadia is a homeotic transformation," Proceedings of the National Academy of Sciences of the United States of America, 103(32): 12017-12020.

Danisman (2016). "TCP transcription factors at the interface between environmental challenges and the plants growth responses," Frontiers in Plant Sciences, vol. 7, pp. 1-13.

Dong et al. (2018). "Evolution of Darwin's peloric Gloxinia (*Sinningia speciosa*) is caused by a null mutation in a pleiotropic TCP gene," Molecular Biology and Evolution, 35(8): 1901-1915.

Fambrini et al. (2014). "Transposon-dependent induction of Vincent van Gogh's sunflowers: Exceptions revealed," Genesis, 52(4):315-327.

Gardner et al. (2016). "Characterizing Floral Symmetry in the Core Goodeniaceae with Geometric Morphometrics," PLoS ONE, 11(5): e0154736, 22 pages.

Zhang et al. (2013). "Divergent genetic mechanisms underlie reversals to radial floral symmetry from diverse zygomorphic flowered ancestors," Front. Plant Sci. 4:302, 13 pages.

\* cited by examiner

Figure 2
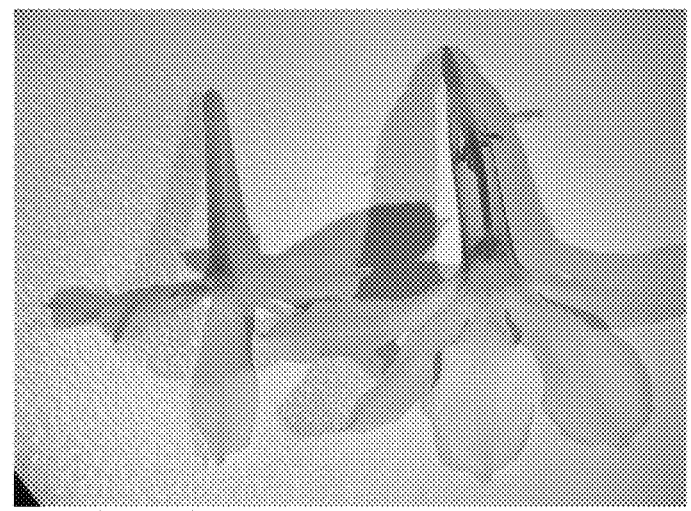
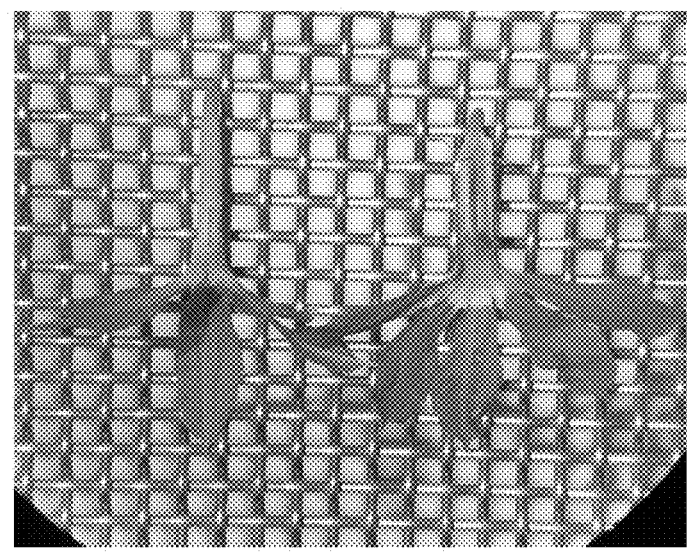

Figure 3
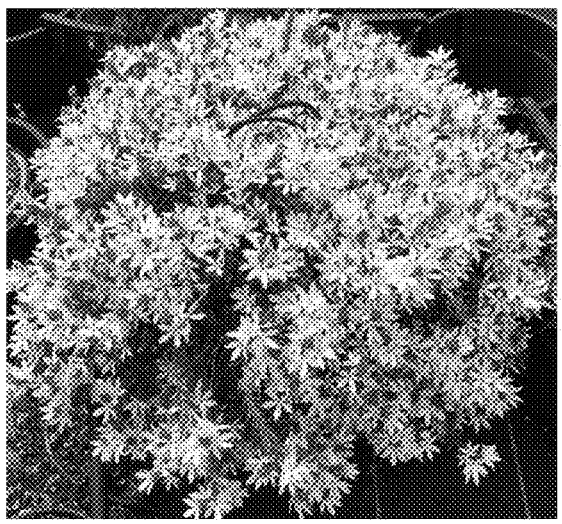
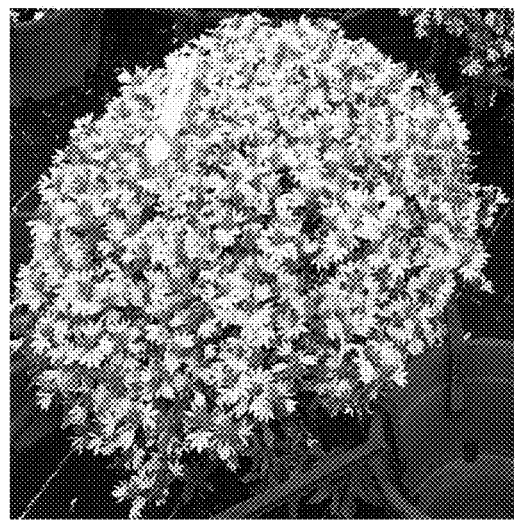

Figure 4
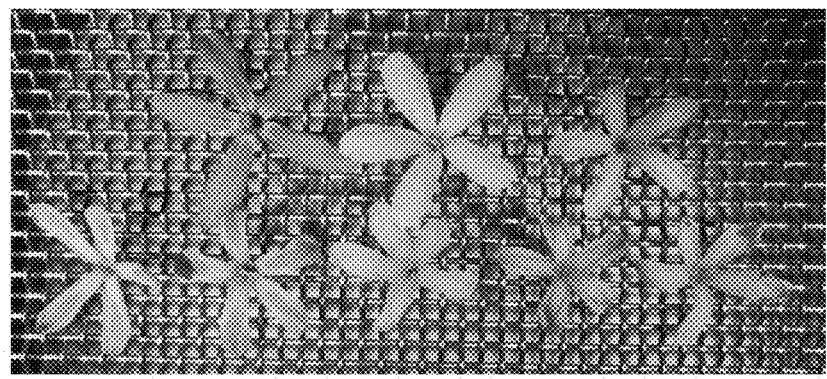
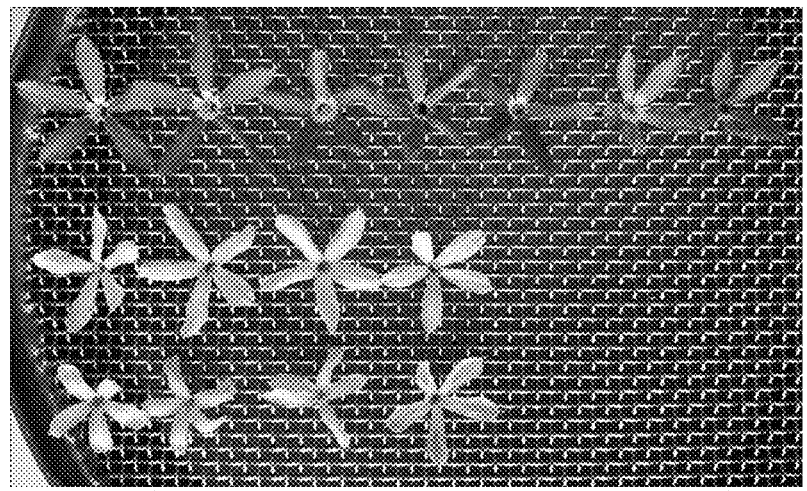

Figure 14

```
SaeCYC2    --------------------PDLFFGHEKDGFYFSNNSHLHHHLYCHNPFVSGGCFSPQV    40
StaCYC2    MYSSNPFPQLTSSIHVCPPSPDLFFGHEKDGFYFGNNSQLHHHLYFHNPFVSGGCFSPQV    60
SseCYC2    MYSSNPFPQLTSSIHVCPPSPDLFFGHEKDGFYFGNNSQLHHHLYFHNPFVSGGCFSPQV    60
                               ************.***:****** ***************
           MOTIF 4

SaeCYC2    MENVTTIDQDFMRQQQ---QQLTKEEGLQCCTDDHAHLLDSVITPLSKKKVDVKKDRHRKI    98
StaCYC2    MENVTTIDQDFMRQQQQQQQLTKEAGLQCCADDHAHLLDSVISPFSKKKVDVKKDRHRKI   120
SseCYC2    MENVTTIDQDFMRQQQQQQQLTKEAGLQCCADDHAHLLDSVISPFSKKKVDVKKDRHRKI   120
           ****************   ****** *****:**********:*:**************
                                                                   MOTIF 1

SaeCYC2    FTAQGPRDRRVRLSLDIARKFFSLQDLLGFDKASKTLDWLFTKSKTAIKELVEEKKQSSS   158
StaCYC2    FTAQGPRDRRVRLSLDIARKLFSLQDLLGFDKASKTLDWLFTKSKTAIKELVEEKKQSSS   180
SseCYC2    FTAQGPRDRRVRLSLDIARKLFSLQDLLGFDKASKTLDWLFTKSKTAIKELVEEKKQSSS   180
           ********************:***************************************
           MOTIF 1 continued SaeCYC2    STVTDQCKMVSMEIFKEGDEDEGEKTSVLKRVKGKRKKMTQKHKARYHVNLARDQLRVEA   218
StaCYC2    STVTDQCKMVSMEIFKEGDEDEGEKTSVLKRVKGKRKKMTQKHKARNHVNLARDQLRAEA   240
SseCYC2    STVTDQCKMVSMEIFKEGDEDEGEKTSVLKRVKGKRKKMTQKHKARNHVNLARDQLRAEA   240
           *********************************************.**********.**
                                                                   MOTIF 2

SaeCYC2    RARARERTREKLRIKKLDDLCKRVPDSYCHVSPTLILQSSCWSQTESQSNIKEIVGESNM   278
StaCYC2    RARARERTREKLRIKKLDDLCKRVPDNYCHVSPTLILQSGCWSQTESQSNIKEIVGESNM   300
SseCYC2    RARARERTREKLRIKKLDDLCKRVPDNYCHVSPTLILQSGCWSQTESQSNIKEIVGESNM   300
           *************************.************.********************
           MOTIF 2 continued SaeCYC2    NQKFSKPSSMLYSYQHNLVVSKDPISESKYTRSPKFS   315
StaCYC2    NQKFSKPSSMLYSYQHNLVVSKEPISESKYTRLPIFS   337
SseCYC2    NQKFSKPSSMLYSYQHNLVVSKEPISESKYTRLPIFS   337
           *********************:********** ***
```

Figure 15

|         | SaeCYC2 | StaCYC2 | SseCYC2 |
|---------|---------|---------|---------|
| SaeCYC2 | 100.00  | 95.24   | 95.24   |
| StaCYC2 | 95.24   | 100.00  | 100.00  |
| SseCYC2 | 95.24   | 100.00  | 100.00  |

SEQUENCE LISTING

<160> NUMBER OF SEQ ID NOS: 38

<210> SEQ ID NO 1
<211> LENGTH: 315
<212> TYPE: PRT
<213> ORGANISM: Scaevola aemula

<400> SEQUENCE: 1

```
Pro Asp Leu Phe Phe Gly His Glu Lys Asp Gly Phe Tyr Phe Ser Asn
1               5                   10                  15

Asn Ser His Leu His His His Leu Tyr Cys Asn Pro Phe Val Ser
            20                  25                  30
```

-continued

Gly Gly Cys Phe Ser Pro Gln Val Met Glu Asn Val Thr Thr Ile Asp
            35                  40                  45

Gln Asp Phe Met Arg Gln Gln Gln Gln Leu Thr Lys Glu Glu Gly
 50                  55                  60

Leu Gln Cys Cys Thr Asp Asp His Ala His Leu Leu Asp Ser Val Ile
 65                  70                  75                  80

Thr Pro Leu Ser Lys Lys Val Asp Val Lys Lys Asp Arg His Arg
                85                  90                  95

Lys Ile Phe Thr Ala Gln Gly Pro Arg Asp Arg Val Arg Leu Ser
                100                 105                 110

Leu Asp Ile Ala Arg Lys Phe Phe Ser Leu Gln Asp Leu Leu Gly Phe
                115                 120                 125

Asp Lys Ala Ser Lys Thr Leu Asp Trp Leu Phe Thr Lys Ser Lys Thr
130                 135                 140

Ala Ile Lys Glu Leu Val Glu Glu Lys Lys Gln Ser Ser Ser Ser Thr
145                 150                 155                 160

Val Thr Asp Gln Cys Lys Met Val Ser Met Glu Ile Phe Lys Glu Gly
                165                 170                 175

Asp Glu Asp Glu Gly Glu Lys Thr Ser Val Leu Lys Arg Val Lys Gly
                180                 185                 190

Lys Arg Lys Lys Met Thr Gln Lys His Lys Ala Arg Tyr His Val Asn
                195                 200                 205

Leu Ala Arg Asp Gln Leu Arg Val Glu Ala Arg Ala Arg Ala Arg Glu
                210                 215                 220

Arg Thr Arg Glu Lys Leu Arg Ile Lys Lys Leu Asp Asp Leu Cys Lys
225                 230                 235                 240

Arg Val Pro Asp Ser Tyr Cys His Val Ser Pro Thr Leu Ile Leu Gln
                245                 250                 255

Ser Ser Cys Trp Ser Gln Thr Glu Ser Gln Ser Asn Ile Lys Glu Ile
                260                 265                 270

Val Gly Glu Ser Asn Met Asn Gln Lys Phe Ser Lys Pro Ser Ser Met
                275                 280                 285

Leu Tyr Ser Tyr Gln His Asn Leu Val Val Ser Lys Asp Pro Ile Ser
                290                 295                 300

Glu Ser Lys Tyr Thr Arg Ser Pro Lys Phe Ser
305                 310                 315

<210> SEQ ID NO 2
<211> LENGTH: 337
<212> TYPE: PRT
<213> ORGANISM: Scaevola taccada

<400> SEQUENCE: 2

Met Tyr Ser Ser Asn Pro Phe Pro Gln Leu Thr Ser Ser Ile His Val
1               5                   10                  15

Cys Pro Pro Ser Pro Asp Leu Phe Phe Gly His Glu Lys Asp Gly Phe
                20                  25                  30

Tyr Phe Gly Asn Asn Ser Gln Leu His His Leu Tyr Phe His Asn
            35                  40                  45

Pro Phe Val Ser Gly Gly Cys Phe Ser Pro Gln Val Met Glu Asn Val
        50                  55                  60

Thr Thr Ile Asp Gln Asp Phe Met Arg Gln Gln Gln Gln Gln Gln
65                  70                  75                  80

Leu Thr Lys Glu Ala Gly Leu Gln Cys Cys Ala Asp Asp His Ala His

```
                85                  90                  95
Leu Leu Asp Ser Val Ile Ser Pro Phe Ser Lys Lys Val Asp Val
            100                 105                 110

Lys Lys Asp Arg His Arg Lys Ile Phe Thr Ala Gln Gly Pro Arg Asp
            115                 120                 125

Arg Arg Val Arg Leu Ser Leu Asp Ile Ala Arg Lys Leu Phe Ser Leu
130                 135                 140

Gln Asp Leu Leu Gly Phe Asp Lys Ala Ser Lys Thr Leu Asp Trp Leu
145                 150                 155                 160

Phe Thr Lys Ser Lys Thr Ala Ile Lys Glu Leu Val Glu Lys Lys
                165                 170                 175

Gln Ser Ser Ser Ser Thr Val Thr Asp Gln Cys Lys Met Val Ser Met
                180                 185                 190

Glu Ile Phe Lys Glu Gly Asp Glu Asp Glu Gly Glu Lys Thr Ser Val
                195                 200                 205

Leu Lys Arg Val Lys Gly Lys Arg Lys Lys Met Thr Gln Lys His Lys
            210                 215                 220

Ala Arg Asn His Val Asn Leu Ala Arg Asp Gln Leu Arg Ala Glu Ala
225                 230                 235                 240

Arg Ala Arg Ala Arg Glu Arg Thr Arg Glu Lys Leu Arg Ile Lys Lys
                245                 250                 255

Leu Asp Asp Leu Cys Lys Arg Val Pro Asp Asn Tyr Cys His Val Ser
            260                 265                 270

Pro Thr Leu Ile Leu Gln Ser Gly Cys Trp Ser Gln Thr Glu Ser Gln
            275                 280                 285

Ser Asn Ile Lys Glu Ile Val Gly Glu Ser Asn Met Asn Gln Lys Phe
        290                 295                 300

Ser Lys Pro Ser Ser Met Leu Tyr Ser Tyr Gln His Asn Leu Val Val
305                 310                 315                 320

Ser Lys Glu Pro Ile Ser Glu Ser Lys Tyr Thr Arg Leu Pro Ile Phe
                325                 330                 335

Ser

<210> SEQ ID NO 3
<211> LENGTH: 337
<212> TYPE: PRT
<213> ORGANISM: Scaevola sericea

<400> SEQUENCE: 3

Met Tyr Ser Ser Asn Pro Phe Pro Gln Leu Thr Ser Ser Ile His Val
1               5                   10                  15

Cys Pro Pro Ser Pro Asp Leu Phe Phe Gly His Glu Lys Asp Gly Phe
                20                  25                  30

Tyr Phe Gly Asn Asn Ser Gln Leu His His His Leu Tyr Phe His Asn
            35                  40                  45

Pro Phe Val Ser Gly Gly Cys Phe Ser Pro Gln Val Met Glu Asn Val
        50                  55                  60

Thr Thr Ile Asp Gln Asp Phe Met Arg Gln Gln Gln Gln Gln Gln Gln
65                  70                  75                  80

Leu Thr Lys Glu Ala Gly Leu Gln Cys Cys Ala Asp Asp His Ala His
                85                  90                  95

Leu Leu Asp Ser Val Ile Ser Pro Phe Ser Lys Lys Val Asp Val
            100                 105                 110

Lys Lys Asp Arg His Arg Lys Ile Phe Thr Ala Gln Gly Pro Arg Asp
```

```
                115                 120                 125
Arg Arg Val Arg Leu Ser Leu Asp Ile Ala Arg Lys Leu Phe Ser Leu
        130                 135                 140

Gln Asp Leu Leu Gly Phe Asp Lys Ala Ser Lys Thr Leu Asp Trp Leu
145                 150                 155                 160

Phe Thr Lys Ser Lys Thr Ala Ile Lys Glu Leu Val Glu Glu Lys Lys
                165                 170                 175

Gln Ser Ser Ser Thr Val Thr Asp Gln Cys Lys Met Val Ser Met
            180                 185                 190

Glu Ile Phe Lys Glu Gly Asp Glu Asp Glu Gly Glu Lys Thr Ser Val
        195                 200                 205

Leu Lys Arg Val Lys Gly Lys Arg Lys Lys Met Thr Gln Lys His Lys
        210                 215                 220

Ala Arg Asn His Val Asn Leu Ala Arg Asp Gln Leu Arg Ala Glu Ala
225                 230                 235                 240

Arg Ala Arg Ala Arg Glu Arg Thr Arg Glu Lys Leu Arg Ile Lys Lys
                245                 250                 255

Leu Asp Asp Leu Cys Lys Arg Val Pro Asp Asn Tyr Cys His Val Ser
            260                 265                 270

Pro Thr Leu Ile Leu Gln Ser Gly Cys Trp Ser Gln Thr Glu Ser Gln
        275                 280                 285

Ser Asn Ile Lys Glu Ile Val Gly Glu Ser Asn Met Asn Gln Lys Phe
        290                 295                 300

Ser Lys Pro Ser Ser Met Leu Tyr Ser Tyr Gln His Asn Leu Val Val
305                 310                 315                 320

Ser Lys Glu Pro Ile Ser Glu Ser Lys Tyr Thr Arg Leu Pro Ile Phe
                325                 330                 335

Ser

<210> SEQ ID NO 4
<211> LENGTH: 956
<212> TYPE: DNA
<213> ORGANISM: Scaevola aemula

<400> SEQUENCE: 4
ccagatctct tctttggcca tgaaaaagat ggttttact tcagcaacaa tagccacctc      60
caccaccatc tttactgcca caacccttt gtctctggtg ggtgtttctc tcctcaggtt     120
atggagaatg ttactacaat agatcaagat ttcatgaggc agcagcagca gcagctcact    180
aaagaagaag gtttacagtg ttgtaccgat gatcatgctc atttgttaga ttcagtcatt    240
accccgctta gcaagaaaaa agttgatgtg aagaaagatc gtcatagaaa gatcttcaca    300
gctcaaggcc ctagggatcg gagggtgaga ttgtcgttgg atatcgcaag aaagttcttc    360
agtcttcagg acttgctagg gtttgacaaa gcaagcaaaa cccttgattg cttttcacc    420 aagtccaaga cagcaattaa ggagcttgtt gaagaaaaga gcaaagctc atcttccact    480 gttactgatc aatgtaaaat ggtctccatg gaaatcttca aggaaggaga tgaagatgaa    540
ggggaaaaga cgtcagtgct caagcgtgtt aaaggcaaaa ggaagaaaat gacccagaag    600
cacaaagctc gataccatgt taatcttgca agagatcagt taagggtaga ggcaagagca    660
agagctaggg aaagaacaag agaaaagttg cggattaaaa agcttgatga tctatgcaag    720
agagttccag atagttactg tcacgtaagc ccaaccttaa tactccagtc aagctgttgg    780
agtcaaaccg aatcacaaag taatatcaaa gaaatagttg gggaatcaaa tatgaaccag    840
```

```
aaattctcaa aaccatcttc aatgttgtat agctaccaac acaaccttgt tgtatcaaaa    900
gatccaatct ccgaaagcaa gtacactcgt tcccctaaat tctcatgatt cttgag        956
```

<210> SEQ ID NO 5
<211> LENGTH: 948
<212> TYPE: DNA
<213> ORGANISM: Scaevola aemula

<400> SEQUENCE: 5

```
ccagatctct tctttggcca tgaaaaagat ggttttact tcagcaacaa tagccacctc     60
caccaccatc tttactgcca caacccttt gtctctggtg ggtgtttctc tcctcaggtt    120
atggagaatg ttactacaat agatcaagat ttcatgaggc agcagcagca gcagctcact   180
aaagaagaag gtttacagtg ttgtaccgat gatcatgctc atttgttaga ttcagtcatt   240
accccgctta gcaagaaaaa agttgatgtg aagaaagatc gtcatagaaa gatcttcaca   300
gctcaaggcc ctagggatcg gagggtgaga ttgtcgttgg atatcgcaag aaagttcttc   360
agtcttcagg acttgctagg gtttgacaaa gcaagcaaaa cccttgattg cttttcacc    420 aagtccaaga cagcaattaa ggagcttgtt gaagaaaaga gcaaagctc atcttccact    480 gttactgatc aatgtaaaat ggtctccatg gaaatcttca aggaaggaga tgaagatgaa   540
ggggaaaaga cgtcagtgct caagcgtgtt aaaggcaaaa ggaagaaaat gacccagaag   600
cacaaagctc gataccatgt taatcttgca agagatcagt taagggtaga ggcaagagca   660
agagctaggg aaagaacaag agaaaagttg cggattaaaa agcttgatga tctatgcaag   720
agagttccag atagttactg tcacgtaagc ccaaccttaa tactccagtc aagctgttgg   780
agtcaaaccg aatcacaaag taatatcaaa gaatagttg gggaatcaaa tatgaaccag   840
aaattctcaa aaccatcttc aatgttgtat agctaccaac acaaccttgt tgtatcaaaa   900
gatccaatct ccgaaagcaa gtacactcgt tcccctaaat tctcatga                948
```

<210> SEQ ID NO 6
<211> LENGTH: 1226
<212> TYPE: DNA
<213> ORGANISM: Scaevola taccada

<400> SEQUENCE: 6

```
atgtattctt caaacccatt tccacagctc acctcatcca tccatgtctg ccctccttct    60
ccagatctct tctttggtca tgaaaaagat ggttttact tcggtaacaa tagccagctc   120
caccaccatc tttacttcca caacccttt gtctctggtg ttgtttctc tcctcaggtt    180 atggagaatg ttactacaat agatcaagat ttcatgaggc agcagcagca gcagcagcag   240
ctcactaaag aagcaggttt acaatgctgt gctgatgatc atgctcattt gttagattca   300
gtaatttccc cgtttagcaa gaaaaagtt gatgtgaaga aagatcggca tagaaagatc   360
ttcacagctc aaggcctag gatcggagg gtgagattgt cgttagatat cgcaagaaag   420
ttattcagtc ttcaggactt gctagggttt gataaagcaa gcaaaccct tgattggctt   480 ttcaccaagt ccaagacagc aattaaggag cttgtagagg aaaagaagca agctcatct   540 tccactgtta ctgatcaatg taaaatggtt tccatggaaa tcttcaagga aggagatgaa   600
gatgaagggg aaaagacgtc agtgctcaag cgtgttaaag gcaaaaggaa gaaatgacc   660 cagaagcaca agctcgaaa ccatgttaac cttgcaagag atcagttaag ggcagaggca   720
agagccagag ctagggaaag aacaagagaa agttgcgca ttaaaaagct tgatgatcta   780
tgcaagagag ttcctgataa ttactgtcac gtaagcccaa ccttaatact ccagtcaggc   840
```

-continued

```
tgttggagtc aaaccgaatc acaaagtaat atcaaagaaa tagttgggga atcaaatatg      900
aaccagaaat tctcaaaacc atcttcaatg ttgtatagct accaacacaa ccttgttgta      960
tcaaaagaac caatctccga aagcaagtac actcgtttgc ctatattctc atgattcttc     1020
ggcagcaggg tgatgcgtgt aacaagttag atccacaaga ggtaccttat taaatctctc     1080
ttaatttcac tcacacacat gaagttgcaa gatgatttca tttctgtatg ttcattttgg     1140
tttacagtta gctatatata caaaagaaaa ggcagcagac aatcatgtgc aatatattta     1200
tccttcagcc agtcgccaga tctagt                                          1226
```

<210> SEQ ID NO 7
<211> LENGTH: 959
<212> TYPE: DNA
<213> ORGANISM: Scaevola aemula

<400> SEQUENCE: 7

```
ccagatctct tctttggcca tgaaaaagat ggttttaat tcagcaacaa tagccacctc       60
caccaccatc tttactgcca caaccctttt gtctctggtg ggtgtttctc tcctcaggtt      120
atggagaatg ttactacaat agatcaagat ttcatgaggc agcagcagca gcagcagctc      180
actaaagaag aaggtttaca gtgttgtacc gatgatcatg ctcatttgtt agattcagtc      240 attacccgc ttagcaagaa aaagttgat gtgaagaaag atcgtcatag aaagatcttc        300
acagctcaag gccctaggga tcggagggtg agattgtcgt tggatatcgc aagaaagttc      360
ttcagtcttc aggacttgct agggtttgac aaagcaagca aaacccttga ttggcttttc      420
accaagtcca agacagcaat taaggagctt gttgaagaaa agaagcaaag ctcatcttcc      480
actgttactg atcaatgtaa aatggtctcc atggaaatct tcaaggaagg agatgaagat      540 gaagggaaa agacgtcagt gctcaagcgt gttaaaggca aaaggaagaa aatgacccag       600
aaacacaaag ctcgatacca tgttaatctt gcaagagatc agttaagggc agaggcaaga      660
gcaagagcta gggaaagaac aagagaaaag ttgcggatta aaaagcttga tgatctatgc      720
aagagagttc cagatagtta ctgtcacgta agcccaacct taatactcca gtcaagctgt      780
tggagtcaaa ccgaatcaca aagtaatatc aaagaaatag ttggggaatc aaatatgaac      840
cagaaattct caaaccatc ttcaatgttg tatagctacc aacacaacct tgttgtatca      900
aaagatccaa tctccgaaag caagtacact cgttccccta aattctcatg attcttgag       959
```

<210> SEQ ID NO 8
<211> LENGTH: 951
<212> TYPE: DNA
<213> ORGANISM: Scaevola aemula

<400> SEQUENCE: 8

```
ccagatctct tctttggcca tgaaaaagat ggttttaat tcagcaacaa tagccacctc       60
caccaccatc tttactgcca caaccctttt gtctctggtg ggtgtttctc tcctcaggtt      120
atggagaatg ttactacaat agatcaagat ttcatgaggc agcagcagca gcagcagctc      180
actaaagaag aaggtttaca gtgttgtacc gatgatcatg ctcatttgtt agattcagtc      240 attacccgc ttagcaagaa aaagttgat gtgaagaaag atcgtcatag aaagatcttc        300
acagctcaag gccctaggga tcggagggtg agattgtcgt tggatatcgc aagaaagttc      360
ttcagtcttc aggacttgct agggtttgac aaagcaagca aaacccttga ttggcttttc      420
accaagtcca agacagcaat taaggagctt gttgaagaaa agaagcaaag ctcatcttcc      480
```

```
actgttactg atcaatgtaa aatggtctcc atggaaatct tcaaggaagg agatgaagat    540 gaagggaaa agacgtcagt gctcaagcgt gttaaaggca aaaggaagaa aatgacccag    600
aaacacaaag ctcgatacca tgttaatctt gcaagagatc agttaagggc agaggcaaga    660
gcaagagcta gggaaagaac aagagaaaag ttgcggatta aaaagcttga tgatctatgc    720
aagagagttc cagatagtta ctgtcacgta agcccaacct taatactcca gtcaagctgt    780
tggagtcaaa ccgaatcaca agtaatatc aaagaaatag ttggggaatc aaatatgaac    840
cagaaattct caaaaccatc ttcaatgttg tatagctacc aacacaacct tgttgtatca    900
aaagatccaa tctccgaaag caagtacact cgttccccta aattctcatg a             951

<210> SEQ ID NO 9
<211> LENGTH: 62
<212> TYPE: PRT
<213> ORGANISM: Unknown
<220> FEATURE:
<223> OTHER INFORMATION: Asterales sp.
<220> FEATURE:
<221> NAME/KEY: VARIANT
<222> LOCATION: (1)..(2)
<223> OTHER INFORMATION: Xaa can be any naturally occurring amino acid
<220> FEATURE:
<221> NAME/KEY: VARIANT
<222> LOCATION: (4)..(6)
<223> OTHER INFORMATION: Xaa can be any naturally occurring amino acid
<220> FEATURE:
<221> NAME/KEY: VARIANT
<222> LOCATION: (9)..(9)
<223> OTHER INFORMATION: Xaa can be any naturally occurring amino acid
<220> FEATURE:
<221> NAME/KEY: VARIANT
<222> LOCATION: (11)..(12)
<223> OTHER INFORMATION: Xaa can be any naturally occurring amino acid
<220> FEATURE:
<221> NAME/KEY: VARIANT
<222> LOCATION: (14)..(14)
<223> OTHER INFORMATION: Xaa can be any naturally occurring amino acid
<220> FEATURE:
<221> NAME/KEY: VARIANT
<222> LOCATION: (16)..(16)
<223> OTHER INFORMATION: Xaa can be any naturally occurring amino acid
<220> FEATURE:
<221> NAME/KEY: VARIANT
<222> LOCATION: (21)..(21)
<223> OTHER INFORMATION: Xaa can be any naturally occurring amino acid
<220> FEATURE:
<221> NAME/KEY: VARIANT
<222> LOCATION: (23)..(28)
<223> OTHER INFORMATION: Xaa can be any naturally occurring amino acid
<220> FEATURE:
<221> NAME/KEY: VARIANT
<222> LOCATION: (31)..(31)
<223> OTHER INFORMATION: Xaa can be any naturally occurring amino acid
<220> FEATURE:
<221> NAME/KEY: VARIANT
<222> LOCATION: (34)..(35)
<223> OTHER INFORMATION: Xaa can be any naturally occurring amino acid
<220> FEATURE:
<221> NAME/KEY: VARIANT
<222> LOCATION: (37)..(38)
<223> OTHER INFORMATION: Xaa can be any naturally occurring amino acid
<220> FEATURE:
<221> NAME/KEY: VARIANT
<222> LOCATION: (40)..(41)
<223> OTHER INFORMATION: Xaa can be any naturally occurring amino acid
<220> FEATURE:
<221> NAME/KEY: VARIANT
<222> LOCATION: (43)..(43)
<223> OTHER INFORMATION: Xaa can be any naturally occurring amino acid
<220> FEATURE:
<221> NAME/KEY: VARIANT
<222> LOCATION: (45)..(46)
<223> OTHER INFORMATION: Xaa can be any naturally occurring amino acid
```

```
<220> FEATURE:
<221> NAME/KEY: VARIANT
<222> LOCATION: (49)..(55)
<223> OTHER INFORMATION: Xaa can be any naturally occurring amino acid
<220> FEATURE:
<221> NAME/KEY: VARIANT
<222> LOCATION: (57)..(58)
<223> OTHER INFORMATION: Xaa can be any naturally occurring amino acid
<220> FEATURE:
<221> NAME/KEY: VARIANT
<222> LOCATION: (60)..(62)
<223> OTHER INFORMATION: Xaa can be any naturally occurring amino acid

<400> SEQUENCE: 9

Xaa Xaa Asp Xaa Xaa Xaa Lys Ile Xaa Thr Xaa Xaa Gly Xaa Arg Xaa
1               5                   10                  15

Arg Arg Val Arg Xaa Ser Xaa Xaa Xaa Xaa Xaa Xaa Phe Phe Xaa Leu
            20                  25                  30

Gln Xaa Xaa Leu Xaa Xaa Asp Xaa Xaa Ser Xaa Thr Xaa Xaa Trp Leu
        35                  40                  45

Xaa Xaa Xaa Xaa Xaa Xaa Xaa Ile Xaa Xaa Leu Xaa Xaa Xaa
    50                  55                  60

<210> SEQ ID NO 10
<211> LENGTH: 62
<212> TYPE: PRT
<213> ORGANISM: Unknown
<220> FEATURE:
<223> OTHER INFORMATION: Scaevola sp.
<220> FEATURE:
<221> NAME/KEY: VARIANT
<222> LOCATION: (29)..(29)
<223> OTHER INFORMATION: Xaa can be any naturally occurring amino acid

<400> SEQUENCE: 10

Lys Lys Asp Arg His Arg Lys Ile Phe Thr Ala Gln Gly Pro Arg Asp
1               5                   10                  15

Arg Arg Val Arg Leu Ser Leu Asp Ile Ala Arg Lys Xaa Phe Ser Leu
            20                  25                  30

Gln Asp Leu Leu Gly Phe Asp Lys Ala Ser Lys Thr Leu Asp Trp Leu
        35                  40                  45

Phe Thr Lys Ser Lys Thr Ala Ile Lys Glu Leu Val Glu Glu
    50                  55                  60

<210> SEQ ID NO 11
<211> LENGTH: 62
<212> TYPE: PRT
<213> ORGANISM: Unknown
<220> FEATURE:
<223> OTHER INFORMATION: Scaevola sp.
<220> FEATURE:
<221> NAME/KEY: VARIANT
<222> LOCATION: (29)..(29)
<223> OTHER INFORMATION: Xaa is either Phe or Leu

<400> SEQUENCE: 11

Lys Lys Asp Arg His Arg Lys Ile Phe Thr Ala Gln Gly Pro Arg Asp
1               5                   10                  15

Arg Arg Val Arg Leu Ser Leu Asp Ile Ala Arg Lys Xaa Phe Ser Leu
            20                  25                  30

Gln Asp Leu Leu Gly Phe Asp Lys Ala Ser Lys Thr Leu Asp Trp Leu
        35                  40                  45

Phe Thr Lys Ser Lys Thr Ala Ile Lys Glu Leu Val Glu Glu
    50                  55                  60
```

<210> SEQ ID NO 12
<211> LENGTH: 62
<212> TYPE: PRT
<213> ORGANISM: Scaevola aemula

<400> SEQUENCE: 12

Lys Lys Asp Arg His Arg Lys Ile Phe Thr Ala Gln Gly Pro Arg Asp
1               5                   10                  15

Arg Arg Val Arg Leu Ser Leu Asp Ile Ala Arg Lys Phe Phe Ser Leu
            20                  25                  30

Gln Asp Leu Leu Gly Phe Asp Lys Ala Ser Lys Thr Leu Asp Trp Leu
        35                  40                  45

Phe Thr Lys Ser Lys Thr Ala Ile Lys Glu Leu Val Glu Glu
    50                  55                  60

<210> SEQ ID NO 13
<211> LENGTH: 62
<212> TYPE: PRT
<213> ORGANISM: Scaevola taccada

<400> SEQUENCE: 13

Lys Lys Asp Arg His Arg Lys Ile Phe Thr Ala Gln Gly Pro Arg Asp
1               5                   10                  15

Arg Arg Val Arg Leu Ser Leu Asp Ile Ala Arg Lys Phe Phe Ser Leu
            20                  25                  30

Gln Asp Leu Leu Gly Phe Asp Lys Ala Ser Lys Thr Leu Asp Trp Leu
        35                  40                  45

Phe Thr Lys Ser Lys Thr Ala Ile Lys Glu Leu Val Glu Glu
    50                  55                  60

<210> SEQ ID NO 14
<211> LENGTH: 62
<212> TYPE: PRT
<213> ORGANISM: Scaevola sericea

<400> SEQUENCE: 14

Lys Lys Asp Arg His Arg Lys Ile Phe Thr Ala Gln Gly Pro Arg Asp
1               5                   10                  15

Arg Arg Val Arg Leu Ser Leu Asp Ile Ala Arg Lys Phe Phe Ser Leu
            20                  25                  30

Gln Asp Leu Leu Gly Phe Asp Lys Ala Ser Lys Thr Leu Asp Trp Leu
        35                  40                  45

Phe Thr Lys Ser Lys Thr Ala Ile Lys Glu Leu Val Glu Glu
    50                  55                  60

<210> SEQ ID NO 15
<211> LENGTH: 23
<212> TYPE: PRT
<213> ORGANISM: Unknown
<220> FEATURE:
<223> OTHER INFORMATION: Scaevola sp.
<220> FEATURE:
<221> NAME/KEY: VARIANT
<222> LOCATION: (5)..(5)
<223> OTHER INFORMATION: Xaa can be any naturally occurring amino acid

<400> SEQUENCE: 15

Asp Gln Leu Arg Xaa Glu Ala Arg Ala Arg Ala Arg Glu Arg Thr Arg
1               5                   10                  15

Glu Lys Leu Arg Ile Lys Lys
            20

```
<210> SEQ ID NO 16
<211> LENGTH: 23
<212> TYPE: PRT
<213> ORGANISM: Unknown
<220> FEATURE:
<223> OTHER INFORMATION: Scaevola sp.
<220> FEATURE:
<221> NAME/KEY: VARIANT
<222> LOCATION: (5)..(5)
<223> OTHER INFORMATION: Xaa is either Val or Ala

<400> SEQUENCE: 16

Asp Gln Leu Arg Xaa Glu Ala Arg Ala Arg Ala Arg Glu Arg Thr Arg
1               5                   10                  15

Glu Lys Leu Arg Ile Lys Lys
            20

<210> SEQ ID NO 17
<211> LENGTH: 23
<212> TYPE: PRT
<213> ORGANISM: Scaevola aemula

<400> SEQUENCE: 17

Asp Gln Leu Arg Val Glu Ala Arg Ala Arg Ala Arg Glu Arg Thr Arg
1               5                   10                  15

Glu Lys Leu Arg Ile Lys Lys
            20

<210> SEQ ID NO 18
<211> LENGTH: 23
<212> TYPE: PRT
<213> ORGANISM: Scaevola tacada

<400> SEQUENCE: 18

Asp Gln Leu Arg Ala Glu Ala Arg Ala Arg Ala Arg Glu Arg Thr Arg
1               5                   10                  15

Glu Lys Leu Arg Ile Lys Lys
            20

<210> SEQ ID NO 19
<211> LENGTH: 23
<212> TYPE: PRT
<213> ORGANISM: Scaevola sericea

<400> SEQUENCE: 19

Asp Gln Leu Arg Ala Glu Ala Arg Ala Arg Ala Arg Glu Arg Thr Arg
1               5                   10                  15

Glu Lys Leu Arg Ile Lys Lys
            20

<210> SEQ ID NO 20
<211> LENGTH: 12
<212> TYPE: PRT
<213> ORGANISM: Unknown
<220> FEATURE:
<223> OTHER INFORMATION: Scaevola sp.

<400> SEQUENCE: 20

Met Tyr Ser Ser Asn Pro Phe Pro Gln Leu Thr Ser
1               5                   10

<210> SEQ ID NO 21
<211> LENGTH: 12
```

-continued

```
<212> TYPE: PRT
<213> ORGANISM: Scaevola tacada

<400> SEQUENCE: 21

Met Tyr Ser Ser Asn Pro Phe Pro Gln Leu Thr Ser
1               5                  10

<210> SEQ ID NO 22
<211> LENGTH: 12
<212> TYPE: PRT
<213> ORGANISM: Scaevola sericea

<400> SEQUENCE: 22

Met Tyr Ser Ser Asn Pro Phe Pro Gln Leu Thr Ser
1               5                  10

<210> SEQ ID NO 23
<211> LENGTH: 1008
<212> TYPE: DNA
<213> ORGANISM: Scaevola aemula

<400> SEQUENCE: 23
atgttttctt caaacccatt ttcacagctt acctcatcca tccatgtctg ccctccttct     60
ccagatctct tctttggcca tgaaaaagat ggttttact tcagcaacaa tagccacctc    120
caccaccatc tttactgcca caacccttttt gtctctggtg ggtgtttctc tcctcaggtt   180
atggagaatg ttactacaat agatcaagat ttcatgaggc agcagcagca gcagctcact   240
aaagaagaag gttacagtg ttgtaccgat gatcatgctc atttgttaga ttcagtcatt    300
accccgctta gcaagaaaaa agttgatgtg aagaaagatc gtcatagaaa gatcttcaca   360
gctcaaggcc ctagggatcg gagggtgaga ttgtcgttgg atatcgcaag aaagttcttc   420
agtcttcagg acttgctagg gtttgacaaa gcaagcaaaa cccttgattg cttttcacc    480 aagtccaaga cagcaattaa ggagcttgtt gaagaaaaga gcaaagctc atcttccact    540 gttactgatc aatgtaaaat ggtctccatg gaaatcttca aggaaggaga tgaagatgaa   600
ggggaaaaga cgtcagtgct caagcgtgtt aaaggcaaaa ggaagaaaat gacccagaag   660
cacaaagctc gataccatgt taatcttgca agagatcagt taagggtaga ggcaagagca   720
agagctaggg aaagaacaag agaaaagttg cggattaaaa agcttgatga tctatgcaag   780
agagttccag atagttactg tcacgtaagc ccaaccttaa tactccagtc aagctgttgg   840
agtcaaaccg aatcacaaag taatatcaaa gaaatagttg gggaatcaaa tatgaaccag   900
aaattctcaa aaccatcttc aatgttgtat agctaccaac acaaccttgt tgtatcaaaa   960
gatccaatct ccgaaagcaa gtacactcgt tcccctaaat tctcatga             1008

<210> SEQ ID NO 24
<211> LENGTH: 1011
<212> TYPE: DNA
<213> ORGANISM: Scaevola aemula

<400> SEQUENCE: 24
atgttttctt caaacccatt ttcacagctt acctcatcca tccatgtctg ccctccttct     60
ccagatctct tctttggcca tgaaaaagat ggttttaat tcagcaacaa tagccacctc   120
caccaccatc tttactgcca caacccttttt gtctctggtg ggtgtttctc tcctcaggtt   180
atggagaatg ttactacaat agatcaagat ttcatgaggc agcagcagca gcagcagctc   240
actaaagaag aaggtttaca gtgttgtacc gatgatcatg ctcatttgtt agattcagtc   300
```

```
attaccccgc ttagcaagaa aaaagttgat gtgaagaaag atcgtcatag aaagatcttc      360
acagctcaag gccctaggga tcggagggtg agattgtcgt tggatatcgc aagaaagttc      420
ttcagtcttc aggacttgct agggtttgac aaagcaagca aaaccttga ttggcttttc       480 accaagtcca agacagcaat taaggagctt gttgaagaaa agaagcaaag ctcatcttcc      540
actgttactg atcaatgtaa atggtctcc atggaaatct tcaaggaagg agatgaagat       600
gaaggggaaa agacgtcagt gctcaagcgt gttaaaggca aaggaagaa atgacccag        660 aaacacaaag ctcgatacca tgttaatctt gcaagagatc agttaagggc agaggcaaga     720
gcaagagcta gggaaagaac aagagaaaag ttgcggatta aaaagcttga tgatctatgc     780
aagagagttc cagatagtta ctgtcacgta agcccaacct taatactcca gtcaagctgt     840
tggagtcaaa ccgaatcaca agtaatatc aaagaaatag ttggggaatc aaatatgaac      900
cagaaattct caaaaccatc ttcaatgttg tatagctacc aacacaacct tgttgtatca     960
aaagatccaa tctccgaaag caagtacact cgttccccta aattctcatg a             1011
```

<210> SEQ ID NO 25
<211> LENGTH: 1014
<212> TYPE: DNA
<213> ORGANISM: Scaevola taccada

<400> SEQUENCE: 25

```
atgtattctt caaacccatt tccacagctc acctcatcca tccatgtctg ccctccttct       60
ccagatctct tctttggtca tgaaaagat ggttttact tcggtaacaa tagccagctc       120
caccaccatc tttacttcca caaccctttt gtctctggtg ttgtttctc tcctcaggtt      180 atggagaatg ttactacaat agatcaagat ttcatgaggc agcagcagca gcagcagcag     240
ctcactaaag aagcaggttt acaatgctgt gctgatgatc atgctcattt gttagattca    300
gtaatttccc cgtttagcaa gaaaaagtt gatgtgaaga agatcggca tagaaagatc       360 ttcagctc aaggccctag gatcggagg gtgagattgt cgttagatat cgcaagaaag       420
ttattcagtc ttcaggactt gctagggttt gataaagcaa gcaaaaccct tgattggctt    480
ttcaccaagt ccaagacagc aattaaggag cttgtagagg aaaagaagca aagctcatct    540
tccactgtta ctgatcaatg taaaatggtt tccatggaaa tcttcaagga aggagatgaa    600
gatgaagggg aaaagacgtc agtgctcaag cgtgttaaag gcaaaggaa gaaaatgacc     660 cagaagcaca agctcgaaaa ccatgttaac cttgcaagag atcagttaag ggcagaggca    720
agagccagag ctagggaaag aacaagagaa aagttgcgca ttaaaaagct tgatgatcta    780
tgcaagagag ttcctgataa ttactgtcac gtaagcccaa ccttaatact ccagtcaggc    840
tgttggagtc aaaccgaatc acaaagtaat atcaaagaaa tagttgggga atcaaatatg    900
aaccagaaat tctcaaaacc atcttcaatg ttgtatagct accaacacaa ccttgttgta    960
tcaaaagaac caatctccga aagcaagtac actcgtttgc ctatattctc atga         1014
```

<210> SEQ ID NO 26
<211> LENGTH: 1026
<212> TYPE: DNA
<213> ORGANISM: Goodenia pilosa

<400> SEQUENCE: 26

```
atgtattctt caaacccatt tccacagctt acctcatcca tccatgtctt ccctccttct       60
ccagatctct tctttggcca tgaaaagat ggtcttact accataaccc taattttgcc      120
tccaatgcta attgtttctc tccgcgggtc atcgagaatg ctgcgactac aatggagcaa    180
```

```
gatttcatca ggcagcagca gcagcagcag cagcagcagc agcagcaaca acaacaacaa    240
caacgagcaa gtttacagta ttgtgatgat catcatactc atttgttgga ttcggtggtt    300
tcccagttca gcaaaaggac cgcggaggtg aagaaagacc gccatagaaa gatcttcaca    360
gcacaaggcc ctagggatcg gagggtgaga ttgtcgatag acatcgcgag gaagttcttt    420
agtcttcagg acttgctagg gtttgacaaa gcaagcaaaa cccttgattg gctcttcacc    480
aagtccaaga tcgcaatcaa ggagcttgtc gaagaaatga acaaagctc ttcctcgacc    540 gttaccgatc aatgtaagat ggtctccatg gagatgttca aggaaggaga tgaagatgaa    600
ggtgaaggtg aaggggaaaa gacttcggtg ctgctcaagc cggttcgagg taagaggaag    660
aaaatgacca aaaggacaa agctcggagc cgtgtgaatc ttgcaagaga ccagttaagg    720
gcagaggcaa gagcaagagc tagagaaaga acactagaga agatgcgcat tcggaagctc    780
gacgatcttt gcaagcgagt tcccgataat tactgccatg tcagtccaac cttgatactc    840
cagtcaagct attggactca aaccgaaccg caaagtaaca ccaaagaaac cgttggcgaa    900
tcgaatgtga acagccagaa attctcgaaa ccatcttcaa tgttgtatag ctaccagcac    960
aaccttgttg aatcaaaaga tccaagctac caaatcaagt acgctcgttc gccaaaattt   1020
tcttga                                                              1026
```

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
tccatgtctg ccctccttct                                                20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
ttacacgcat caccctgctg                                                20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
ggcaagagca agagctaggg                                                20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
aggttgggct tacgtgacag                                                20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
gcctgatggg caggtaatca                                           20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
taccagcagc ttccattccg                                           20

<210> SEQ ID NO 33
<211> LENGTH: 19
<212> TYPE: DNA
<213> ORGANISM: Artificial Sequence
<220> FEATURE:
<223> OTHER INFORMATION: Primer

<400> SEQUENCE: 33
ccatgtctgc cctccttct                                            19

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
aacattctcc ataacctgag ga                                        22

<210> SEQ ID NO 35
<211> LENGTH: 956
<212> TYPE: DNA
<213> ORGANISM: Scaevola aemula

<400> SEQUENCE: 35
ccagatctct tctttggcca tgaaaaagat ggttttttact tcagcaacaa tagccacctc     60
caccaccatc tttactgcca caacccttttt gtctctggtg ggtgtttctc tcctcaggtt    120
atggagaatg ttactacaat agatcaagat tcatgaggc agcagcagca gcagctcact      180
aaagaagaag gtttacagtg ttgtaccgat gatcatgctc atttgttaga ttcagtcatt    240
accccgctta gcaagaaaaa agttgatgtg aagaaagatc gtcatagaaa gatcttcaca    300
gctcaaggcc ctagggatcg gagggtgaga ttgtcgttgg atatcgcaag aaagttcttc    360
agtcttcagg acttgctagg gtttgacaaa gcaagcaaaa cccttgattg cttttcacc     420
aagtccaaga cagcaattaa ggagcttgtt gaagaaaaga gcaaagctc atcttccact     480
gttactgatc aatgtaaaat ggtctccatg gaaatcttca aggaaggaga tgaagatgaa    540
ggggaaaaga cgtcagtgct caagcgtgtt aaaggcaaaa ggaagaaaat gacccagaag    600
cacaaagctc gataccatgt taatcttgca agagatcagt taagggtaga ggcaagagca    660
agagctaggg aaagaacaag agaaaagttg cggattaaaa agcttgatga tctatgcaag    720

```
agagttccag atagttactg tcacgtaagc ccaaccttaa tactccagtc aagctgttgg    780
agtcaaaccg aatcacaaag taatatcaaa gaaatagttg gggaatcaaa tatgaaccag    840
aaattctcaa aaccatcttc aatgttgtat agctaccaac acaaccttgt tgtatcaaaa    900
gatccaatct ccgaaagcaa gtacactcgt tcccctaaat tctcatgatt cttgag        956

<210> SEQ ID NO 36
<211> LENGTH: 980
<212> TYPE: DNA
<213> ORGANISM: Scaevola aemula

<400> SEQUENCE: 36
ccagatctct tctttggcca tgaaaaagat ggttttact ttagcaacaa tagccacctc     60
caccaccatc tttactgcca caacccttt gtctctggtg ggtgtttctc tcctcaggtt    120
atggagaatg ttactacaat agatcaagat ttcatgaggc tgcagcagca gcaacagcag    180
cagcagcagc agcagcagct cactaaagaa gaaggtttac agtgttgtac cgatgatcat    240
gctcatttgt tagattcagt cattaccccg cttagcaaga aaagagttga tgtgaagaaa    300
gatcgccata gaaagatctt cacagcacaa ggccctaggg atcggagggt gagattgtcg    360
ttggatatcg caagaaagtt cttcagtctt caggacttgc tagggcttga caaagcaagc    420
aaaacccttg attggctttt caccaagtca agacagcaa ttaaggagct tgttgaagaa    480
aagaagcaaa gctcatcttc cactattact gatcaatgta aaatggtctc catggaaatc    540
ttcaaggaag gagatgaaga tgaaggggaa agacgtcag agctcaagcg tgttaaaggc    600
aaaaggaaga aaatgaccca gaagcacaaa gctcgatacc atgttaatct tgcaagagat    660
cagttaaggg cagaggcaag agcaagagct agggaaagaa caagagaaaa gttgcggatt    720
aaaaagcttg atgatctatg caagagagtt ccagatagtt actgtcacgt aagcccaacc    780
ttaatactcc agtcaagctg ttggagtcaa accgaatcac aaagtaatat caaagaaata    840
gttggggaat caaatatgaa ccagaaattc tcaaaaccat cttcaatgtt gtatagctac    900
caacacaacc ttgttgtatc aaaagatcca atctccgaaa gcaaggacac tcgttcccct    960
aaattctcat gattcttgag                                                980

<210> SEQ ID NO 37
<211> LENGTH: 959
<212> TYPE: DNA
<213> ORGANISM: Scaevola aemula

<400> SEQUENCE: 37
ccagatctct tctttggcca tgaaaaagat ggttttaat tcagcaacaa tagccacctc     60
caccaccatc tttactgcca caacccttt gtctctggtg ggtgtttctc tcctcaggtt    120
atggagaatg ttactacaat agatcaagat ttcatgaggc agcagcagca gcagcagctc    180
actaaagaag aaggtttaca gtgttgtacc gatgatcatg ctcatttgtt agattcagtc    240 attacccgc ttagcaagaa aaagttgat gtgaagaaag atcgtcatag aaagatcttc    300
acagctcaag ccctaggga tcggagggtg agattgtcgt tggatatcgc aagaaagttc    360
ttcagtcttc aggacttgct agggtttgac aaagcaagca aaacccttga ttggctttc    420 accaagtcca agacagcaat taaggagctt gttgaagaaa agaagcaaag ctcatcttcc    480
actgttactg atcaatgtaa aatggtctcc atggaaatct tcaaggaagg agatgaagat    540
gaaggggaaa gacgtcagt gctcaagcgt gttaaaggca aaaggaagaa aatgacccag    600
```

```
aaacacaaag ctcgatacca tgttaatctt gcaagagatc agttaagggc agaggcaaga        660
gcaagagcta gggaaagaac aagagaaaag ttgcggatta aaaagcttga tgatctatgc        720
aagagagttc cagatagtta ctgtcacgta agcccaacct taatactcca gtcaagctgt        780
tggagtcaaa ccgaatcaca aagtaatatc aaagaaatag ttggggaatc aaatatgaac        840
cagaaattct caaaaccatc ttcaatgttg tatagctacc aacacaacct tgttgtatca        900
aaagatccaa tctccgaaag caagtacact cgttcccta aattctcatg attcttgag         959

<210> SEQ ID NO 38
<211> LENGTH: 959
<212> TYPE: DNA
<213> ORGANISM: Scaevola aemula

<400> SEQUENCE: 38
ccagatctct tctttggcca tgaaaaagat ggtttttaat tcagcaacaa tagccacctc         60
caccaccatc tttactgcca caacccttttt gtctctggtg ggtgtttctc tcctcaggtt        120
atggagaatg ttactacaat agatcaagat ttcatgaggc agcagcagca gcagcagctc        180
actaaagaag aaggtttaca gtgttgtacc gatgatcatg ctcatttgtt agattcagtc        240 attacccccgc ttagcaagaa aaagttgat gtgaagaaag atcgtcatag aaagatcttc         300
acagctcaag gccctaggga tcggagggtg agattgtcgt tggatatcgc aagaaagttc        360
ttcagtcttc aggacttgct agggtttgac aaagcaagca aaacccttga ttggcttttc        420
accaagtcca agacagcaat taaggagctt gttgaagaaa agaagcaaag ctcatcttcc        480
actgttactg atcaatgtaa aatggtctcc atggaaatct tcaaggaagg agatgaagat        540 gaagggaaa agacgtcagt gctcaagcgt gttaaaggca aaaggaagaa aatgacccag         600
aaacacaaag ctcgatacca tgttaatctt gcaagagatc agttaagggc agaggcaaga        660
gcaagagcta gggaaagaac aagagaaaag ttgcggatta aaaagcttga tgatctatgc        720
aagagagttc cagatagtta ctgtcacgta agcccaacct taatactcca gtcaagctgt        780
tggagtcaaa ccgaatcaca aagtaatatc aaagaaatag ttggggaatc aaatatgaac        840
cagaaattct caaaaccatc ttcaatgttg tatagctacc aacacaacct tgttgtatca        900
aaagatccaa tctccgaaag caagtacact cgttcccta aattctcatg attcttgag         959
```

SCAEVOLA PLANTS WITH RADIALLY SYMMETRICAL FLOWERS

CROSS-REFERENCE TO RELATED APPLICATION

This application claims the benefit of Australian Patent Application No. 2020901841, filed on Jun. 4, 2020, the disclosure of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 229752008900SUBSEQLIST.TXT, date recorded: Apr. 26, 2023, size: 35,608 bytes).

TECHNICAL FIELD

The invention relates to horticulture, plant breeding and plant genetics.

BACKGROUND

The international ornamental plant market is large and diverse and within this market, there is an ever-present need for new, innovative products and improvements to increase customer satisfaction and interest. One popular genus of plants sold in this market is *Scaevola*. Common names for *Scaevola* species include scaevolas, fan-flowers, half-flowers and naupaka, the plants' Hawaiian name. For example, *Scaevola aemula* is an ornamental plant that can be used as a ground cover, bedding plant, pot plant or hanging basket plant. It is generally considered an annual, although in mild climates it can be treated as a short lived perennial, *Scaevola aemula* is commercially available with a limited range of flower colours, primarily shades of blue, but also white, pink and light yellow.

Plants in the genus *Scaevola* "have pentamerous, bilaterally symmetrical corollas with a dorsal slit opening the tube of fused petal bases between the two dorsal petals" (Gardner, A. G., Fitz Gerald, J. N., Menz, J., Shepherd, K. A., Howarth, D. G., and Jabaily, R. S. Characterizing Floral Symmetry in the Core Goodeniaceae with Geometric Morphometrics. PLoS ONE 11(5), 2016), flowers are "completely split adaxially, with all five petals towards the ventral side, resembling a fan" (Berger, B. A., Han, J., Sessa, E. B., Gardner, A. G., Shepherd, K. A., Ricigliano, V. A., Jabaily, R. S., and Howarth, D. G. The Unexpected Depths of Genome-Skimming Data: A Case Study Examining Goodeniaceae Floral Symmetry Genes, Applications in Plant Sciences, 5(10), 2017).

Presence of a dorsal slit is generally accepted as a key identifying feature of the genus *Scaevola*. For example, all *Scaevola aemula* varieties in commercial production possess a bilaterally symmetrical corolla. This market is crowded with many breeders and similar products. The lack of diversity of flower form is one key factor that is limiting innovation in this ornamental plant category.

It would thus be beneficial to provide *Scaevola* plants with distinctive floral morphology, and methods for their production.

It is an object of the invention to provide *Scaevola* plants, and methods for their production, which overcome one or more of the deficiencies of the prior art, and/or at least to provide the public with a useful choice.

SUMMARY OF THE INVENTION

The present invention provides *Scaevola* plants producing flowers with radially, or near-radially, symmetrical arrangement of the petals. This unique flower phenotype is the result of partial, to full fusion, of the dorsally slit floral tube. In addition, the flowers also show delayed senescence. The applicant is not aware of any other commercial cultivar or wild *Scaevola* plant that exhibits this phenotype after performing an extensive prior art search.

Furthermore, the applicants have characterised the genetic determinant of the novel phenotype, which they have designated the FUSED allele. The applicants have elucidated the molecular basis of the FUSED allele, which relates to disruption of the *Scaevola* CYCLOIDEA2 (CYC2) gene. Further aspects and embodiments of the invention are based on this elucidation.

The invention also provides plant parts and propagules, such as seeds and methods for production of such plants and seeds.

Plants with Novel Floral Phenotype

In the first aspect, the invention provides a *Scaevola* plant that produces at least one flower with a floral phenotype characterised by at least one of:
 a) a fused, or partially fused, dorsal slit,
 b) a radially, or near radially symmetrical, arrangement of petals, and
 c) delayed senescence.

In one embodiment the floral phenotype is characterised by both:
 a) a fused, or partially fused, dorsal slit, and
 b) a radially, or near radially symmetrical, arrangement of petals.

In a further embodiment the fused, or partially fused, dorsal slit, leads to the radially, or near radially symmetrical, arrangement of petals.

In one embodiment the floral phenotype is characterised by all of:
 a) a fused, or partially fused, dorsal slit, and
 b) a radially, or near radially symmetrical, arrangement of petals, and
 c) delayed senescence.

In a further embodiment, the floral phenotype exhibits no increase in the number of petals per flower.

In a further embodiment, the floral phenotype exhibits no increase in the number of sepals per flower.

In a further embodiment, the floral phenotype exhibits no increase in the number of stamens per flower.

In a further embodiment, the floral phenotype exhibits no increase in the number of petals, sepals, or stamens per flower.

Reduced or Eliminated CYC2 Protein Expression or Activity

In one embodiment, the plant has reduced or eliminated expression or activity of a CYCLOIDEA2 (CYC2) protein.

In one embodiment the reduced or eliminated expression or activity of the CYC2 protein leads to the floral phenotype.

In one embodiment, the CYC2 protein has an amino acid sequence with at least 70% identity to any one of SEQ ID NO:1, 2 and 3.

In one embodiment, the CYC2 protein has an amino acid sequence with at least 70% identity to SEQ ID NO:1.

In a further embodiment the reduced or eliminated expression or activity of a CYCLOIDEA2 (CYC2) protein, leads to the floral phenotype.

In one embodiment the plant has been genetically manipulated to reduce or eliminate the expression or activity of the CYC2 protein. Various genetic manipulation techniques are known in the art, examples of which are described herein.

In one embodiment the plant has been gene-edited to reduce or eliminate expression or activity of the CYC2 protein. Various gene-editing techniques are known in the art, examples of which are described herein.

In a further embodiment the plant contains a mutation leading to the reduced or eliminated expression or activity of a CYC2 protein.

In one embodiment the mutation is a naturally occurring mutation.

In a further embodiment the mutation has been artificially induced.

In a further embodiment the plant has not been exclusively obtained by means of an essentially biological process.

Various techniques for inducing mutations are known in the art, examples of which described herein.

Reduced or Eliminated Expression of the CYC2 Gene

In one embodiment, the plant has reduced or eliminated expression or activity of a CYCLOIDEA2 (CYC2) gene.

In one embodiment the reduced or eliminated expression or activity of the CYC2 gene leads to the floral phenotype.

In one embodiment, the CYC2 gene comprises a sequence with at least 70% identity to any one of SEQ ID NO:4 to 6.

In one embodiment, the CYC2 gene comprises a sequence with at least 70% identity to SEQ ID NO:4.

In one embodiment, the CYC2 gene comprises a sequence with at least 70% identity to SEQ ID NO:5.

In one embodiment the plant has been genetically manipulated to reduce or eliminate expression or activity of the CYC2 gene.

In one embodiment the plant has been gene-edited to reduce or eliminate expression or activity of the CYC2 gene.

In one embodiment the plant has been transformed with a construct comprising a fragment of any one of the sequences of SEQ ID NO: 4 to 6, or a complement of the fragment.

Preferably the construct is designed to target an endogenous sequence corresponding to, or comprising, any one of the sequences of SEQ ID NO: 4 to 6.

In one embodiment the construct comprises a promoter operably linked to the fragment.

Preferably the promoter is heterologous to the fragment.

In one embodiment the construct brings about the reduced or eliminated expression or activity of a CYCLOIDEA2 (CYC2) protein or gene.

In one embodiment the construct is an antisense construct.

In one embodiment the construct is a hairpin construct.

In a further embodiment the construct is a gene-editing construct. In a further embodiment the fragment encodes a guide RNA in the gene-editing construct.

In a further embodiment the plant contains a mutation leading to the reduced or eliminated expression or activity of a CYC gene.

In one embodiment the mutation creates a premature stop codon.

In one embodiment the mutation creates a new allele of the CYC2 gene.

In one embodiment the allele is present in the heterozygous state.

In a further embodiment the allele is present in the homozygous state.

In one embodiment, when the allele is present in the heterozygous state, the plant expresses the floral phenotype in the first few flowers that develop on the plant, and later flowers are of normal (wild-type) appearance.

In a further embodiment, when the allele is present in the heterozygous state, the plant expresses the floral phenotype in the first flower, preferably the first 2 flowers, preferably the first 3 flowers, preferably the first 4, preferably the first 5 flowers that develop on the plant, and later flowers are of normal (wild-type) appearance.

In a further embodiment, when the allele is present in the homozygous state, the plant expresses the floral phenotype in all or nearly all flowers produced.

In a further embodiment, when the allele is present in the homozygous state, the plant expresses the floral phenotype in at least 50%, preferably at least 60%, more preferably at least 70%, more preferably at least 80%, more preferably at least 90%, more preferably at least 95%, more preferably at least 97%, more preferably at least 99%, more preferably 100%, of flowers produced.

FUSED Allele

In one embodiment the plant contains the FUSED allele.

In one embodiment the floral phenotype is a result of presence of the FUSED allele.

In one embodiment the floral phenotype is a result of the plant containing the FUSED allele.

In one embodiment, when the allele is present in the heterozygous state, the plant expresses the floral phenotype in the first few flowers that develop on the plant, and later flowers are of normal (wild-type) appearance.

In one embodiment the "first few flowers" means the first 1, more preferably the first 2, more preferably the first 3, more preferably the first 4, more preferably the first 5, more preferably the first 6, more preferably the first 7, more preferably the first 8, more preferably the first 9, more preferably the first 10 flowers that develop on the plant.

In a further embodiment "later flowers" are those that develop after the "first few flowers".

In a further embodiment, when the allele is present in the homozygous state, the plant expresses the floral phenotype in all or nearly all flowers produced.

In a further embodiment, when the allele is present in the homozygous state, the plant expresses the floral phenotype in at least 50%, preferably at least 60%, more preferably at least 70%, more preferably at least 80%, more preferably at least 90%, more preferably at least 95%, more preferably at least 97%, more preferably at least 99%, more preferably 100%, of flowers produced.

In one embodiment the FUSED allele contains a premature stop codon in the coding sequence of the CYC2 gene.

In one embodiment the stop codon results in elimination of production of a CYC2 protein from the FUSED allele.

In a further embodiment the stop codon results in production of a truncated CYC2 protein from the FUSED allele.

In one embodiment the truncated CYC2 protein has reduced activity relative to the full-length CYC2 protein.

In one embodiment the truncated CYC2 protein is not active.

In one embodiment the truncated CYC2 protein does not possess the function of the full-length CYC2 protein.

In one embodiment the truncated CYC2 protein is non-functional.

In a further embodiment the invention provides a plant containing at least one copy of the FUSED allele.

In one embodiment the plant is heterozygous for the FUSED allele.

In a further embodiment the plant is homozygous for the FUSED allele.

In one embodiment, when the allele is present in the heterozygous state, the plant expresses the floral phenotype in the first few flowers that develop on the plant, and later flowers are of normal (wild-type) appearance.

In a further embodiment, when the allele is present in the homozygous state, the plant expresses the floral phenotype in all or nearly all flowers produced.

In a further embodiment, when the allele is present in the homozygous state, the plant expresses the floral phenotype in at least 50%, preferably at least 60%, more preferably at least 70%, more preferably at least 80%, more preferably at least 90%, more preferably at least 95%, more preferably at least 97%, more preferably at least 99%, more preferably 100%, of flowers produced.

In one embodiment the FUSED allele comprises a sequence selected from any one of SEQ ID NO:7 and SEQ ID NO:8.

In one embodiment the FUSED allele comprises the sequence of SEQ ID NO:7.

In one embodiment the FUSED allele comprises the sequence of SEQ ID NO:8.

Plant Produced from Deposited Seed

In a further embodiment the plant of the invention is produced from a seed deposited under Accession Number: NCIMB 43619.

In a further embodiment the invention provides a plant produced from a seed deposited under Accession Number: NCIMB 43619.

Genetic Determinant in Deposited Seed

In a further embodiment, the floral phenotype of a plant of the invention is the result of a genetic determinant present in a seed deposited under Accession Number: NCIMB 43619.

In one embodiment the genetic determinant is the FUSED allele.

In one embodiment the FUSED allele is characterised by at least one of:
a) the presence of an adenine (A) at position corresponding to nucleotide 39 in the sequence of SEQ ID NO: 7,
b) the presence of an adenine (A) at position corresponding to nucleotide 39 in the sequence of SEQ ID NO: 8,
c) the presence of an adenine (A) at position corresponding to nucleotide 99 in the sequence of SEQ ID NO: 24.

In a preferred embodiment the adenine (A) is a substitution of a cytosine (C) at the same position in the corresponding wild-type sequence.

In a preferred embodiment:
a) SEQ ID NO: 4 is the wild-type sequence corresponding to SEQ ID NO: 7,
b) SEQ ID NO: 5 is the wild-type sequence corresponding to SEQ ID NO: 8, and
c) SEQ ID NO: 23 is the wild-type sequence corresponding to SEQ ID NO: 24.

In one embodiment the FUSED allele comprises a sequence selected from any one of SEQ ID NO:7, SEQ ID NO:8 and SEQ ID NO:24.

In one embodiment the FUSED allele comprises the sequence of SEQ ID NO:7.

In one embodiment the FUSED allele comprises the sequence of SEQ ID NO:8.

In one embodiment the FUSED allele comprises the sequence of SEQ ID NO:24.

Plant Parts and Propagules

In a further aspect, the invention provides a plant cell, plant part, propagule, cutting, cell culture, tissue culture, or callus of the plant of the invention.

In one embodiment the tissue, callus, or cells is/are produced from a plant part selected from the group consisting of pollen, ovules, embryos, protoplasts, meristematic cells, callus, leaves, anthers, cotyledons, hypocotyl, pistils, roots, root tips, flowers, seeds, petiole and stems.

In one embodiment the plant cell, plant part, propagule, cutting, cell culture or tissue culture, or callus is capable of producing a plant of the invention.

In one embodiment the plant cell, plant part, propagule, cutting, cell culture, tissue culture, or callus has reduced or eliminated expression or activity of a CYC2 protein.

In one embodiment the plant cell, plant part, propagule, cutting, cell culture, tissue culture, or callus has reduced or eliminated expression or activity of a CYC2 gene.

In one embodiment the plant cell, plant part, propagule, cutting, cell culture, tissue culture, or callus has a mutation that leads to the reduced or eliminated expression or activity of a CYC2 gene.

In one embodiment the plant cell, plant part, propagule, cutting, cell culture, tissue culture, or callus contains at least one copy of the FUSED allele.

In one embodiment the invention provides a *Scaevola aemula* plant, plant cell, plant part, propagule, seed, cutting, cell culture, tissue culture, or callus thereof, wherein the plant, plant cell, plant part, propagule, seed, cutting, cell culture, tissue culture, or callus comprises the FUSED allele.

In one embodiment the FUSED allele is in the heterozygous state.

In a further embodiment the FUSED allele is in the homozygous state.

In one embodiment the FUSED allele is characterised by at least one of:
d) the presence of an adenine (A) at position corresponding to nucleotide 39 in the sequence of SEQ ID NO: 7,
e) the presence of an adenine (A) at position corresponding to nucleotide 39 in the sequence of SEQ ID NO: 8,
f) the presence of an adenine (A) at position corresponding to nucleotide 99 in the sequence of SEQ ID NO: 24.

In a preferred embodiment the adenine (A) is a substitution of a cytosine (C) at the same position in the corresponding wild-type sequence.

In a preferred embodiment:
d) SEQ ID NO: 4 is the wild-type sequence corresponding to SEQ ID NO: 7,
e) SEQ ID NO: 5 is the wild-type sequence corresponding to SEQ ID NO: 8, and
f) SEQ ID NO: 23 is the wild-type sequence corresponding to SEQ ID NO: 24.

In one embodiment the FUSED allele comprises a sequence selected from any one of SEQ ID NO:7, SEQ ID NO:8 and SEQ ID NO:24.

In one embodiment the FUSED allele comprises the sequence of SEQ ID NO:7.

In one embodiment the FUSED allele comprises the sequence of SEQ ID NO:8.

In one embodiment the FUSED allele comprises the sequence of SEQ ID NO:24.

Seed

In one embodiment the propagule is a seed.

In a further embodiment the invention provides a seed capable of producing a plant of the invention.

In one embodiment the seed is produced by a plant generated from a seed deposited under Accession Number: NCIMB 43619.

In a further embodiment the invention provides a *Scaevola* plant, comprising at least one recessive mutant allele that produces at least one flower with a floral phenotype characterised by at least one of:
a) a fused, or partially fused, dorsal slit,
b) a radially, or near radially symmetrical, arrangement of petals, and
c) delayed senescence, and wherein a sample of representative seed of the *Scaevola* plant, comprising the mutant allele that produces said flower, is deposited under Accession Number: NCIMB 43619.

In one embodiment the floral phenotype is conferred by presence of the mutant allele.

In a further embodiment the mutant allele is the FUSED allele as herein described.

In a further embodiment the invention provides a *Scaevola* plant that produces at least one flower with a floral phenotype characterised by at least one of:
a) a fused, or partially fused, dorsal slit,
b) a radially, or near radially symmetrical, arrangement of petals, and
c) delayed senescence, wherein the *Scaevola* plant is obtained by introgression of the floral phenotype from a plant grown from the seed deposited at NCIMB under the Accession Number: NCIMB 43619.

In one embodiment the plant has been selected for floral phenotype.

In a further embodiment the floral phenotype is conferred by presence of a recessive mutant allele.

In a further embodiment the mutant allele is the FUSED allele as herein described.

In one embodiment the FUSED allele is characterised by at least one of:
g) the presence of an adenine (A) at position corresponding to nucleotide 39 in the sequence of SEQ ID NO: 7,
h) the presence of an adenine (A) at position corresponding to nucleotide 39 in the sequence of SEQ ID NO: 8,
i) the presence of an adenine (A) at position corresponding to nucleotide 99 in the sequence of SEQ ID NO: 24.

In a preferred embodiment the adenine (A) is a substitution of a cytosine (C) at the same position in the corresponding wild-type sequence.

In a preferred embodiment:
g) SEQ ID NO: 4 is the wild-type sequence corresponding to SEQ ID NO: 7,
h) SEQ ID NO: 5 is the wild-type sequence corresponding to SEQ ID NO: 8, and
i) SEQ ID NO: 23 is the wild-type sequence corresponding to SEQ ID NO: 24.

In one embodiment the FUSED allele comprises a sequence selected from any one of SEQ ID NO:7, SEQ ID NO:8 and SEQ ID NO:24.

In one embodiment the FUSED allele comprises the sequence of SEQ ID NO:7.

In one embodiment the FUSED allele comprises the sequence of SEQ ID NO:8.

In one embodiment the FUSED allele comprises the sequence of SEQ ID NO:24.

Method for Producing a *Scaevola* Plant with the Novel Floral Phenotype

In a further aspect, the invention provides a method for producing a *Scaevola* plant of the invention with at least one flower with the floral phenotype.

Reducing or Eliminating CYC2 Protein Expression or Activity

In one embodiment, the method includes the step of reducing or eliminating expression or activity of a CYC2 protein in the plant.

In a further embodiment the reducing or eliminating expression or activity of a CYC2 protein, leads to the floral phenotype.

In one embodiment the method includes the step of genetically manipulating the plant to reduce or eliminate expression or activity of the CYC2 protein.

In one embodiment the method includes the step of gene-editing the plant to reduce or eliminate expression or activity of the CYC2 protein.

In a further embodiment the method includes the step of inducing a mutation in the plant to reduce or eliminate expression or activity of a CYC2 protein.

Reducing or Eliminating CYC2 Gene Expression or Activity

In one embodiment, the method includes the step of reducing or eliminating expression or activity of a CYC2 gene.

In one embodiment, the CYC2 gene comprises a sequence with at least 70% identity to any one of SEQ ID NO:4 to 6.

In one embodiment, the CYC2 gene comprises a coding sequence with at least 70% identity to SEQ ID NO:4.

In one embodiment, the CYC2 gene comprises a coding sequence with at least 70% identity to SEQ ID NO:5.

In a further embodiment the reduced or eliminated expression or activity of a CYC2 gene, leads to the floral phenotype.

In one embodiment the method includes the step of genetically manipulating the plant to reduce or eliminate expression or activity of the CYC2 gene.

In one embodiment the method includes the step of gene-editing the plant to reduce or eliminate expression or activity of the CYC2 gene.

In one embodiment the method incudes the step of transforming the plant with a construct comprising a fragment of any one of the sequences of SEQ ID NO: 4 to 6, or a complement of the fragment.

Preferably the construct is designed to target an endogenous sequence corresponding to, or comprising, any one of the sequences of SEQ ID NO: 4 to 6.

In one embodiment the construct comprises a promoter operably linked to the fragment. Preferably the promoter is heterologous to the fragment.

In one embodiment transformation of the plant with the construct brings about the reduced or eliminated expression or activity of a CYCLOIDEA2 (CYC2) protein or gene.

In one embodiment the construct is an antisense construct.

In one embodiment the construct is a hairpin construct.

In a further embodiment the construct is a gene-editing construct. In a further embodiment the fragment encodes a guide RNA in the gene-editing construct.

In a further embodiment the method includes the step of inducing a mutation in the plant to reduce or eliminate expression or activity of a CYC gene.

In one embodiment the mutation creates a premature stop codon in the CYC2 gene.

In one embodiment the mutation creates a new allele of the CYC2 gene.

In one embodiment the allele is present in the heterozygous state.

In a further embodiment the allele is present in the homozygous state.

In one embodiment, when the allele is present in the heterozygous state, the plant expresses the floral phenotype in the first few flowers that develop on the plant, and later flowers are of normal (wild-type) appearance.

In a further embodiment, when the allele is present in the homozygous state, the plant expresses the floral phenotype in all or nearly all flowers produced.

In one embodiment "nearly all" means at least 50%, preferably at least 60%, more preferably at least 70%, more preferably at least 80%, more preferably at least 90%, more preferably at least 95%, more preferably at least 97%, more preferably at least 99%, more preferably 100%, of flowers produced.

Thus, in one embodiment, when the allele is present in the homozygous state, the plant expresses the floral phenotype in at least 50%, preferably at least 60%, more preferably at least 70%, more preferably at least 80%, more preferably at least 90%, more preferably at least 95%, more preferably at least 97%, more preferably at least 99%, more preferably 100%, of flowers produced.

Crossing to Produce a Plant of the Invention

In one embodiment the method includes the step of crossing a plant of the invention with another plant to produce a *Scaevola* plant with at least one flower with the floral phenotype.

In one embodiment the other plant may also be a plant of the invention.

In a further embodiment the method includes the step of testing the off-spring of the cross for at least one of:
 a) reduced or eliminated CYC2 protein expression or activity,
 b) reduced or eliminated CYC2 gene expression or activity
 c) presence of a mutation that disrupts CYC2 gene expression, and
 d) presence of the FUSED allele,
wherein any one of a) to d) indicates that the plant will produce at least one flower with the floral phenotype.

Selfing a Plant of the Invention

In one embodiment the method includes the step of self-pollinating a plant of the invention.

In a further embodiment the method includes the step of testing the off-spring of the self-pollinating for at least one of:
 a) reduced or eliminated CYC2 protein expression or activity,
 b) reduced or eliminated CYC2 gene expression or activity,
 c) presence of a mutation that disrupts CYC2 gene expression, and
 d) presence of the FUSED allele,
wherein any one of a) to d) indicates that the plant will produce at least one flower with the floral phenotype.

Introducing the FUSED Allele

In one embodiment the method includes the step of introducing the FUSED allele into a plant to produce a *Scaevola* plant of the invention with at least one flower with the floral phenotype.

In one embodiment the method involves crossing a first plant containing the FUSED allele with a second plant, to produce the plant of the invention containing the FUSED allele.

In one embodiment the first plant is heterozygous for the FUSED allele.

In a further embodiment the first plant is homozygous for the FUSED allele.

In one embodiment the second plant does not contain the FUSED allele.

In a further embodiment the second plant is heterozygous for the FUSED allele.

In a further embodiment the second plant is homozygous for the FUSED allele.

In a further embodiment the plant of the invention resulting from the crossing is heterozygous for the FUSED allele.

In a further embodiment the plant of the invention resulting from the crossing is homozygous for the FUSED allele.

In a further embodiment the method includes the step of detecting the presence of the FUSED allele in the plant of the invention resulting from the cross.

In one embodiment the method includes the step of detecting the presence of the FUSED allele in the heterozygous state.

In one embodiment the method includes the step of detecting the presence of the FUSED allele in the homozygous state.

In one embodiment the FUSED allele is detected by a polymerase chain reaction (PCR)-based method.

In a further embodiment the FUSED allele is detected using a Cleaved Amplified Polymorphic Sequences (CAPS) molecular marker system.

Vegetative Propagation

In a further embodiment the plant is produced by vegetatively propagating a *Scaevola* plant of the invention.

In one embodiment the vegetative propagation method comprises the steps of: (a) collecting tissue capable of being propagated from the *Scaevola* plant of the invention; (b) cultivating said tissue to obtain proliferated shoots; and (c) rooting said proliferated shoots to obtain rooted plantlets.

In a further embodiment the invention provides a method of producing a *Scaevola* plant that produces at least one flower with a floral phenotype characterised by a radially symmetrical arrangement of petals as a result of the plant containing the FUSED allele, wherein the method includes at least one of:
 a) genetically manipulating the plant to produce the FUSED allele in the plant,
 b) gene-editing the plant to produce the FUSED allele in the plant
 c) inducing a mutation that produces the FUSED allele in the plant,
 d) crossing a plant of the invention with another plant,
 e) selfing a plant of the invention, and
 f) introducing the FUSED allele into the plant.

In one embodiment the method includes the step of testing the plant produced for the presence of the FUSED allele.

Plant Produced by a Method of the Invention

In a further embodiment the invention provides a plant produced by the method of the invention.

Method of Producing Seed

In a further aspect the invention provides a method for producing *Scaevola* seed, the method comprising the step of growing a *Scaevola* plant of the invention and harvesting the resultant seed.

In a further aspect the invention provides a method for producing *Scaevola* seed, the method comprising the step of crossing a *Scaevola* plant of the invention with another *Scaevola* plant and harvesting the resultant seed.

In a further aspect the invention provides a method for producing *Scaevola* seed, the method comprising self-pollinating a *Scaevola* plant of the invention and harvesting the resultant seed.

In one embodiment the plant of the invention contains the FUSED allele.

In a further embodiment the seed produced contains the FUSED allele.

Marker Assisted Selection

In a further aspect the invention provides a method for identifying a Scaevola plant with a genotype indicative of the floral phenotype of the invention, the method comprising testing a plant for at least one of:
  a) reduced or eliminated CYC2 protein expression or activity,
  b) reduced or eliminated CYC2 gene expression or activity
  c) presence of a mutation that disrupts CYC2 gene expression,
  d) presence of the FUSED allele, and
  e) presence of a marker linked to any of a) to d)
wherein any one of a) to e) indicates that the plant will produce at least one flower with the floral phenotype.

A method of detecting in a Scaevola plant at least one of:
  a) reduced or eliminated CYC2 protein expression or activity,
  b) reduced or eliminated CYC2 gene expression or activity
  c) presence of a mutation that disrupts CYC2 gene expression,
  d) presence of the FUSED allele, and
  e) presence of a marker linked to any of a) to d), In one embodiment the detection of any one of a) to e) indicates that the plant will produce at least one flower with the floral phenotype of the invention.

Marker

In a further aspect the invention provides a marker linked to the floral phenotype of the invention.

In a further embodiment the marker can be used to detect the FUSED allele of the invention.

In a further embodiment the marker can be used to distinguish between plants containing the FUSED allele and those that do not.

In a further embodiment the marker comprises at least one of:
  a) a fragment of the sequence of SEQ ID NO:7 or 8 including the adenine (A) at a position equivalent to nucleotide 39 in SEQ ID NO:7 or 8,
  b) the complement of the fragment of a),
  c) a fragment of the sequence of SEQ ID NO: 24 that comprises the adenine (A) at a position equivalent to nucleotide position 99 in SEQ ID NO:24, and
  d) the complement of the fragment in c).

In a further aspect the invention provides a marker linked to the FUSED allele of the invention.

Preferably the marker is in Linkage Disequilibrium (LD) with the FUSED allele at a D' value of at least 0.1, more preferably at least 0.2, more preferably at least 0.3, more preferably at least 0.4, more preferably at least 0.5.

Preferably the marker is in LD with the FUSED allele at a $R^2$ value of at least 0.05, more preferably at least 0.075, more preferably at least 0.1, more preferably at least 0.2, more preferably at least 0.3, more preferably at least 0.4, more preferably at least 0.5.

Growing a Plant from the Seed

A further embodiment relates to planting and growing the seed of the invention to produce a plant of the invention.

In one embodiment the plant produced contains at least one copy of the FUSED allele. In a further embodiment the plant is heterozygous for the FUSED allele.

In a further embodiment the plant is homozygous for the FUSED allele.

In a further embodiment the invention provides a plant produced by the method of the invention.

DETAILED DESCRIPTION OF THE INVENTION

The applicants have in their breeding program, produced novel Scaevola plants that produce flowers with a novel floral phenotype. The phenotype is characterised by a radial or near radial symmetrical arrangement of petals. Without wishing to be bound by theory, the applicants consider that this arrangement of petals is the result of fusion or partially fusion of the floral tube in these flowers. In addition, the applicants have surprisingly shown that flowers with the described floral phenotype additionally show delayed senescence relative to wild-type flowers.

The applicants have shown that the novel phenotype is controlled by a mutant recessive allele that they have designated the FUSED allele. The applicants have further elucidated the molecular basis of the FUSED allele. Specifically, the applicants have shown that the FUSED allele is characterised by a premature stop codon in the coding sequence of the CYCLOIDEA2 (CYC2) gene. One of average skill in the art would therefore expect that other deletions or disruptions to the CYCLOIDEA2 gene/protein in Scaevola would result in the same phenotypic expression of radial floral symmetry. Various aspects and embodiments of the invention are based on these elucidations.

Floral Tube

The floral tube of a Scaevola flower extends from above the ovary to the base of the corolla and in all species of the genus Scaevola, it contains a dorsal slit.

Dorsal Slit

As used herein the term 'dorsal slit' refers to an opening in the floral tube of a Scaevola flower between the dorsal petals and extending from the edge of the corolla towards the ovary.

Fused Dorsal Slit

In accordance with the invention, when the dorsal slit of the a Scaevola flower is fused, or partially fused, this results in the floral phenotype of the invention characterised by radial symmetry, or partial radial symmetry, respectively.

In a preferred embodiment the dorsal slit is fused.

In a preferred embodiment the floral phenotype of the invention is characterised by radial symmetry.

Radial Symmetry

Radially symmetrical flowers, or flowers with radial symmetry, have multiple lines of symmetry.

In one embodiment radial symmetry as used herein is the phenotypic arrangement of petals in a Scaevola flower caused by reduced or eliminated expression or activity of a CYCLOIDEA2 (CYC2) gene or protein.

In one embodiment radial symmetry as used herein is the phenotypic arrangement of petals in a Scaevola flower caused by the presence of the FUSED allele.

Partial Fusion of the Dorsal Slit and Partial Radial Symmetry

In one embodiment when the FUSED allele is in the homozygous state, the floral phenotype is characterised by a fully fused dorsal slit. Preferably, when the FUSED allele is in the homozygous state, essentially all flowers exhibit this phenotype. Preferably, when the FUSED allele is in the homozygous state, all flowers exhibit this phenotype.

In one embodiment when the FUSED allele is in the homozygous state, the floral phenotype is characterised by a full radial symmetry. Preferably, when the FUSED allele is in the homozygous state, essentially all flowers exhibit this phenotype. Preferably, when the FUSED allele is in the homozygous state, all flowers exhibit this phenotype.

In some embodiments when the FUSED allele is in the heterozygous state, the floral phenotype is characterised by a partially fused dorsal slit. In one embodiment, when the FUSED allele is in the heterozygous state, one or more of the flowers exhibit this phenotype. In one embodiment, when the FUSED allele is in the heterozygous state, the first few flowers exhibit a fully fused dorsal slit and later flowers exhibit a partially fused dorsal slit.

In some embodiments when the FUSED allele is in the heterozygous state, the floral phenotype is characterised by a partial radial symmetry. In one embodiment, when the FUSED allele is in the heterozygous state, one or more of the flowers exhibit this phenotype. In one embodiment, when the FUSED allele is in the heterozygous state, the first few flowers exhibit full radial symmetry and later flowers exhibit partial radial symmetry.

Delayed Senescence

The applicant has shown that the radially symmetrical flowers of the present invention have delayed senescence compared to normal *Scaevola aemula* flowers. Normal *Scaevola aemula* flowers senesce within 24 hours after cross-pollination. The applicants have shown that the flowers of the present invention persist for substantially longer prior to senescence and assert that this is due to the structure of the radially symmetrical flowers. Specifically, the applicants assert that he unique corolla structure limits pollinator access to the stigma and pollen, thereby reducing the opportunity for cross-pollination, and thereby extending the shelf life of the product. This unexpected advantage is desirable from a commercial perspective.

In one embodiment senescence of flowers with the floral phenotype of the invention is delayed by at least 3 hours, preferably at least 6 hours, more preferably at least 12 hours, more preferably at least 18 hours, more preferably at least 24 hours, more preferably at least 36 hours, more preferably at least 48 hours, more preferably at least 60 hours, more preferably at least 72 hours, more preferably at least 84 hours, more preferably at least 96 hours, more preferably at least 108 hours, 120 hours, relative to that in a control plant

CYCLOIDEA (CYC)

The term CYCLOIDEA and abbreviation CYC refers to transcription factor gene family members that belong to the TCP family and play a role in specifying dorsal identity in the corolla and androecium of bilaterally symmetrical flowers (Han, J., 2018. PhD Thesis: Duplications and expression of CYCLOIDEA-like genes in Goodeniaceae, St. John's University, New York; Fambrini, M, Salvini, M, Basile, A, and Pugliesi, C. 2014. Transposon-dependent induction of Vincent van Gogh's sunflowers: Exceptions revealed, Genesis 52:315-327).

CYCLOIDEA2 (CYC2) Protein

In one embodiment the CYCLOIDEA2 (CYC2) protein in accordance with the invention has a sequence selected from any one of SEQ ID NO:1, 2 and 3 or a variant thereof.

Preferably the CYCLOIDEA2 (CYC2) protein in accordance with the invention has the sequence with at least 70% identity to any one of SEQ ID NO:1, 2 and 3.

In one embodiment the CYCLOIDEA2 (CYC2) protein in accordance with the invention has the sequence of SEQ ID NO:1, or a variant thereof.

Preferably the CYCLOIDEA2 (CYC2) protein in accordance with the invention has a sequence with at least 70% identity to that of SEQ ID NO:1.

In one embodiment the CYC2 protein comprises all of motifs 1 to 14 as described in Chen, J., Shen, C, Guo, Y and Rao, G 2018, Patterning the *Asteraceae capitulum*: Duplications and differential expression of the flower symmetry CYC2-like genes. Frontiers in Plant Science, April 25, Volume 9, Article 551.

In one embodiment the CYC2 protein comprises all of motifs 1, 2 and 4 as described in Chen, et al. 2018. These motifs are present in all the CYC2-like proteins from Asterales, as described by the authors.

The present applicants have identified motifs in *Scaevola* sequences corresponding to motifs 1, 3 and 4 as described in Chen et al., 2018.

These motifs are summarised in the Summary of Sequences and illustrated in FIG. 14.

In one embodiment the CYC2 protein comprises a Motif 1 with a sequence selected from any one of SEQ ID NO: 9 to 14.

In one embodiment the CYC2 protein comprises a Motif 1 with the sequence of SEQ ID NO:9.

In one embodiment the CYC2 protein comprises a Motif 1 with the sequence of SEQ ID NO:10.

In one embodiment the CYC2 protein comprises a Motif 1 with the sequence of SEQ ID NO:11.

In one embodiment the CYC2 protein comprises a Motif 1 with the sequence of SEQ ID NO:12.

In one embodiment the CYC2 protein comprises a Motif 1 with the sequence of SEQ ID NO:13.

In one embodiment the CYC2 protein comprises a Motif 1 with the sequence of SEQ ID NO:14.

In one embodiment the CYC2 protein comprises a Motif 2 with a sequence selected from any one of SEQ ID NO: 15 to 19.

In one embodiment the CYC2 protein comprises a Motif 2 with the sequence of SEQ ID NO:15.

In one embodiment the CYC2 protein comprises a Motif 2 with the sequence of SEQ ID NO:16.

In one embodiment the CYC2 protein comprises a Motif 2 with the sequence of SEQ ID NO:17.

In one embodiment the CYC2 protein comprises a Motif 2 with the sequence of SEQ ID NO:18.

In one embodiment the CYC2 protein comprises a Motif 2 with the sequence of SEQ ID NO:19.

In one embodiment the CYC2 protein comprises a Motif 4 with a sequence selected from any one of SEQ ID NO: 20 to 22.

In one embodiment the CYC2 protein comprises a Motif 4 with the sequence of SEQ ID NO:20.

In one embodiment the CYC2 protein comprises a Motif 4 with the sequence of SEQ ID NO:21.

In one embodiment the CYC2 protein comprises a Motif 4 with the sequence of SEQ ID NO:22.

In a further embodiment the CYC2 protein comprises a Motif 1, a Motif 2 and a Motif 4, selected from those described above.

In one embodiment the CYCLOIDEA2 (CYC2) protein in accordance with the invention has the sequence selected from any one of SEQ ID NO:1, 2 and 3.

In one embodiment the CYCLOIDEA2 (CYC2) protein in accordance with the invention has the sequence of SEQ ID NO:1.

CYCLOIDEA2 (CYC2) DNA in one embodiment the CYCLOIDEA2 (CYC2) gene in accordance with the invention comprises a sequence selected from any one of SEQ ID NO:4, 5, and 6, or a variant thereof.

Preferably the CYCLOIDEA2 (CYC2) gene in accordance with the invention comprises a sequence with at least 70% identity to a sequence selected from any one of SEQ ID NO:4, 5, and 6.

In one embodiment the CYCLOIDEA2 (CYC2) gene in accordance with the invention comprises the sequence of SEQ ID NO:4 or a variant thereof.

Preferably the CYCLOIDEA2 (CYC2) gene in accordance with the invention comprises a sequence with at least 70% identity to the sequence of SEQ ID NO:4.

In one embodiment the CYCLOIDEA2 (CYC2) gene in accordance with the invention comprises the sequence of SEQ ID NO:5 or a variant thereof.

Preferably the CYCLOIDEA2 (CYC2) gene in accordance with the invention comprises a sequence with at least 70% identity to the sequence of SEQ ID NO:5.

In one embodiment the CYCLOIDEA2 (CYC2) gene in accordance with the invention comprises the sequence of SEQ ID NO:6 or a variant thereof.

Preferably the CYCLOIDEA2 (CYC2) gene in accordance with the invention comprises a sequence with at least 70% identity to the sequence of SEQ ID NO:6.

In one embodiment the CYCLOIDEA2 (CYC2) gene in accordance with the invention comprises the sequence of SEQ ID NO:4.

In one embodiment the CYCLOIDEA2 (CYC2) gene in accordance with the invention comprises the sequence of SEQ ID NO:5.

In one embodiment the CYCLOIDEA2 (CYC2) gene in accordance with the invention comprises the sequence of SEQ ID NO:5.

FUSED Allele in one embodiment the FUSED allele is characterised by a mutation in the coding sequence of the CYC2 gene.

In a further embodiment the stop codon results in production of a truncated CYC2 protein.

In a further embodiment the stop codon eliminates production of the CYC2 protein.

In a further embodiment the stop codon eliminates the activity of the CYC2 protein.

In a further embodiment the premature stop codon is created by a cytosine (C) to adenine (A) replacement at a position corresponding nucleotide position 39 in SEQ ID NO:4.

In a further embodiment the stop codon is a thymidine, adenine, adenine (TAA) stop codon at positions corresponding to nucleotide positions 37, 38 and 39 respectively in SEQ ID NO:4, wherein the second adenine (A) is created by a cytosine (C) to adenine (A) replacement at a position corresponding to nucleotide position 39 in SEQ ID NO:4.

In a further embodiment the FUSED allele is characterised by presence of an adenine (A) at a position corresponding to nucleotide position 39 in SEQ ID NO:4.

In a further embodiment the sequence of the FUSED allele is as presented in FIG. 9.

In one embodiment the FUSED allele comprises a sequence selected from SEQ ID NO: 7, 8 and 24.

In one embodiment the FUSED allele comprises the sequence of SEQ ID NO: 7.

In one embodiment the FUSED allele comprises the sequence of SEQ ID NO: 8.

In one embodiment the FUSED allele comprises the sequence of SEQ ID NO: 24.

Methods for Identifying Alleles

Methods for detecting the presence of polymorphisms and mutations are well-known to those skilled in the art. Such methods include DNA sequencing, Polymerase Chain Reaction (PCR) based methods, allele specific PCR, hybridisation based methods, hybridisation with an oligonucleotide probe, restriction fragment length polymorphism and oligonucleotide Ligation assay (Ibrahim, A, Bakir, M, Khan, H and Shobrak, M. 2010, A Brief Review of Molecular Techniques to Assess Plant Diversity. International Journal of Molecular Sciences 11(5): 2079-2096.

CAPS Methods

Cleaved Amplified Polymorphic Sequences (CAPS) polymorphisms are differences in restriction fragment lengths caused by mutations that create or abolish restriction endonuclease recognition sites in PCR amplicons produced by locus-specific oligonucleotide primers.

According to the present invention a CAPS molecular marker system can be used to identify plants heterozygous or homozygous for the FUSED allele from plants not possessing the allele (Agarwal, M, Shrivastava, N and Padh, H. 2008. Advances in molecular marker techniques and their applications in plant sciences. Plant Cell Reports 27: 617-631).

Marker Assisted Selection

Marker assisted selection (MAS) is an approach that is often used to identify plants that possess a particular trait using a genetic marker, or markers, associated with that trait. MAS may allow breeders to identify and select plants at a young age and is particularly valuable for traits that are difficult to measure at a young stage. The best markers for MAS are the causal mutations, but where these are not available, a marker that is in strong linkage disequilibrium with the causal mutation can also be used. Such information can be used to accelerate genetic gain, or reduce trait measurement costs, and thereby has utility in commercial breeding programs.

Methods for marker assisted selection are well known to those skilled in the art, for example: (Collard, B. C. Y. and D. J. Mackill, 2008. Marker-assisted selection: an approach for precision plant breeding in the twenty-first century. Philosophical Transactions of the Royal Society B-Biological Sciences. 363(1491): p. 557-572.

Markers

Markers for use in the methods of the invention may include nucleic acid markers, such as single nucleotide polymorphisms (SNPs), simple sequence repeats (SSRs or microsatellites), insertions, substitutions, indels and deletions. Preferably the marker is in linkage disequilibrium (LD) with the floral phenotype.

Preferably the marker is in LD with the floral phenotype at a D' value of at least 0.1, more preferably at least 0.2, more preferably at least 0.3, more preferably at least 0.4, more preferably at least 0.5.

Preferably the marker is in LD with the floral phenotype at a $R^2$ value of at least 0.05, more preferably at least 0.075, more preferably at least 0.1, more preferably at least 0.2, more preferably at least 0.3, more preferably at least 0.4, more preferably at least 0.5.

The term "linkage disequilibrium" or LD as used herein, refers to a derived statistical measure of the strength of the association or co-occurrence of two independent genetic markers. Various statistical methods can be used to summarize linkage disequilibrium (LD) between two markers but in practice only two, termed D' and $R^2$, are widely used.

Markers linked with the trait may be of any type including but not limited to, SNPs, substitutions, insertions, deletions, indels or simple sequence repeats (SSRs).

*Scaevola*

*Scaevola* plants belong to the Goodeniaceae family. Within the Goodeniaceae family there are 12 accepted genera and about 420 species (Carolin R. C., Rajput M. T. M., Morrison P. Goodeniaceae. In: George AS, editor, Flora of Australia Volume 35. Canberra: Australian Government Publishing Service; 1992. pp. 4-300), *Scaevola* is one of the 12 genera and approximately 100 species are currently listed in the genus.

In one embodiment the *Scaevola* plant is selected from any one of the following species: *Scaevola acacioides, Scaevola* aemula, *Scaevola albida, Scaevola amblyanthera, Scaevola anchusifolia, Scaevola angulata, Scaevola angustata, Scaevola archeriana, Scaevola argentea, Scaevola auriculata, Scaevola* balansae, *Scaevola ballajupensis, Scaevola basedowii, Scaevola beckii, Scaevola brookeana, Scaevola browniana, Scaevola bursariifolia, Scaevola calendulacea, Scaevola calliptera, Scaevola* canescens, *Scaevola chamissoniana, Scaevola chanii, Scaevola chrysopogon, Scaevola* coccinea, *Scaevola collaris, Scaevola* collina, *Scaevola coriacea, Scaevola* crassifolia, *Scaevola cuneiformis, Scaevola cunninghanii, Scaevola* cylindrica, *Scaevola densifolia, Scaevola enantophylla, Scaevola eneabba, Scaevola* floribunda, *Scaevola gaudichaudiana, Scaevola* gaudichaudii, *Scaevola* glabra, *Scaevola* glabrata, *Scaevola* glandulifera, *Scaevola* globosa, *Scaevola* globulifera, *Scaevola* glutinosa, *Scaevola gracilis, Scaevola* graminea, *Scaevola hainanensis, Scaevola hamiltonii, Scaevola hobdyi, Scaevola hookeri, Scaevola humifusa, Scaevola humilis, Scaevola kallophylla, Scaevola kilaueae, Scaevola laciniata, Scaevola lanceolata, Scaevola linearis, Scaevola macrophylla, Scaevola macrostachya, Scaevola microphylla, Scaevola micrantha, Scaevola mollis, Scaevola montana, Scaevola muluensis, Scaevola myrtifolia, Scaevola nitida, Scaevola nubigena, Scaevola obovata, Scaevola oldfleldii, Scaevola oppositifolia, Scaevola ovalifolia, Scaevola oxyclona, Scaevola paludosa, Scaevola parvibarbata, Scaevola* parviflora, *Scaevola parvifolia, Scaeiola phlebopetala, Scaeiola pilosa, Scaevola platyphylla, Scaevola plumieri, Scaevola porocarva, Scaevola* procera, *Scaevola pulchella, Scaevola pulvinaris, Scaevola* ramosissima, *Scaevola repens, Scaevola restiacea, Scaevola* revoluta, *Scaevola sericophylla, Scaevola socotraensis, Scaevola* spicigera, *Scaevola spinescens, Scaevola striata, Scaevola subcapitata, Scaevola taccada, Scaevola tahitensis, Scaevola* tenuifolia, *Scaevola thesioides, Scaevola* tomentosa, *Scaevola tortuosa, Scaevola verticillata, Scaevola virgata, Scaevola wrightii*. In a further embodiment the *Scaevola* plant is from the *Scaevola aemula* species. In a further embodiment the *Scaevola* plant is a hybrid of any of the above species.

Cultivating *Scaevola* and Tissue Culture of Plants

Methods of *Scaevola aemula* pollination and seed germination are well known in the art (Sweeney, K 1999. Application of in vitro breeding techniques for the improvement of the Australian native fan flower, *Scaevola*. Masters' thesis, University of Melbourne; Howell, G. J. 1995. Reproductive biology and horticultural development of *Scaevola*. PhD thesis University of Melbourne; Luo, S, 2005. Genetic variation and interspecific hybridisation in the genus *Scaevola*. PhD thesis, University of Sydney, p69 and p72), *Scaevola aemula* plans can be easily grown (*Scaevola*. Hamrick, D (Ed), 2003 Ball red Book, Volume 2, Ball Publishing), are amenable to tissue culture (Wong, C. E. and Bhalla, P. L. 2010. Chapter 22, In vitro propagation of Australian native ornamental plant *Scaevola*, In: Jain S. M. and Ochatt. S. J. Protocols for In vitro propagation of ornamental plants, Methods in Molecular Biology vol. 589), and the methods for their growth, care, propagation and production are well known in the literature and current state of the art. Such information is readily available on breeder websites (e.g. www[dot]suntoryflowers[dot]com, www[dot]danzigeronline[dot]com, www[dot]syngentaflowers[dot]eu).

Control Plant/s

One skilled in the art will know what constitutes a suitable control plant. Suitable control plants are of the same species or variety as the "test" *Scaevola* plants. Suitable control plants include *Scaevola* plants of the same age or developmental stage as the test plant. Suitable plants may be selected from wild-type plants, plants that have not been genetically manipulated according to the invention, plants that have not been gene-edited according to the invention, plants that have been transformed with a control construct, plants that have been transformed with an empty vector construct, plants that have not been mutated according to the invention, and plants that do not contain the FUSED allele.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polypeptides and polypeptides possess biological activities that are the same or similar to those of the inventive polypeptides or polypeptides. The term "variant" with reference to polypeptides and polypeptides encompasses all forms of polypeptides and polypeptides as defined herein.

Protein Variants—Percent Identity

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from the NCBI website on the World Wide Web at ftp[dot]ncbi[dot]nih[dot]gov/blast/. The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at http://www[dot]ebi[dot]ac[dot]uk/emboss/align/) and GAP (Huang, X. (1994) On Global Sequence Alignment. Computer Applications in the Biosciences 10, 227-235.) as discussed above are also suitable global sequence alignment programs for calculating polypeptide sequence identity.

A preferred method for calculating polypeptide % sequence identity is based on aligning sequences to be compared using Clustal X (Jeanmougin et al., 1998, Trends Biochem. Sci. 23, 403-5.)

DNA Variants—Percent Identity

The term "variant" with reference to polynucleotides encompasses naturally occurring, recombinantly and synthetically produced polynucleotides. Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequence of the present invention. Identity is found over a comparison window of at least 20 nucleotide positions, preferably at least 50 nucleotide positions, more preferably at least 100 nucleotide positions, and most preferably over the entire length of a polynucleotide of the invention.

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatusova, T. and Madden, T. 1999. Blast 2 sequences, a new tool for comparing protein and nucleotide sequences, Federation of European Microbiological Societies, Microbiological Letters 174(2):247-250), which is publicly available from the NCBI website on the World Wide Web at ftp[dot]ncbi[dot]nih[dot]gov/blast/. The default parameters can be used.

Polynucleotide sequence identity may also be calculated over the entire length of the overlap between a candidate and subject polynucleotide sequences using global sequence alignment programs (e.g. Needleman, S. and Wunsch, C. 1970. A general method applicable to the search for similarities in the amino acid sequence of two proteins. Journal of Molecular Biology 48(3), 443-453). A full implementation of the Needleman-Wunsch global alignment algorithm is found in the needle program in the EMBOSS package (Rice, P. Longden, I. and Bleasby, A. 2000. EMBOSS: The European Molecular Biology Open Software Suite, Trends in Genetics, 16(6): 276-277) which can be obtained from the world wide web at www[dot]hgmp[dot]mrc[dot]ac[dot]uk/Software/EMBOSS/. The European Bioinformatics Institute server also provides the facility to perform EMBOSS-needle global alignments between two sequences on-line at www[dot]ebi[dot]ac[dot]uk/emboss/align/.

Alternatively, the GAP program may be used which computes an optimal global alignment of two sequences without penalizing terminal gaps. GAP is described in the following paper: Huang, X., 1994. On Global Sequence Alignment. Bioinformatics 10(3): 227-235.

A preferred method for calculating polynucleotide % sequence identity is based on aligning sequences to be compared using Clustal X (Jeanmougin, F, Thompson, J, Gouy, M, Higgins, D and Gibson, T. 1998. Multiple sequence alignment with Clustal X. Trends in Biochemical Sciences 23(10): 403-405.)

Polynucleotide Variants—Hybridisation

Alternatively, variant polynucleotides of the present invention, or used in the methods of the invention, hybridize to the specified polynucleotide sequences, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook, J. 1989. Molecular Cloning: A Laboratory Manual. 2nd Edition, Cold Spring Harbor Laboratory Press; Ausubel, F, Brent, R, Kingston, R, Moore, D, Seidman, J, Smith, J, Struhl, K (Eds). 1987. Current Protocols in Molecular Biology, Greene Publishing). Tm for polynucleotide molecules greater than about 100 bases can be calculated by the formula Tm=81.5+0.41% (G+C−log (Na+). (Sambrook 1989; Bolton, E and McCarthy, B, 1962. A general method for the isolation of RNA complementary to DNA. Proceedings of the National Academy of Science, USA 48(8):1390-1397). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

Definitions

In the description and tables that follow, numerous terms are used. To provide a clear and consistent understanding of the specification and claims, including the scope to be given such terms, the following definitions are provided:

Accession. As used herein, accession is a term used to describe proprietary individual unique plant genotypes (varieties) which have not been commercialized.

Actinomorohic. As used herein, actinomorphic is a term used to describe a radially symmetrical flower, with multiple symmetry planes.

Allele. As used herein, the term allele means any of one or more alternative forms of a gene.

Asexual propagation/Asexual reproduction. As used herein, the term asexual propagation or asexual reproduction means every type of plant propagation except for sexually produced seeds. Examples of asexual propagation include, but are not limited to, cuttings, grafting, division, apomixis, or regeneration in tissue culture.

Backcrossing. As used herein, backcrossing is a process in which a breeder repeatedly crosses hybrid progeny back to one of the parents, for example, a first-generation hybrid $F_1$ with one of the parental genotypes of the $F_1$ hybrid.

Cell. As used herein, cell includes a plant cell, whether isolated, in tissue culture, or incorporated in a plant or plant part.

Crossing. As used herein, the term crossing means the pollination of a female flower of a plant, thereby potentially resulting in the production of seed from the flower.

Cross-pollination. As used herein, the term cross-pollination means the fertilization by the union of two gametes from different plants.

Cutting. As used herein, the term cutting means a part originating from a plant, such as a stem, leaf, or root, removed from a plant to propagate a new plant, as through rooting or grafting.

Dominant inheritance. As used herein, the term dominant inheritance refers to a mode of inheritance in which the phenotype of a certain characteristic or trait is determined by a dominant allele.

$F_2$. As used herein, the "$F_2$" symbol denotes the offspring resulting from the self-pollination or sib-mating of members of the first generation, the F, generation.

Gamete. As used herein, the term gamete means a cell or nucleus that may participate in sexual fusion to form a zygote.

Gene. As used herein, gene refers to a segment of endogenous genomic DNA, including regulatory elements such as promoters and terminators.

Genetic transformation. As used herein, genetic transformation refers the process of incorporating a polynucleotide into a plant to make a genetically modified organism.

Genetically Modified Organism (GMO). As used herein, a GMO is an organism which has been genetically modified via genetic transformation.

Heterozygous. As used herein, heterozygous refers to a genetic constitution in which the corresponding alleles of a certain gene locus are different.

Homozygous. As used herein, homozygous refers to a genetic constitution in which the corresponding alleles of a certain gene locus are identical.

Inbreeding. As used herein, the term inbreeding refers to the production of offspring by the fusion of genetically closely related gametes.

Inflorescence. As used herein, the term inflorescence refers to a flower.

Locus. As used herein, the term locus is the position or location of a gene on a chromosome.

Molecular marker. As used herein, the term molecular marker refers to DNA sequence(s) and/or segment(s) that are closely linked to a gene locus and/or morphological or other characters of a plant, whereby those segments can be detected and visualized by molecular techniques.

Monogenic inheritance. As used herein, the term monogenic inheritance refers to a mode of inheritance in which the phenotype of a certain characteristic or trait is determined by a single gene.

Mutant allele. As used herein, the term mutant allele refers to an allele resulting from the act of mutation.

Mutation. As used herein, mutations are changes in the DNA sequence of a cell's genome and are caused by mutagens, such as radiation or chemicals, as well as by errors that occur spontaneously during DNA replication.

Normal flower. As used herein the terms 'normal', 'typical', 'regular', 'standard', 'usual', 'hand shaped', 'fan shaped', 'wild-type' and 'conventional' flower and flowers are used interchangeably and refer to *Scaevola* wild-type plants and commercially available varieties, all possessing a dorsal slit.

Outbreeding. Also known as outcrossing, is described herein as the production of offspring by the fusion of distantly related gametes. Outbreeding is the opposite of inbreeding.

Peloric plant. As used herein, the term peloric plant means a rare plant possessing radial floral symmetry that arises within a species that usually possesses bilateral symmetry.

Phenotype. The term phenotype refers to any observable characteristic or trait of a plant, such as flower colour, flower form, plant size, etc.

Plant. As used herein, the term plant includes reference to an immature or mature whole plant, including a plant from which seed or anthers have been removed. Seed or embryo that will produce the plant is also considered to be the plant.

Plant cell. Plant cell, as used herein includes plant cells whether isolated, in tissue culture, or incorporated in a plant or plant part.

Plant hormone composition. As used herein, a plant hormone composition refers to a chemical that regulates plant growth. For example, Indole-3-butyric acid, $N^6$-benzyl adenine, and gibberellic acid.

Plant part. As used herein, the term "plant part" includes protoplasts, leaves, stems, roots, root tips, anthers, pistils, seed, embryo, pollen, ovules, cotyledon, hypocotyl, shoot, tissue, petiole, cells and meristematic cells, and the like.

Pollination. As used herein, the term pollination is the process by which pollen is transferred in plants, thereby enabling fertilization and sexual reproduction.

Polynucleotide. The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

Polynucleotide fragment. A "fragment" of a polynucleotide sequence described herein is a subsequence of contiguous nucleotides.

Preferably the fragment is at least 5, more preferably at least 6, more preferably at least. 7, more preferably at least 8, more preferably at least 9, more preferably at least 10, more preferably at least 11, more preferably at least 12, more preferably at least 13, more preferably at least 14, more preferably at least 15, more preferably at least 16, more preferably at least 17, more preferably at least. 18, more preferably at least 19, more preferably at least 20, more preferably at least 21, more preferably at least 22, more preferably at least 23, more preferably at least 24, more preferably at least 25, more preferably at least 26, more preferably at least 27, more preferably at least 28, more preferably at least 29, more preferably at least 30, more preferably at least 35, more preferably at least 40, more preferably at least 45, more preferably at least 50 nucleotides in length.

Probe. The term "probe" refers to a short polynucleotide that is used to detect a polynucleotide sequence that is complementary to the probe, in a hybridization-based assay. The probe may consist of a "fragment" of a polynucleotide as defined herein. The probe may additionally include a label for detection of the probe. Suitable labels are known to those skilled in the art.

Primer. The term "primer" refers to a short polynucleotide, usually having a free 3OH group, that is hybridized to a template and used for priming polymerization of a polynucleotide complementary to the target. The primer may consist of a "fragment" of a polynucleotide as defined herein. The primer may additionally include a label for detection of the primer. Suitable labels are known to those skilled in the art.

Progeny. As used herein, progeny includes an $F_1$ *Scaevola* plant produced from the cross of two *Scaevola aemula* plants. Progeny further includes, but is not limited to, subsequent $F_2$, $F_3$, $F_4$, $F_5$, $F_6$, $F_7$, $F_8$, $F_9$, and so on generational crosses with the parents, between the progeny or from crosses with unrelated *Scaevola* plants.

Recessive inheritance. As used herein, recessive inheritance refers to a mode of inheritance in which the phenotype of a certain characteristic or trait is determined by a recessive allele.

Recessive mutation. As used herein, the phenotype of a recessive mutation is visible only in a homozygous genotype.

Self-pollination. As used herein, the term self-pollination refers to the method of collecting pollen from a plant and applying that pollen to a stigma of the same plant.

Sexual propagation/Sexual reproduction. As used herein, the term sexual propagation/sexual reproduction refers to the propagation of plants from seeds.

Somatic cell. As used herein, the term somatic cell is any cell of a plant other than the spores, gametes, or their precursors.

Stop codon. There are 3 STOP codons in the genetic code—TAG, TAA and TGA. The corresponding codons in mRNA are UAG, UAA, and UGA. These codons signal the end of the polypeptide chain during translation. These codons are also known as nonsense codons or termination codons as they do not code for an amino acid. In one embodiment the stop codon according to the present invention is TAA, which can be used interchangeable with the RNA stop codon UAA.

TCP domain. As used herein, the term TCP domain refers to a relatively conserved DNA sequence in plants coding for transcription factors (activation and repression) involved in multiple developmental processes, mainly related to cell development and growth i.e. the TEOSINTE BRANCHED I (*Zea mays*), CYCLOIDEA (*Antirrhinum majus*), PROLIFERATING CELL FACTOR 1 AND 2 (*Oryza sativa*) proteins=TCP. (Danisman, S, 2016. TCP transcription factors at the interface between environmental challenges and the plants growth responses. Frontiers in Plant Sciences, Vol 7, p1-13; Fambrini, M, Salvini, M and Pugliesi, C. 2014. Transposon-dependent induction of Vincent van Gogh's sunflowers: Exceptions revealed, Genesis 52:315-327).

Variety. As used herein, the term plant variety as used by one skilled in the art of plant breeding means a plant grouping within a single botanical taxon of the lowest known rank which can be defined by the expression of the characteristics resulting from a given genotype or combination of genotypes, distinguished from any other plant grouping by the expression of at least one of the said characteristics and considered as a unit with regard to its suitability for being propagated unchanged (As defined in: International convention for the protection of new varieties of plants, Chapter 1, Article 1 (vi) www[dot]upov[dot]int/upovlex/en/conventions/1991/act1991[dot]html #_i). A plant variety is commercialised and not proprietary (the term 'accession' is used to denote varieties that are not commercialised).

Zyomorphic. As used herein, the term zygomorphic means a bilaterally symmetrical flower, possessing a single plane of symmetry.

General Molecular Biology and Plant Molecular Biology Methods

Methods for Isolating or Producing Polynucleotides

The polynucleotide molecules of the invention can be isolated by using a variety of techniques known to those of ordinary skill in the art. By way of example, such polypeptides can be isolated through use of the polymerase chain reaction (PCR) described in Mullis, K, Francois, F and Gibbs, R (Eds). 1994. The Polymerase Chain Reaction, Birkhauser, incorporated herein by reference. The polypeptides of the invention can be amplified using primers, as defined herein, derived from the polynucleotide sequences of the invention.

Further methods for isolating polynucleotides of the invention include use of all, or portions of, the polypeptides having the sequence set forth herein as hybridization probes. The technique of hybridizing labelled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5.0×SSC, 0.5% sodium dodecyl sulfate, 1×Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1×SSC, 1% (w/v) sodium dodecyl sulfate, at 60° C.

The polynucleotide fragments of the invention may be produced by techniques well-known in the art such as restriction endonuclease digestion, oligonucleotide synthesis and PCR amplification.

A partial polynucleotide sequence may be used, in methods well-known in the art to identify the corresponding full-length polynucleotide sequence. Such methods include PCR-based methods, 5'RACE (Frohman MA, 1995, Rapid amplification of complimentary DNA ends for generation of full length complementary DNAs: Thermal RACE. In: Recombinant DNA Methodology—Selected Methods in Enzymology p655-671, Academic Press) and hybridization-based method, computer/database-based methods. Further, by way of example, inverse PCR permits acquisition of unknown sequences, flanking the polynucleotide sequences disclosed herein, starting with primers based on a known region (Triglia et al., 1998, A procedure for in vitro amplification of DNA segments that lie outside the boundaries of known sequences. Nucleic Acids Research 16(0.16), 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., 1989).

Methods for Identifying Variants

Physical Methods

Variant polypeptides may be identified using PCR-based methods (Mullis et al., 1994). Typically, the polynucleotide sequence of a primer, useful to amplify variants of polynucleotide molecules of the invention by PCR, may be based on a sequence encoding a conserved region of the corresponding amino acid sequence.

Alternatively, library screening methods, well known to those skilled in the art, may be employed (Sambrook et al., 1989). When identifying variants of the probe sequence, hybridization and/or wash stringency will typically be reduced relatively to when exact sequence matches are sought.

Polypeptide variants may also be identified by physical methods, for example by screening expression libraries using antibodies raised against polypeptides of the invention (Sambrook et al., 1989) or by identifying polypeptides from natural sources with the aid of such antibodies.

Computer-Based Methods

The variant sequences of the invention, including both polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Baxevanis, A 2001. The molecular biology database collection: an updated compilation of biological database resources. Nucleic Acids Research 29(1): 1-10; Wheeler, D, Church, D, Lash, A, Leipe, D, Madden, T 2001. Database resources of the National Centre for Biotechnology Information. Nucleic Acids Research 29(1): 11-16. for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from (ftp[dot]ncbi[dot]nih[dot]gov/blast/) or from the National Center for Biotechnology Information (NCBI), National Library of Medicine, Building 38A, Room 8N805, Bethesda, MD 20894 USA. The NCBI server also provides the facility to use the programs to screen other publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul, S., Madden, T., Schaffer, A., Zhang, J., Zhang, Z., Miller, W. and Lipman, D. 1997. Gapped BLAST and PSI-BLAST: a new generation of protein database search programs. Nucleic Acids Research 25(17): 3389-3402.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J., Higgins, D., and Gibson, T., 1994. CLUSTALW: improving the sensitivity of progressive multiple sequence alignment through sequence weighting, positions-specific gap penalties and weight matrix choice. Nucleic Acids Research, 22: 4673-4680,) or T-COFFEE (Notredame, C., Higgins, G., and Heringa, J., 2000. T-COFFEE: A novel method for fast and accurate multiple sequence alignment, Journal of Molecular Biology 302: 205-217) or PILEUP, which uses progressive, pairwise alignments (Feng, D and Doolittle, R. 1987. Progressive sequence alignment as prerequisite to correct phylogenetic trees Journal of Molecular Evolution 25, p351-360).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch, A and Bucher, P. 1994. PROSITE: recent developments. Nucleic Acids Research 22(17): 3583-3589; Hofmann, K., Bucher, P., Falquet, L., and Bairoch, A. 1999. The PROSITE database its status in 1999. Nucleic Acids Research 27(1): 215-219) is a method of identifying the functions of uncharacterized proteins translated from genomic or cDNA sequences. The PROSITE database (www[dot]expasy[dot]org/prosite) contains biologically significant patterns and profiles and is designed so that it can be used with appropriate computational tools to assign a new sequence to a known family of proteins or to determine which known domain(s) are present in the sequence (Falquet, L., Pagni, M., Bucher, P., Hulo, N., Sigrist, J., Hofmann, K and Bairoch, A. 2002. The PROSITE database, its status in 2002 Nucleic Acids Research 30(1): 235-238). Prosearch is a tool that can search SWISS-PROT and EMBL databases with a given sequence pattern or signature.

Methods for Isolating Polypeptides

The polypeptides of the invention, or used in the methods of the invention, including variant polypeptides, may be prepared using peptide synthesis methods well known in the art such as direct peptide synthesis using solid phase techniques (e.g. Stewart, J and Young, J. 1969. Thesis, Solid-Phase Peptide Synthesis, WH Freeman Co, San Francisco California, or automated synthesis, for example using an Applied Biosystems 431A Peptide Synthesizer (Foster City, California). Mutated forms of the polypeptides may also be produced during such syntheses.

The polypeptides and variant polypeptides of the invention, or used in the methods of the invention, may also be purified from natural sources using a variety of techniques that are well known in the art (e.g. Deutscher, M. (Ed) 1990. Methods in Enzymology, Vol. 182, Guide to Protein Purification,).

Alternatively, the polypeptides and variant polypeptides of the invention, or used in the methods of the invention, may be expressed recombinantly in suitable host cells and separated from the cells as discussed below.

Methods for Producing Constructs and Vectors

The genetic constructs of the present invention comprise one or more polynucleotide sequences of the invention and/or polynucleotides encoding polypeptides of the invention, and may be useful for transforming, for example, bacterial, fungal, insect, mammalian or plant organisms. The genetic constructs of the invention are intended to include expression constructs as herein defined.

Methods for producing and using genetic constructs and vectors are well known in the art and are described generally in Sambrook et al., 1989; Ausubel et al., Current Protocols in Molecular Biology, Greene Publishing, 1987).

Methods for Producing Plant Cells and Plants Comprising Constructs and Vectors

The invention further provides plant cells which comprise a genetic construct of the invention, and plant cells modified to alter expression of a polynucleotide or polypeptide of the invention or used in the methods of the invention. Plants comprising such cells also form an aspect of the invention.

Methods for transforming plant cells, plants and portions thereof with polypeptides are described in Draper, J., Scott, R., Armitage, P. and Walden, R. 1988. Plant Genetic Transformation and Gene Expression. A Laboratory Manual. Blackwell Scientific Publishers Oxford; Potrykus. I. and Spangenburg, G. 1995. Gene Transfer to Plants. Springer-Verlag, Berlin; and Gelvin, S., Schilperoort, R. 2000. Plant Molecular Biology Manual Kluwer Academic Publishers, Dordrecht. A review of transgenic plants, including transformation techniques, is provided in Galun and Breiman, 1997, Transgenic Plants. Imperial College Press, London.

Methods for Genetic Manipulation of Plants

Several plant transformation strategies are available (e.g. Birch, 1997, Ann Rev Plant Phys Plant Mol Biol, 48, 297; Hellens et al., 2000, Plant Mol Biol 42: 819-32; Hellens et al., Plant Meth 1: 13). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed. Such strategies are known as gene silencing strategies.

Genetic constructs for expression of genes in transgenic plants typically include promoters for driving the expression of one or more cloned polynucleotide(s), terminators and selectable marker sequences to detect presence of the genetic construct in the transformed plant.

The promoters suitable for use in the constructs of this invention are functional in a cell, tissue or organ of a monocot or dicot plant and include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest, or promoters which are derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter and the Ubi 1 promoter from maize. Plant promoters which are active in specific tissues respond to internal developmental signals or external abiotic or biotic stresses are described in the scientific literature. Exemplary promoters are described, for example, in WO02/00894 and WO2011/053169, which are herein incorporated by reference.

Exemplary terminators that are commonly used in plant transformation genetic constructs include, e.g., the cauliflower mosaic virus (CaMV) 35S terminator, the *Agrobacterium tumefaciens* nopaline synthase or octopine synthase terminators, the *Zea mays* zein gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Methods for Reducing or Eliminating Gene/Protein Expression or Activity in Plants Gene Silencing Transformation strategies may be designed to reduce expression of a polynucleotide/polypeptide in a plant cell, tissue, organ or at a particular developmental stage which/when it is normally expressed. Such strategies are known as gene silencing strategies.

Gene silencing strategies may be focused on the gene itself or regulatory elements which effect expression of the encoded polypeptide. "Regulatory elements" is used here in the widest possible sense and includes other genes which interact with the gene of interest. Preferably the regulatory elements are part of the gene.

Genetic constructs designed to decrease or silence the expression of a polynucleotide/polypeptide of the invention may include an antisense copy of a polynucleotide of the invention. In such constructs, the polynucleotide is placed in an antisense orientation with respect to the promoter and terminator.

An "antisense" polynucleotide is obtained by inverting a polynucleotide or a segment of the polynucleotide so that the transcript produced will he complementary to the mRNA transcript of the gene, e.g..

```
5' GATCTA 3' (coding strand)

3' CTAGAT 5' (antisense strand)

3' CUAGAU 5' (mRNA)

5' GAUCUA 3' (antisense RNA)
```

Genetic constructs designed for gene silencing may also include an inverted repeat. An 'inverted repeat' is a sequence that is repeated where the second half of the repeat is in the complementary strand, e.g.

```
5'-GATCTA...TAGATC-3'

3'-CTAGAT...ATCTAG-5'
```

The transcript formed may undergo complementary base pairing to form a hairpin structure. Usually, a spacer of at least 3-5 bp between the repeated region is required to allow hairpin formation. Constructs including such invented repeat sequences may be used in RNA interference (RNAi) and therefore can be referred to as RNAi constructs.

Another silencing approach involves the use of a small antisense RNA targeted to the transcript equivalent to an miRNA (Llave, C., Xie, Z., Kasschau, K and Carrington, J. 2002. Cleavage of Scarecrow-like mRNA targets directed by a class of *Arabidopsis* miRNA. Science 297(5589): 2053-2056). Use of such small antisense RNA corresponding to polynucleotide of the invention is expressly contemplated.

The term genetic construct as used herein also includes small antisense RNAs and other such polypeptides effecting gene silencing.

Transformation with an expression construct, as herein defined, may also result in gene silencing through a process known as sense suppression (e.g. Napoli, C., Lemieux, C and Jorgensen, R. 1990. Introduction of a chimeric chalcone synthase gene into *petunia* results in reversible co-suppression of homologous genes in trans. The Plant Cell 2: 279-289;). In some cases, sense suppression may involve over-expression of the whole or a partial coding sequence but may also involve expression of non-coding region of the gene, such as an intron or a 5' or 3' untranslated region (UTR). Chimeric partial sense constructs can be used to coordinately silence multiple genes (Abbott, J., Barakate, A., Pincon, G., Legrand, M., Lapierre, C., Mila, I., Schuch. W. and Halpin, C. 2002. Simultaneous suppression of multiple genes by single transgenes. Down-regulation of three unrelated lignin biosynthetic genes in tobacco. Plant Physiology 128(3): 844-53; Jones, C., Scothern, G., Lycett, G. and Tucker, G. 1998. The effect of chimeric transgene architecture on co-ordinated gene silencing. Planta 204: 499-505). The use of such sense suppression strategies to silence the expression of a polynucleotide of the invention is also contemplated.

The polynucleotide inserts in genetic constructs designed for gene silencing may correspond to coding sequence and/or non-coding sequence, such as promoter and/or intron and/or 5' or 3' UTR sequence, of the corresponding gene.

Other gene silencing strategies include dominant negative approaches and the use of ribozyme constructs (McIntyre, C and Manners, J. 1996. Strategies for the suppression of peroxidase gene expression in tobacco. 1. Designing efficient ribozymes. Transgenic Research 5: 257-262).

Pre-transcriptional silencing may be brought about through mutation of the gene itself or its regulatory elements. Such mutations may include point mutations, frameshifts, insertions, deletions and substitutions.

Methods for Editing Endogenous Genomes of Plants

Some embodiments of the invention involve modifying the genomes of *Scaevola* plants to reduce or eliminate expression or activity of CYC2 genes and proteins and thereby produce the desired floral phenotype of the invention in the plants.

Methods for modifying endogenous genomic DNA sequences in plants are known to those skilled in the art. Such methods may involve the use of sequence-specific nucleases that generate targeted double-stranded DNA breaks in genes of interest. Examples of such methods for use in plants include: zinc finger nucleases (Curtin, S., Zhang, F., Sander, J., Haun, W., Starker, C., Baltes, N., Reyon, D., Dahlborg, E., Goodwin, M., Coffman, A., Dobbs, D., Joung, J., Voytas, D. and Stupar, R. 2011. Targeted mutagenesis of duplicated genes in soybean with zinc-finger nucleases. Plant Physiology 156: 466-473;), transcription activator-like effector nucleases or "TALENs" (Cermak, T. Doyle, E., Christian, M., Wang, L., Zhang, Y., Schmidt, C., Bailer, J., Somia, N. and Bogdanove, A. 2011. Efficient design and assembly of custom TALEN and other TAL effector-based constructs for DNA targeting. Nucleic Acids Research 39(12): e82; Mahfouz, M., Li, L., Shamumuzzaman, M., Wibowo, A., Fang, X and Zhu, J. 2011. De novo-engineered transcription activator-like effector (TALE) hybrid nuclease with novel DNA binding specificity creates double-strand breaks. Proceedings of the National Academy of Science USA 108(6): 2623-2628; Li, T., Spalding, M., Weeks, D and Yang, B. 2012. High efficiency TALEN-based gene editing produces disease-resistant rice. Nature Biotechnology 30: 390-392), and LAGLIDADG homing endonucleases, also termed "meganucleases" (Tzfira, T., Weinthal, D., Marton, I., Zeevi, V., Zuker, A. and Vainstein, A. 2012. Genome modifications in plant cells by custom-made restriction enzymes. Plant Biotechnology 10:373-389).

Targeted genome editing using engineered nucleases such as clustered, regularly interspaced, short palindromic repeat (CRISPR) technology, is an important new approach for generating RNA-guided nucleases, such as Cas9, with customizable specificities. Genome editing mediated by these nucleases has been used to rapidly, easily and efficiently modify endogenous genes in a wide variety of biomedically important cell types and in organisms that have traditionally been challenging to manipulate genetically. A modified version of the CRISPR-Cas9 system has been developed to recruit heterologous domains that can regulate endogenous gene expression or label specific genomic loci in living cells (Sander, J and Joung, J. 2014. CRISPR-Cas systems for editing, regulating and targeting genomes. Nature Biotechnology 32: 347-355. The system is applicable to plants and can be used to regulate expression of target genes. (Bortesi, L. and Fischer, R.2015. The CRISPR/Cas9 system for pant genome editing and beyond. Biotechnology Advances 33(1): 41-52).

In certain embodiments of the invention, a genome editing technology (e.g. TALENs, a Zinc finger nuclease or CRISPR-Cas9 technology) can be used to modify one or more base pairs in a target endogenous CYC2 to reduce or eliminate expression or activity of CYC2 genes and proteins and thereby produce the plants of the invention with the desired floral phenotype.

Methods for Regeneration of *Scaevola* Plants

Methods for regenerating *Scaevola* plants are known in the art and include for example those disclosed in:

Wang, Y. and Bhalla P. 2004. Somatic embryogenesis from leaf explants of Australian fan flower, *Scaevola aemula* R. Br. Plant Cell Reports 22: 408-414, and Bhalla, P. and Xu, H. 1999. Plant Regeneration from Callus of Australian Fan Flower, *Scaevola*. Journal of Plant Physiology, 154(3): 374-378.

Methods for Mutating the Genomes of Plants

Mutation breeding, sometimes referred to as "variation breeding", is the process of exposing plants, plant parts, reproductive material, seeds, cells, cuttings and the like to chemicals or radiation in order to generate mutants with desirable traits.

Different kinds of mutation breeding are well known to those skilled in the art and include approaches such as using chemical mutagens like ethyl methanesulfonate and dimethyl sulfate, radiation or transposons to generate mutants. Mutation breeding is commonly used to produce traits in crop and ornamental plants.

Such methods are described for example in: Shu, Q. Forster, B. and Nakagawa, H. (Eds) 2011. Plant mutation breeding and biotechnology, Joint FAO/IAEA Division of Nuclear Techniques in Food and Agriculture, International Atomic Energy Agency, Vienna Austria. Ceccarelli, S. E. Guimaraes, E. and Weltzien, E. (Eds). 2009. Plant breeding and farmer participation, Chapter 8. Methodologies for generating variability. Part 4: Mutation techniques., Publisher: Food and Agriculture Organization of the United Nations, Editors: pp. 159-194; and Sikora, P. et al, 2011, Mutagenesis as a Tool in Plant Genetics, Functional Genomics, and Breeding. Volume 2011 |Article ID 314829, International Journal of Plant Genomics.

Methods for Measuring Reduced or Eliminated Expression or Activity

Methods for reduced or eliminated expression of a plant gene or protein are well known to those skilled in the art and include but are not limited to nucleic acid based methods such as Northern analysis, RT-PCR and dot-blot analysis (Sambrook et al, 1989), and protein-based methods such as: ELISA (Kemeny, 1991. A Practical Guide to ELISA, NY Pergamon Press) and Western analysis (Towbin & Gordon, 1994, J Immunol Methods, 72, 313).

Seed Deposit

Seeds of the *Scaevola* accession 20-61 have been deposited at NCIMB Limited, Ferguson Building, Craibstone Estate, Bucksburn, Aberdeen AB21 9YA as follows:

| Depositors Identification reference | Depository accession number | Deposit date |
|---|---|---|
| *Scaevola aemula* 20-61 | NCIMB 43619 | 21 May 2020 |

The deposit receipt and viability statement are provided on the following pages.

The present invention describes a new mutant allele of *Scaevola aemula* designated "FUSED". The FUSED allele is phenotypically expressed in the flower resulting in a fused or partially fused floral tube, giving the phenotypic appearance of radial or near radial symmetry of the petals in the corolla. The present invention also relates to a *Scaevola* seed, plant and plant parts that possess the new FUSED allele. The present invention also relates to methods of transferring the FUSED allele to a wide range of different *Scaevola* genotypes, to develop novel radially symmetrical flowered plants.

The FUSED allele of the present invention can be introduced into any *Scaevola* plant. It can be readily transferred into any *Scaevola* plant lacking the allele. The allele and the methods herein described can be used to modify the inflorescence of any *Scaevola* plant.

One method involves hybridization via cross pollination using a parent possessing the FUSED allele as the pollen or ovule parent. Another method involves self-pollination of a plant possessing the FUSED allele.

The FUSED allele can be used to modify the appearance of the corolla of all *Scaevola* varieties for commercial production.

A plant of the present invention can be obtained by crossing a plant either heterozygous or homozygous for the claimed mutant allele with any *Scaevola* variety lacking the allele. Further breeding can then be performed to incorporate other genes of interest in a breeding program. Plants heterozygous for the FUSED allele can be positively selected for use to transfer the allele based on the phenotypic marker of early developing flowers expressing the radially symmetrical phenotype.

The new mutant allele can be introduced into varieties with other desirable genetic traits such as compact plant habit, trailing habit, upright habit, earliness to flower, drought tolerance, unique flower colours such as yellow, pink, white, blue and combinations thereof, resistance to pests and diseases, ease of propagation and any other character of interest, for example.

The present invention was developed as part of a mutation breeding program in which proprietary accessions were subjected to gamma radiation treatment. In accordance with the invention, the mutation could also be created by another mutagenic agent, or gene editing. Examples of other mutagenic agents include X-rays, ultra-violet radiation, ethyl methanesulfonate (EMS), methyl methanesulfonate (MMS), etc. Examples of gene editing systems include CRISPR/Cas9, ZFN and TALEN's (Mao, Y, Botella, J. R., Liu, Y and Zhu, J. 2019. Gene editing in plants: progress and challenges. National Science Review 6:421-437).

One of average skill in the art would therefore expect that other deletions or disruptions to the CYCLOIDEA2 gene in *Scaevola* could result in the same phenotypic expression of radial floral symmetry.

The *Scaevola* mutant FUSED allele of the present invention was transferred by cross-pollination into numerous genetically diverse *Scaevola aemula* lines. A series of *Scaevola aemula* plants containing the mutant allele was produced.

The FUSED allele, when expressed in the homozygous state results in the production of almost all flowers on a plant with a fused dorsal slit. In the heterozygous state the FUSED allele may be expressed phenotypically by a fused dorsal slit evident in the first few flowers, but subsequent flowers revert to the normal wild-type phenotype. The mutant FUSED allele is a recessive nonsense mutation (a single base change introducing a stop codon) within the CYCLOIDEA 2 coding region.

The applicants developed a CAPS marker system to reliably identify plants containing the mutant allele. The co-dominant CAPS marker correctly identified all plants possessing the FUSED allele in either a homozygous or heterozygous state.

Peloric plants are known in the art of horticulture, however, they are extremely rare. The underlying mechanism for the development of such plants varies immensely depending on the species. In *Scaevola aemula* peloric plants have never been reported, to the inventor's knowledge after extensive prior art searching.

In other plant species, peloric plants have been found, and in some cases involve either a loss of or increase in expression of CYCLOIDEA gene(s) (of which there are many), and often also involve other gene(s) or genetic mechanisms.

For example in *Antirrhinum*, a CYC and DICH gene were both disabled, resulting in peloric *Antirrhinum* plants, and in addition these plants possessed an extra petal, sepal and stamen (six of each in the mutant, 5 of each in wild-type plants) (Luo, D., Carpenter, R., Vincent, C., Copsey, L. and Coen, E. 1995. Origin of Floral Symmetry in *Antirrhinum*, Nature 383:794-799).

In the present *Scaevola* floral phenotype in accordance with the invention, there was no increase in the number of petals, sepals or stamens and mutation of one specific CYC gene (the CYC2 gene) was required (not two distinct genes) to develop radially symmetrical flowers. Thus, the prior art with respect to *Antirrhinum* would in no way lead an art skilled worker toward the present invention with respect to *Scaevola*.

Dong et al 2018 (Dong, Y., Liu, J., Li, P., Li, C., Lu, T., Yang, X. and Wang, Y. 2018. Evolution of Darwin's peloric *Gloxinia* (*Sinningia speciosa*) is caused by a null mutation in a pleiotropic TCP gene, Molecular Biology and Evolution 38(8): 1901-1915) suggested that 'the evolution of peloric *Gloxinia* involves a 2-fold mechanism. That is, the 10-bp deletion brings about loss of function of an SsCYC protein, which in turn, further disrupts the auto-regulatory loop of SsCYC leading to a complete loss of dorsal specific expression'. In their analysis, this mutation, besides causing peloric flowers, also changed the orientation of the flowers due to suppression of the gibbous structure at the base of the flowers. Furthermore, in *Gloxinia*, the flowers have no dorsal slit, thus again, the prior art with respect to *Antirrhinum* would in no way lead an art skilled worker toward the present invention with respect to *Scaevola*, in which fusion of the dorsal slit produces the radially symmetrical flowers, which was an unexpected and surprising result.

In African Violets (Hsu, H., He. C., Kuo, E., Hsin, K., Lu, J., Pan, Z. and Wang, C. 2018. Genetic analysis of floral symmetry transition in African Violet suggests the involvement of trans-acting factor for CYCLOIDEA expression shifts, Frontiers in Plant Science 9: 1-19) no CYC2 genes were found, only a variety of CYC1 gene families. The CYC2 gene of the present invention was not present in the plants examined in the African violet study of Hsu et al 2018.

In a wide ranging study in the pea family (Zhao, Z., Hu, J., Chen, S., Luo, Z., Luo, D., Wen, J., Tu, T., Zhang, D. 2019. Evolution of CYCLOIDEA-like genes in Fabales: Insights into duplication patterns and the control of floral symmetry, Molecular Phylogenetics and Evolution 132: 81-89) the authors proposed 'the diversification patterns of both CYC1 and CYC2 genes are not related to the floral symmetry in non-papilionoid Fabales groups, however, gene duplication and functional divergence of CYC2 are essential for the floral zygomorphy of Papilionoideae'. Further, (page 87) the authors mention 'many species of non-papilionoids have only a single copy of CYC2 genes despite their differences in symmetric forms, while some others with radial symmetric flowers have two copies, suggesting that the duplication events of CYC2 genes have not been associated with floral symmetry in those organisms'. This study indicated how difficult it is to pin-point exactly which gene(s) are responsible for floral symmetry (if any), and certain CYC2 genes in one part of a family can have a different effect in another part of a family.

In the legume *Cadia*, an unusual change from bilateral symmetry to radial symmetry was characterized by a change in expression pattern of a CYC gene. The expression pattern of one CYC gene expanded from the adaxial to the lateral and abaxial regions of the corolla, suggesting that the radial flowers of *Cadia* are dorsalized and thus a reversal to radial symmetry did not occur, but a homeotic transformation where all petals have acquired dorsal identity (Citeme, H., Pennington, R., Cronk, Q. 2006. An apparent reversal in floral symmetry in the legume *Cadia* is a homeotic transformation, Proceedings of the National Academy of Sciences of the United States of America, 103(32): 12017-12020). This unusual change in expression is a completely different mechanism leading to radial symmetry, to that found in accordance with the present invention.

In Sunflower (*Helianthus annuus*), Fambrini et al (Fambrini, M., Salvini, M., Basile, A., and Pugliesi, C. 2014. Transposon-dependent induction of Vincent van Gogh's sunflowers: Exceptions revealed, Genesis 52:315-327) investigated floral mutants possessing actinomorphic ray florets. Normal sunflowers have zygomorphic ray florets and actinomorphic disk florets. Molecular analysis of turf (tubular ray floret) mutant sunflowers identified the insertion of a nonautonomous transposable element (TE) in the TCP domain of the HaCYC2 gene, thereby changing the ray florets from bilateral symmetry to radial symmetry. Another mutant known as Chrvs is characterized by a shift from actinomorphic to zygomorphic-like corollas of disk flowers. A single semi-dominant major gene controls this trait and is due to a 999 bp insertion upstream of the start codon of a CYCLOIDEA-like gene (HaCYC2), within the promoter region. In the present invention there was no transposable element involved.

In Linaria, (Cubas, P., Vincent, C. and Coen, E., 1999. An epigenetic mutation responsible for natural variation in floral symmetry, Nature 40: 157-161) the authors demonstrated a change from bilateral to radial symmetry was due to extensive methylation of the LCYC gene, causing the gene to become transcriptionally silent. This method of change from bilateral to radial symmetry was once again different to what was found in the subject of the present invention, furthermore, the LCYC gene is not present in *Scaevola*.

As noted previously, the present invention is the first example of production of radially symmetrical flowers in *Scaevola*. Thus, there was no precedent to suggest that such flowers could be produced at all in *Scaevola*. Rather the applicant surprisingly produced *Scaevola* plants with the floral phenotype of the invention in their commercial breeding program.

Furthermore, given these several diverse range of mechanism involved in the change from bilateral to radial floral symmetry in the range of diverse plant families, and the unrelatedness of *Scaevola* to these species, one skilled in the art, could not have predicted a likely mechanism producing the radially symmetrical flower in *Scaevola*, as now provided by the present invention.

The new altered flower phenotype resulting from the FUSED allele causes the floral tube to become fused where there would normally be a dorsal slit located between the dorsal petals that extends from the edge of the corolla to the ovary. This floral tube fusion limits the ability of insects to enter and pollinate the flowers. Unexpectedly, when grown outdoors, plants with the altered phenotype show very low seed production originating from insect pollination compared to normal *Scaevola aemula* plants. Also, unexpectedly, this attribute surprisingly increases the length of flower presentation, because flowers are not able to be easily pollinated by insects. Normal *Scaevola aemula* flowers that are successfully pollinated abort their corolla within one day of pollination, *Scaevola aemula* plants with a longer shelf life and flower presentation are likely to be viewed favourably by the plant retailer and consumer due to the extended ornamental appeal, hence the plans developed from the present invention have improved commercial utility and novelty.

The applicants have further demonstrated that seed production by hand pollination in plants possessing the FUSED allele is successful and seeds are produced at similar volumes per cross pollination to cross pollinations between plants lacking the mutant allele.

The applicants have successfully produced thousands of seeds using *Scaevola* plants possessing the FUSED allele from cross, self and open pollination with numerous unrelated *Scaevola* genotypes.

The invention further provides methods for developing *Scaevola* plants in a plant breeding program using plant breeding techniques such as parental selection and hybrid development, recurrent selection, backcrossing, pedigree breeding, CAPS marker assisted selection, 59) transformation and gene editing. Seeds, *Scaevola aemula* plants, and plant parts thereby produced by such breeding methods are also part of the invention.

The invention also relates to methods for producing a *Scaevola* plant containing in its genetic material one or more transgenes and to the transgenic *Scaevola* plan produced by that method. Preferably the transgene is the mutant allele FUSED or cDNA of the mutant allele FUSED.

The present invention is directed in part to developing unique *Scaevola* plants. A transferable allele, designated FUSED, which conveys the altered flower phenotype characteristic has been isolated and incorporated into other genetic backgrounds. The allele of the instant invention has also been expressed in many different genetic backgrounds.

The new altered flowering *Scaevola* plants of the present invention are genetically stable as shown by the stability of the altered phenotype through successive rounds of asexual propagation and the transmission of the trait to progeny through a wide range of genetically diverse sexual crosses.

Prior to the present invention, the development of *Scaevola* plants with floral radial symmetry was not possible to obtain by methods obvious to one skilled in the art. This new trait can be reliably and predictably integrated into diverse genetic backgrounds of *Scaevola* to create new varieties, regardless of whether the male or female parent in a cross combination possesses the allele.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner. In some embodiments, the term "comprising" (and related terms such as "comprise and "comprises") can be replaced by "consisting of" (and related terms "consist" and "consists"). All publications cited in this application are herein incorporated by reference.

BRIEF DESCRIPTION OF THE FIGURES

The patent or application file contains at least one drawing executed in color. Copies of this patent or patent application publication with color drawings will be provided by the office upon request and payment of the necessary fee.

The following figures, which are incorporated herein and form part of the specification, illustrate come, but not the only or exclusive example embodiments and/or features and are to be considered illustrative and not limiting in scope.

FIG. 2 shows the fused dorsal slit characteristic of the present invention (left) compared to a normal flower (right) showing the dorsal slit extending from the edge of the corolla to the ovary.

FIG. 3 shows a mature plant example of the present invention homozygous for the FUSED allele (left) and a normal wild-type *Scaevola aemula* plant (right) possessing no FUSED alleles.

FIG. 4 shows range of flower colours and sizes of the present invention exhibiting radial floral symmetry, flower colours include blue, white, yellow, pink, pink and yellow combined and violet and yellow combined.

FIG. 14 shows an CLUSTAL O (1.2.4) multiple sequence alignment of CYC2 proteins from *Scaevola aemula* (SamCYC2—SEQ ID NO:1), *Scaevola taccada* (StaCYC2—SEQ ID NO:2), and *Scaevola sericea* (SseCYC2—SEQ ID NO:3). The position of *Scaevola* CYC2 motifs corresponding to motifs 1, 2 and 4 as described in Chen et al. 2018., is highlighted with grey shading. Motifs 1, 2 and 4 are present in all of the CYC2-like form Asterales, described by the authors of Chen et al., 2018.

FIG. 15 shows the % identity between the CYC2 proteins form *Scaevola aemula* (SamCYC2 SEQ ID NO: 1), *Scaevola taccada* (StaCYC2—SEQ ID NO:2), and *Scaevola sericea* (SseCYC2—SEQ ID NO:3) aligned in FIG. 14.

EXAMPLES

In addition to the exemplary aspects and embodiments described above, further aspects and embodiments will become apparent by study of the following non-limiting examples.

The following examples are provided to further illustrate the present invention. These examples are not to be construed as limiting the scope of the invention in any manner beyond the limitations set forth in the appended claims. Many variations and modifications may be made while remaining within the spirit and the scope of the invention.

Example 1. Development of the Original Mutant Radially Symmetrical Flowered Plant A commercially based *Scaevola aemula* breeding program was commenced in 1997 to produce novel varieties for the international ornamental horticulture market. From 1997 to 2013 approximately 27,486 seedlings were developed from various crosses and open pollinations originating from up to 67 wild-collected and commercially available cultivars. Seedlings were carefully screened for commercially viable traits. Radially symmetric flowers were never observed. As a result of crossing during 2013 that included gamma irradiated accessions, a first altered floral phenotype plant (accession 7952) was observed in a population of proprietary plants during 2014. However, this plant only possessed radially symmetric flowers for the first few flowers developed during the production period. Flowers that developed later exhibited the normal floral phenotype of *Scaevola aemula*. Further selection and crossing resulted in one completely stable radially symmetrical flowering plant selected in 2016. This plant was designated accession 11361. This accession uniformly and stably expressed the new radially symmetrical floral phenotype through repeated generations of asexual propagation and growth under a wide range of environmental conditions during all seasons of the year in Yellow Rock, NSW Australia and Higashiomi, Shiga, Japan.

Example 2. Self-Pollination of the Original Mutant Radially Symmetrical Flower Plant (Accession 11361)

*Scaevola aemula* plants are known in the art to be self-incompatible (Luo, 2005; Sweeney, 1999; Howell, 1995). However, it was suspected that the new *Scaevola aemula* accession 11361 could be self-compatible. Self-pollinations were performed by hand using a small paint brush in an insect screened greenhouse during summer at Yellow Rock, Australia, following published methods.

Figure 1:
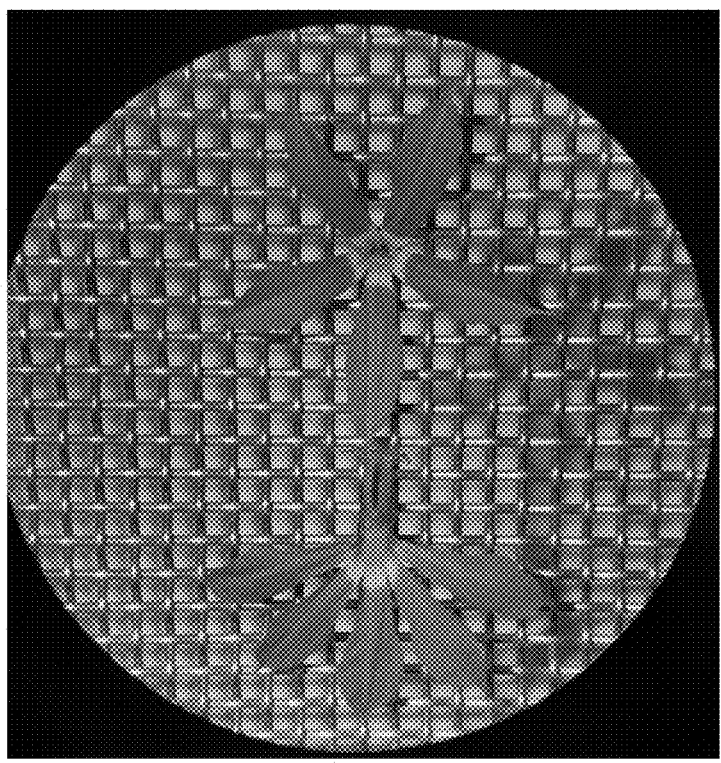
FIG. 1 shows the normal 'wild-type' fan flower morphology of *Scaevola aemula* (bottom) and the new 'radially symmetrical' flower morphology of the present invention (top), with dorsal, lateral and ventral petals labelled.
Figure 5:
FIG. 5 shows self-pollinated progeny from accession 11361, demonstrating the radially symmetrical flower trait is homozygous, with 100% of progeny exhibiting radial symmetry.

When the first original stable radially symmetrical flowered plant (accession 11361) was self-pollinated (100 manual hand self-pollinations using a small paint brush), unexpectedly, 69 seeds were produced. From these seeds 53 plants were developed and grown to flowering. All 53 plants possessed the radially symmetrical flower trait, on every flower of every plant indicating this line was homozygous for the radially symmetrical flower trait (FIG. 5). In addition, this experiment showed the white flower colour of this line is also a homozygous trait. Evidence of inbreeding depression (slow, weak growth and late flowering) was observed in the population. The maximum number of seeds that can be produced in a *Scaevola aemula* fruit is two, after self-pollinating the accession 11361, 34.5% seed set occurred (Table 1).

TABLE 1

Seed set following self-pollination and plants grown to flowering for accession 11361

| Accession | Flower phenotype | Self-pollinations performed | Seeds collected | Plants grown to flowering |
|---|---|---|---|---|
| 11361 | Radially symmetrical | 100 | 69 | 53 |

Example 3. Intercrossing Seven Radially Symmetrical Flowered Accessions to Assess the Transmission of the Radially Symmetrical Flower Trait Using the accession 11361, cross and open pollinations were performed among numerous accessions exhibiting normal flowers. The progeny from these crosses were also intercrossed directly or via open pollination. From this breeding work, seven accessions were selected that stably exhibited the symmetrical flower trait. Cross pollinations were performed by hand randomly between the seven accessions stably exhibiting the radially symmetrical flower trait. These seven lines were genetically diverse, possessing flower colours including: dark blue, pink, deep yellow, yellow, pink with eye, dark pink with eye and dark blue with eye. All seven lines were intercrossed using bulk pollen collected from all seven lines. 1367 pollinations were performed, 262 fruits were collected, 225 seeds were sown, resulting in 71 plants. Of these 71 plants, 54 reached the flowering stage (17 were weak and did not flower). The 54 plants reaching the flowering stage all exhibited the radially symmetrical flower trait. Various flower colours and combinations were revealed in the progeny. This work demonstrated that the radially symmetrical flower trait could be transferred between different genotypes of Scaevola aemula.

Figure 6:
FIG. 6 shows flowering progeny developed from intercrossing ten radially symmetrical flowering lines from Example 5, 100% possessing the radially symmetrical flower trait.

Example 4. Inter-Crossing Ten Radially Symmetrical Flowered Accessions to Assess the Transmission of the Radially Symmetrical Flower Trait Using ten different accessions to Example 3, cross pollinations were performed by hand randomly between the ten accessions stably exhibiting the radially symmetrical flower trait. These ten lines were genetically diverse, possessing flower colours including: yellow and blue bicolour, yellow and pink bicolour, blue and white centre, white, dark yellow and pink bicolour, blue and light blue. All ten lines were intercrossed using bulk pollen collected from all ten lines. Pollinations were performed, 621 fruits were collected, 692 seeds were sown, resulting in 421 plants reaching the flowering stage. All 421 plants reaching the flowering stage stably exhibited the radially symmetrical flower trait. Various flower colours and combinations were revealed in the progeny (FIG. 6). Examples 2, 3 and 4 demonstrated that the radially symmetrical flower trait was homozygous in plants stably exhibiting the trait.

Example 6. Determining the Genetic Mechanism of the Radially Symmetrical Flower Trait Recent floral morphological studies in the Goodeniaceae family (Berger et al. 2017, Gardner et al. 2016 and Han, 2018) suggest that members of the CYCLOIDEA-like genes are responsible for the variation in floral petal arrangement within this family. These genes are transcription factors, regulating the copying of DNA to RNA so that the correct gene expression occurs in the correct location of the plant at the correct time. Han explains that floral symmetry can be influenced by asymmetrical expression and duplication of these transcription factors. In Scaevola aemula, Han 2018 (p59-p62) found three copies of CYC: CYC1, CYC2 and CYC3, and within CYC3 there were two copies CYC3A and CYC3B. These different copies were expressed differentially in leaves, floral buds and lateral and/or ventral petals. Han found that the degree of bilateral symmetry exhibited by flowers in Scaevola aemula was influenced by subtle changes in the expression levels of multiple CYC-like genes (p67). Han remarked (referencing Howarth et al 2011 and Zhang et al 2013) that in radially symmetrical groups (of plants) CYC2 clade members are either not expressed in corolla tissue or are ubiquitously expressed (underscore added). This statement clearly shows the ambiguity surrounding CYC2 genes and the difficulty in predicting in advance the possible impact of extra copies and/or deletions.

Prior to this invention, it was not known what genetic mechanism (if any) could be responsible for radial floral symmetry in Scaevola aemula. In fact, radially symmetrical Scaevola aemula flowering plant(s) had not been reported in the available literature. As such, it can be appreciated by one of ordinary skill in the art, that at this time there may have been a multitude of possible causes for the radially symmetrical flower trait in Scaevola aemula. A range of ideas were considered, and experiments were conducted.

Experiments were undertaken to determine if CYCLOIDEA gene(s) were responsible for the novel morphology of the present invention, as it could not be predicted in advance the mechanism controlling the floral symmetry in accession 11361. Three proprietary accessions were selected for analysis (Table 2).

TABLE 2

Plant materials utilized for CYCLOIDEA genetic investigations

| Accession | Flower type |
| --- | --- |
| 7482 | Normal |
| 7952 | Initially radially symmetrical, changing to normal |
| 11361 | Radially symmetrical |

Experimental work involved cloning CYCLOIDEA 2 genes. Primers for amplifying Scaevola aemula CYCLOIDEA 2 (CYC2) genes were designed using the Scaevola taccada CYC2 sequence deposited in GenBank (accession number: MG593372.1). These primers (St-cycF1: TCCATGTCTGCCCTCCTTCT [SEQ ID NO: 27], and St-cycR1: TTACACGCATCACCCTGCTG [SEQ ID NO: 28]) produced about a 1 kb amplicon from accessions 7482, 7952 and 11361 cDNA. cDNA was produced with total RNA prepared from flower buds using ReverTra Ace reverse transcriptase (Toyobo). PCRs were carried out using Tks gflex DNA polymerase (Takara Bio) for 35 cycles of 15 seconds at 98° C., 20 seconds at 60° C., and 30 seconds at 68° C. These amplicons were cloned using TArget clone-plus-(Toyobo) and sequenced using a 3500 Genetic Analyzer (Applied Biosystems).

Figure 7:
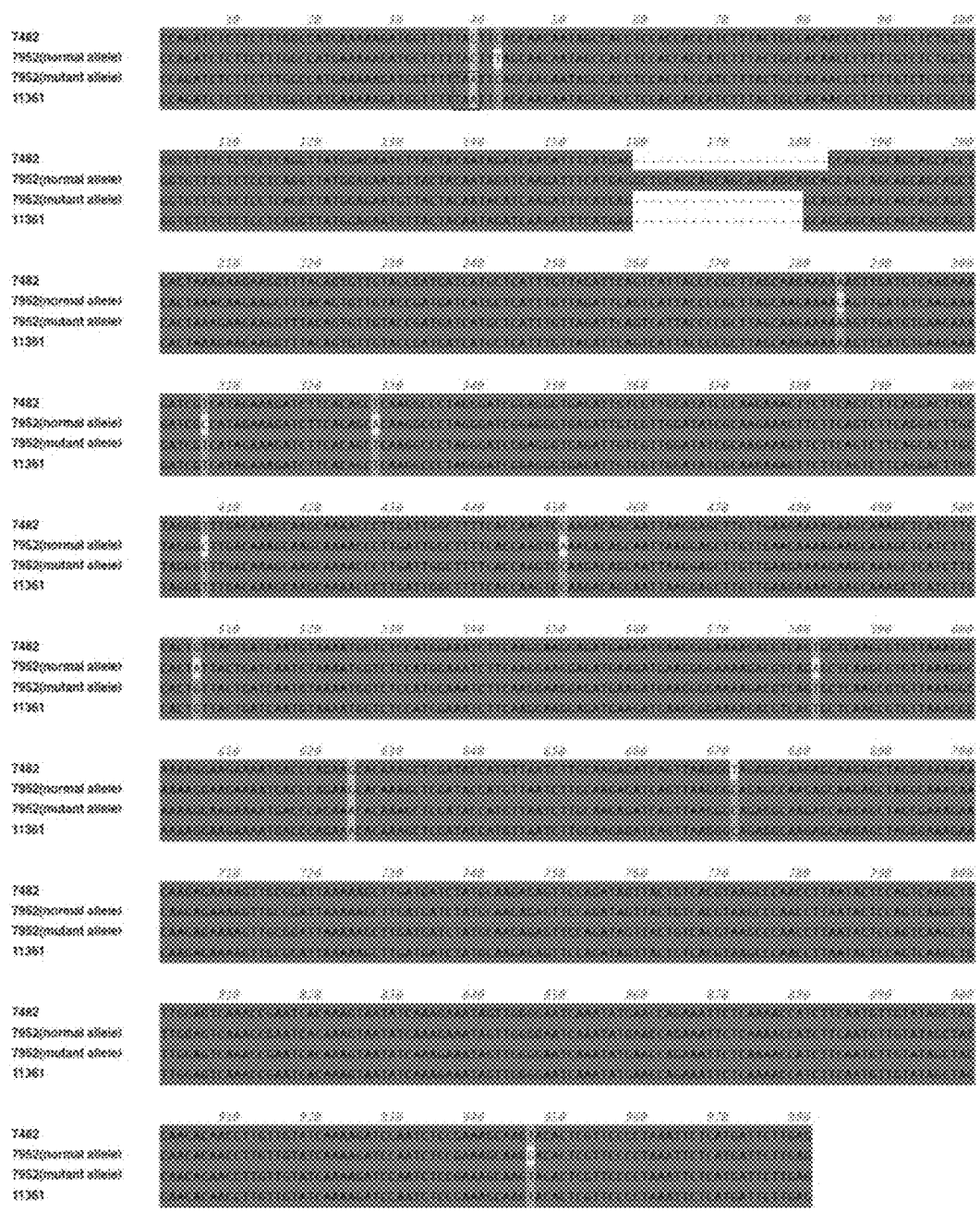
FIG. 7 shows the CYC2 cDNA sequences for accessions 7482 (SEQ ID NO:35), 7952 (wild-type allele; SEQ ID NO:36), 7952(mutant allele; SEQ ID NO:37), and 11361 (SEQ ID NO:38), showing single base TAA (Stop) codon mutation for radially symmetrical flowered 11361 and mutant allele of initially radially symmetrical then normal flowered 7952 (red box).
Figure 8:
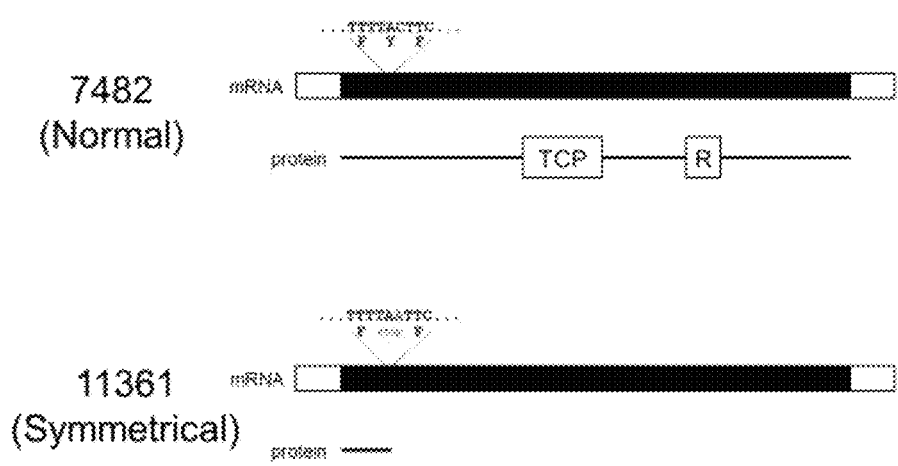
FIG. 8 shows a diagrammatic explanation of the mutation causing the radially symmetrical flower form in accession 11361.
Figure 9:
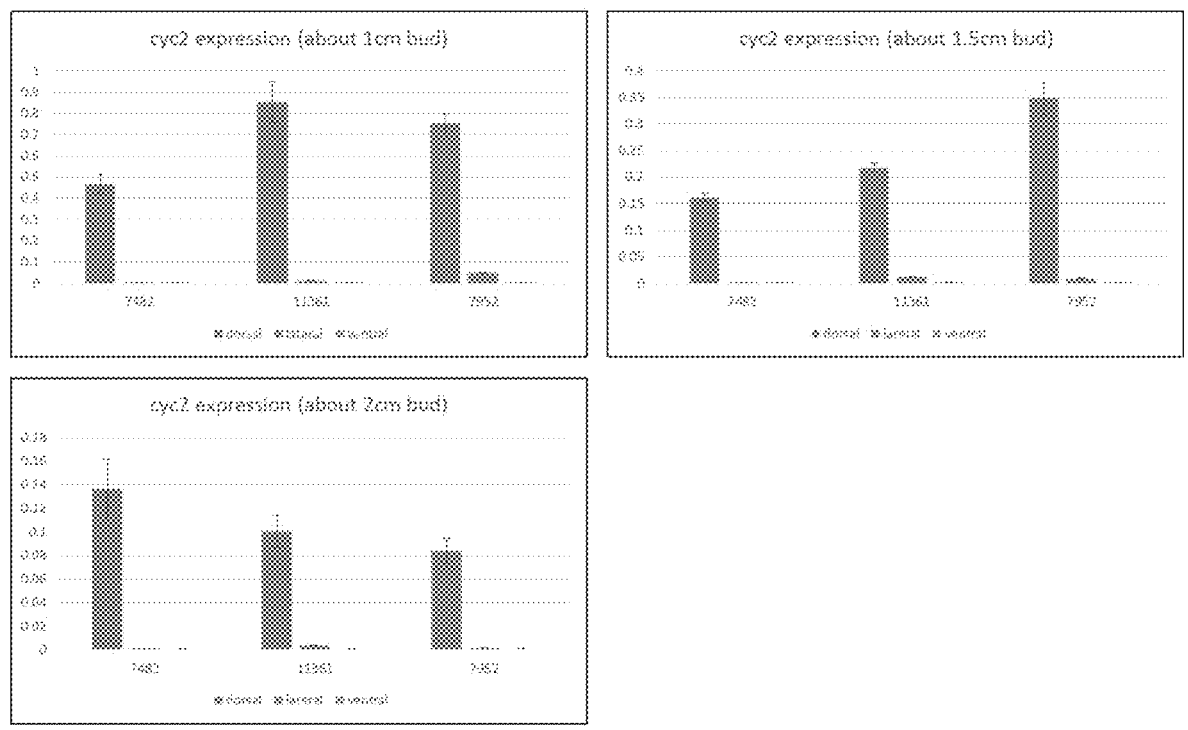
FIG. 9 shows the CYC2 expression pattern in the petals of accessions 7482, 7952, and 11361.

FIG. 7 shows the base sequence for the three Scaevola aemula accessions 7482, 7952 and 11361. All obtained sequences from 11361 possess a C to A point mutation, producing a stop codon (TAA) and truncated, presumably non-functional protein (FIGS. 7 and 8). Two of six obtained sequences from 7952 have the same C to A mutation, showing 7952 is a heterozygous mutant.

Figure 16:
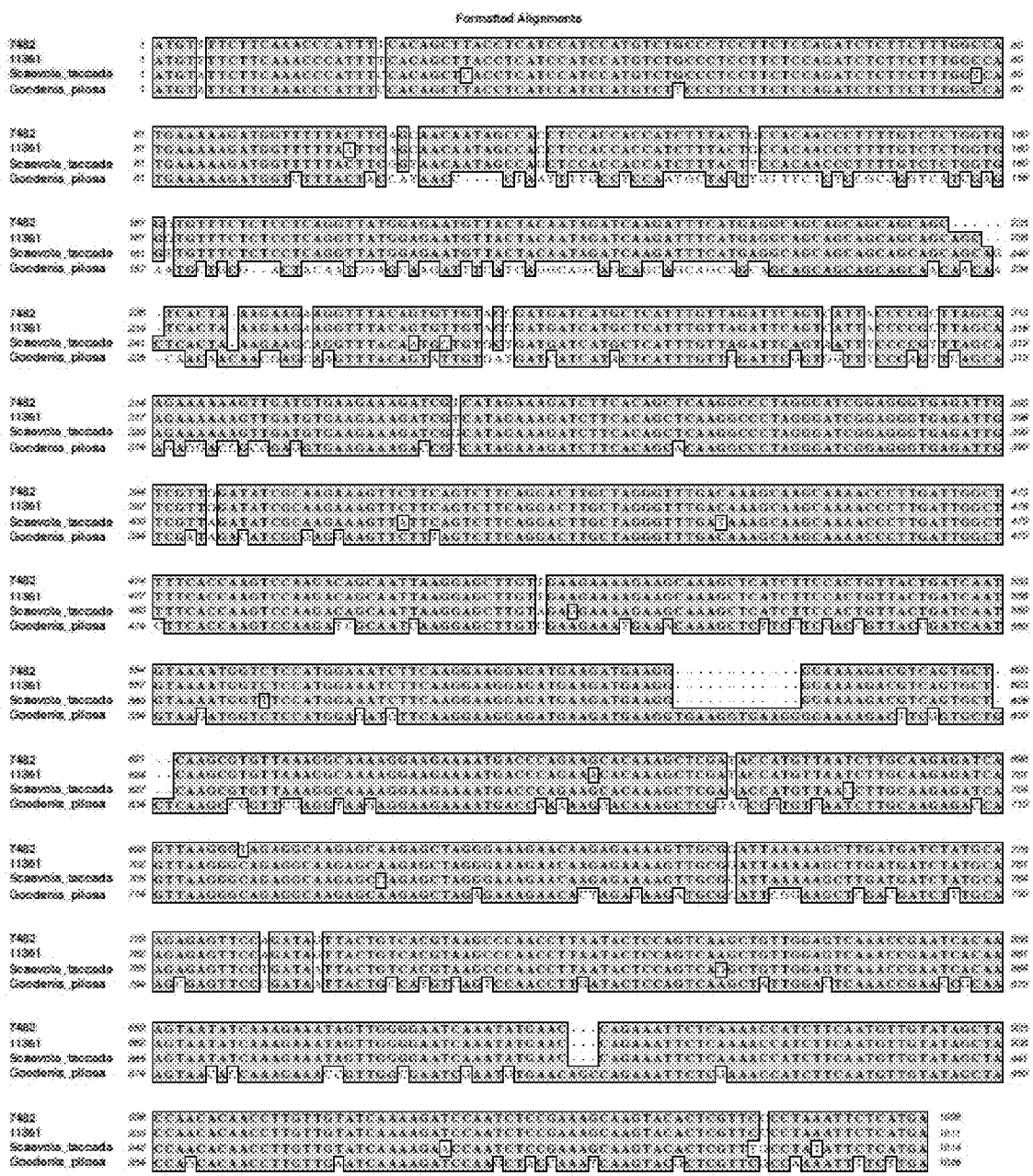
FIG. 16 shows an alignment of the sequences of the coding sequence of wild-type *Scaevola* aemula, CYCLOIDEA2—"7482" (SEQ ID NO:23), the coding sequence of *Scaevola aemula* CYCLOIDEA2—FUSED ALLELE—"11361" (SEQ ID NO:24), the coding sequence of wild-type *Scaevola taccada* CYCLOIDEA2 "*Scaevola_taccada*" (SEQ ID NO:25) and the coding sequence of the wild-type *Goodenia pilosa*, Cycloidea-like gene "*Goodenia_pilosa*" (SEQ ID NO:26). The adenine (A) at nucleotide position 99 in "11361" (SEQ ID NO:24), which is characteristic of the FUSED allele, is highlighted with a white box. In the other three wild-type sequences, there is a cytosine (C) at the equivalent position.

A further alignment of the sequences of: the coding sequence of wild-type Scaevola aemula, CYCLOIDEA2—"7482" (SEQ ID NO:23), the coding sequence of Scaevola aemula CYCLOIDEA2—FUSED ALLELE—"1361" (SEQ ID NO:24), the coding sequence of wild-type Scaevola taccada CYCLOIDEA2 "Scaevola_taccada" (SEQ ID NO:25) and the coding sequence of the wild-type Goodenia pilosa, Cycloidea-like gene "Goodenia_pilosa" (SEQ ID NO:26), is shown in in FIG. 16. The adenine (A) at nucleotide position 99 in "11361" (SEQ ID NO:24), which is characteristic of the FUSED allele, is highlighted with a white box. In the other three wild-type sequences, there is a cytosine (C) at the equivalent position.

Figure 10:
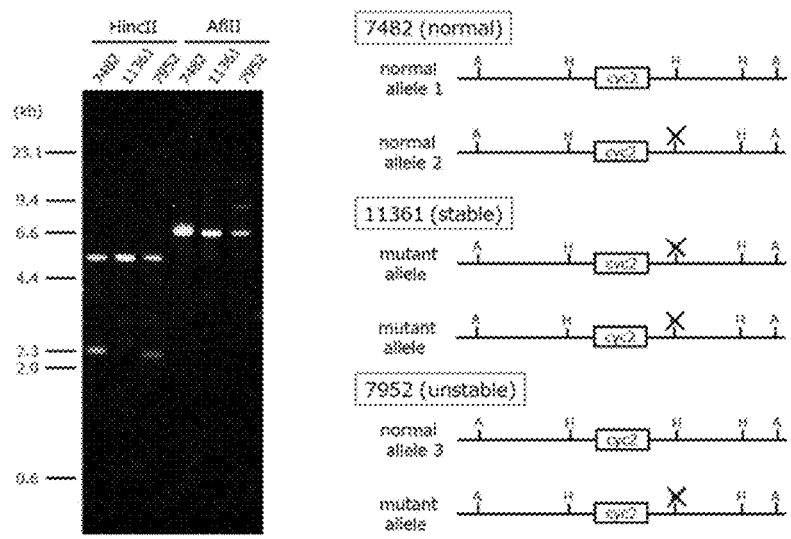
FIG. 10 shows Southern blot to determine the copy number of CYC2 in *Scaevola aemula* accessions used in the genetic investigations.

Quantitative RT-PCR was undertaken to determine the expression levels of CYC2 in the petals of Scaevola aemula flowers. Total RNA of dorsal, lateral, and ventral petals of 1 cm, 1.5 cm, and 2 cm flower buds was separately extracted using the RNeasy plant mini kit (Qiagen). cDNA was produced from total RNA using ReverTra Ace reverse transcriptase (Toyobo). Quantitative PCR was carried out using PowerUp SYBR Green Master Mix (Applied Biosystems) and StepOnePlus real-time PCR system (Applied Biosystems). Primers for CYC2 qPCR are CYC2rt-F (GGCAAGAGCAAGAGCTAGGG)—SEQ ID NO: 29 and CYC2rt-R (AGGTTGGGCTTACGTGACAG)—SEQ ID NO: 30. CYC2 expression levels were normalized to actin expression levels. Primers for actin qPCR are actrt-F (GCCTGATGGGCAGGTAATCA)—SEQ ID NO: 31 and actrt-R (TACCAGCAGCTTCCATTCCG)—SEQ ID NO: 32. Results are displayed in FIG. 10.

Accessions 7482, 7952, and 11361 showed essentially the same CYC2 expression pattern. Southern blot analysis was undertaken to determine the copy number of CYC2 in the Scaevola aemula accessions 7482, 7952 and 11361. Genomic DNA was extracted from leaf tissue using Nucleo-Spin PlantII Kit (Macherey-Nagel). About 15 μg of genomic DNA was digested with AflII or HincII (New England Biolabs), electrophoresed in a 0.8% agarose gel and transferred to a positively charged nylon membrane (GE Healthcare). A part of CYC2 cDNA sequence excluding regions conserved among all Cycloidea genes was labelled with digoxigenin using DIG-High Prime (Roche). Hybridization and detection were carried out according to the manufacturer's manual.

Southern blot analysis with AflII showed 1 band on all three varieties. Southern blot analysis with HincII showed 1 band on 11361, but 2 bands on 7482 and 7952. We hypothesized that 7482 had two normal alleles of the same CYC2 gene, one of which had an additional HincII site close to CYC2 gene, 7952 had one mutant allele and one normal alelle which had an additional HincII site, and that 11361 had two mutant alleles. These results suggested Scaevola aemula might have only one copy of CYC2 gene, agreeing with the results of Han 2018.

Example 7. Development of CAPS Marker System to Identify Heterozygous and Homozygous CYC2 Mutants DNA extraction was performed using NucleoSpin Plant II (MACHEREY-NAGEL). The following PCR primers and conditions were used to generate a 151 bp fragment, followed by MseI digestion and electrophoresis to distinguish normal, radially symmetrical (homozygous) and initially radially symmetrical, later normal flowering (heterozygous) plants. PCR primers for CAPS marker system are CYC2-2F (CCATGTCTGCCCTCCTTCT)—SEQ ID NO: 33 and CYC2-152R (AACATTCTCCATAACCTGAGGA)—SEQ ID NO: 34. PCRs were carried out using Tks gflex DNA polymerase (Takara Bio) for 30 cycles of 15 seconds at 98° C., 20 seconds at 60° C., and 30 seconds at 68° C.

Figure 11:
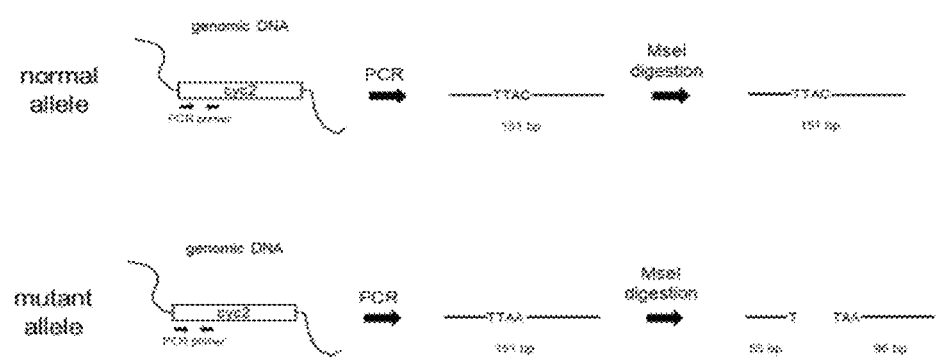
FIG. 11 shows a diagrammatic representation of CAPS marker system for identification of the mutant allele.
Figure 12:
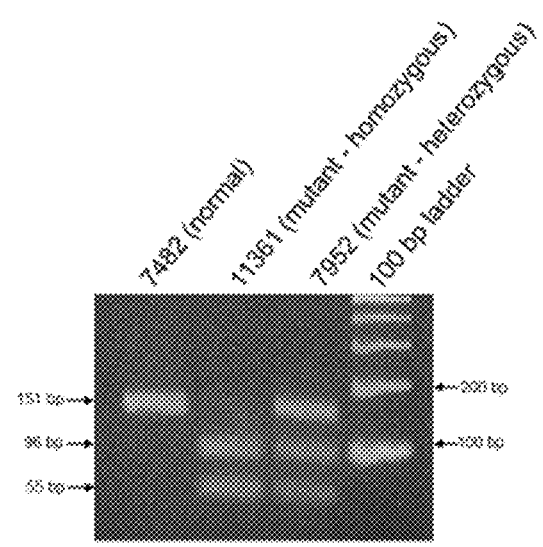
FIG. 12 shows CAPS marker result for accessions 7482 (normal), 7952 (heterozygous for FUSED allele) and 11361 (homozygous for FUSED allele).
Figure 13:
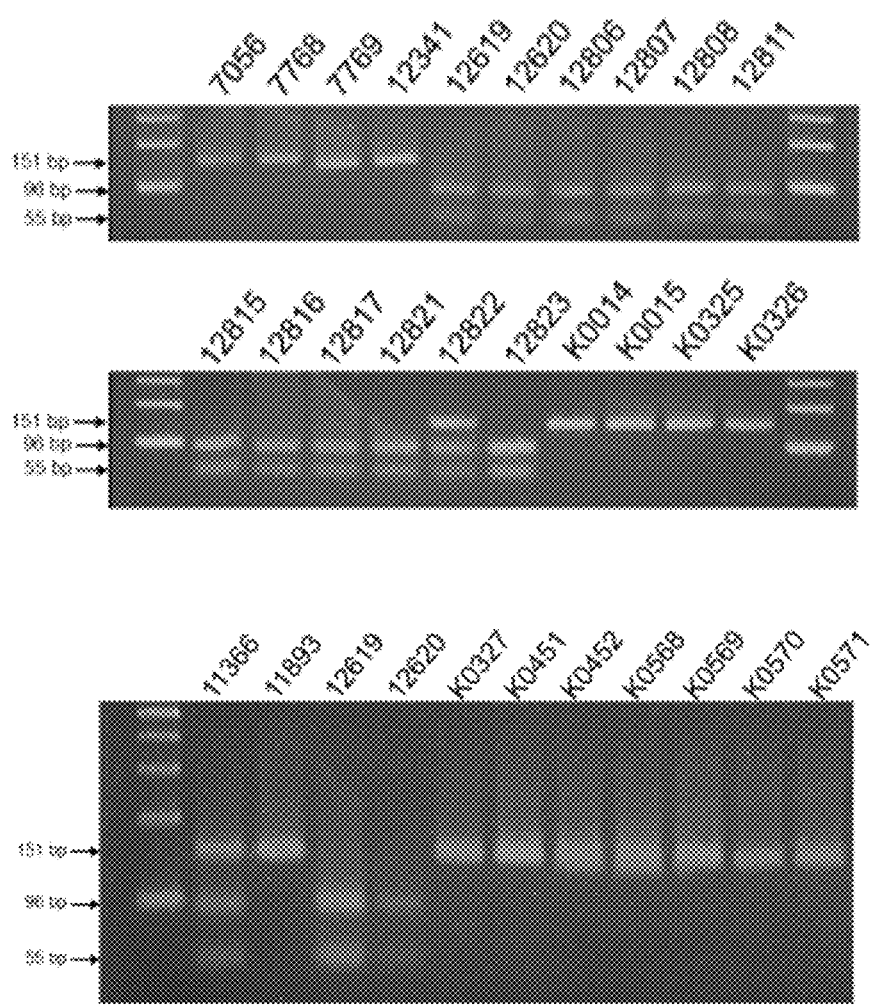
FIG. 13 shows electrophoresis gel images of CAPS marker analysis relating to Table 3.

FIG. 11 shows the diagrammatic representation of the CAPS marker system and FIG. 12 shows the CAPS marker results for the three accessions 7482, 7952 and 11361.

Example 8. Applying the CAPS Marker System to Commercially Available and Proprietary Accessions The CAPS marker system developed was utilized to assess 20 Scaevola aemula varieties and 19 Scaevola aemula accessions. Results are displayed in Table 3 and FIG. 14.

TABLE 3

List of thirty-nine Scaevola aemula commercially available varieties and proprietary accessions, including United States Plant Patent number, supplier, flower phenotype and results of CAPS marker testing

| Accession | Variety Name | United States Plant Patent | Supplier | Flower phenotype | CAP genotype |
|---|---|---|---|---|---|
| 7056 | Surdiva Light Blue | PP28,786 | Suntory Flowers | Normal | Normal/Normal |
| 7482 | Surdiva White Improved | PP26,471 | Suntory Flowers | Normal | Normal/Normal |
| 7768 | Surdiva Blue Violet | PP28,820 | Suntory Flowers | Normal | Normal/Normal |
| 7769 | Surdiva Fashion Pink | PP28,821 | Suntory Flowers | Normal | Normal/Normal |
| K0012 | New Wonder | PP10,584 | InnovaPlant | Normal | Normal/Normal |
| K0014 | Whirlwind White | PP20,790 | Proven Winners | Normal | Normal/Normal |
| K0015 | Bombay Pink | PP17,943 | Syngenta | Normal | Normal/Normal |
| K0054 | Top Pot White | PP19,728 | Westhoff | Normal | Normal/Normal |
| K0241 | Top Pot Blue | PP19,658 | Westhoff | Normal | Normal/Normal |
| K0242 | Scalora Topaz Pink | PP19,729 | Westhoff | Normal | Normal/Normal |
| K0325 | Scalora Suntastic Yellow | PP22,344 | Westhoff | Normal | Normal/Normal |
| K0326 | Pink charm | Not Patented | Danziger | Normal | Normal/Normal |
| K0327 | Blue angel | Not Patented | Danziger | Normal | Normal/Normal |
| K0451 | Scalora Brilliant | PP12,099 | Westhoff | Normal | Normal/Normal |
| K0452 | Scalora Diamond | PP15,431 | Westhoff | Normal | Normal/Normal |
| K0518 | Scalora Glitzy | Not Patented | Westhoff | Normal | Normal/Normal |
| K0568 | Touch White | Not Patented | Danziger | Normal | Normal/Normal |
| K0569 | Touch Blue | Not Patented | Danziger | Normal | Normal/Normal |
| K0570 | Touch Blessing Pink | Not Patented | Danziger | Normal | Normal/Normal |
| K0571 | Purple Haze | Not Patented | Danziger | Normal | Normal/Normal |
| 7952 | Proprietary accession | Not Patented | Bonza Botanicals | Initially radially symmetrical, then normal | Normal/Mutant |
| 11361 | Proprietary accession | Not Patented | Bonza Botanicals | Radially symmetrical | Mutant/Mutant |
| 11366 | Proprietary accession | Not Patented | Bonza Botanicals | Initially radially symmetrical, then normal | Normal/Mutant |
| 11380 | Proprietary accession | Not Patented | Bonza Botanicals | Normal | Normal/Normal |
| 11383 | Proprietary accession | Not Patented | Bonza Botanicals | Normal | Normal/Normal |
| 11893 | Proprietary accession | Not Patented | Bonza Botanicals | Normal | Normal/Normal |
| 12341 | Proprietary accession | Not Patented | Bonza Botanicals | Normal | Normal/Normal |
| 12619 | Proprietary accession | Not Patented | Bonza Botanicals | Radially symmetrical | Mutant/Mutant |
| 12620 | Proprietary accession | Not Patented | Bonza Botanicals | Radially symmetrical | Mutant/Mutant |
| 12806 | Proprietary accession | Not Patented | Bonza Botanicals | Radially symmetrical | Mutant/Mutant |
| 12807 | Proprietary accession | Not Patented | Bonza Botanicals | Radially symmetrical | Mutant/Mutant |
| 12808 | Proprietary accession | Not Patented | Bonza Botanicals | Radially symmetrical | Mutant/Mutant |
| 12811 | Proprietary accession | Not Patented | Bonza Botanicals | Radially symmetrical | Mutant/Mutant |
| 12815 | Proprietary accession | Not Patented | Bonza Botanicals | Radially symmetrical | Mutant/Mutant |
| 12816 | Proprietary accession | Not Patented | Bonza Botanicals | Radially symmetrical | Mutant/Mutant |
| 12817 | Proprietary accession | Not Patented | Bonza Botanicals | Radially symmetrical | Mutant/Mutant |
| 12821 | Proprietary accession | Not Patented | Bonza Botanicals | Radially symmetrical | Mutant/Mutant |

TABLE 3-continued

List of thirty-nine *Scaevola aemula* commercially available varieties and proprietary accessions, including United States Plant Patent number, supplier, flower phenotype and results of CAPS marker testing

| Accession | Variety Name | United States Plant Patent | Supplier | Flower phenotype | CAP genotype |
|---|---|---|---|---|---|
| 12822 | Proprietary accession | Not Patented | Bonza Botanicals | Initially radially symmetrical, then normal | Normal/Mutant |
| 12823 | Proprietary accession | Not Patented | Bonza Botanicals | Radially symmetrical | Mutant/Mutant |

Example 9. Transferring the FUSED Mutant Allele to a Wide Range of *Scaevola Aemula* Genetic Backgrounds Via Cross Pollination The homozygous FUSED mutant accession 11361 exhibiting floral radial symmetry was crossed as both a male and female parent, with a plurality of different *Scaevola aemula* accessions (genotype Normal/Normal=NN, Mutant/Normal=MN or Mutant/Mutant=MM). The resulting $F_1$ progeny were assessed phenotypically for the presence of the mutant FUSED allele and numerous plants were tested using the CAPS molecular marker system to identify heterozygotes.

Example 10. Inter-Crossing FUSED Heterozygotes to Determine the Segregation Ratio of the FUSED Trait Six accessions were selected based on the ability to produce at least one radially symmetrical flower during the early stages of flowering. This phenotypic characteristic has been shown to correlate with a heterozygous genotype for the mutant FUSED allele. The 6 accessions were randomly intercrossed by hand pollination using bulk pollen collected from all 6 accessions. Seeds were collected and germinated, resulting in 133 plants grown to flowering maturity. The resulting segregation was as expected with 25% radially symmetrical flowering mature plants and 75% normal phenotype plants recorded.

TABLE 4

Transmission of the mutant FUSED allele from accession 11361 homozygous for the radially symmetrical flower trait, to other *Scaevola aemula* accessions

| Cross Number | Female parent | Female genotype | Male parent | Male genotype | Number of plants developed | Phenotype of all mature plants | Plants tested by CAPS | Genotype of all plants tested by CAPS |
|---|---|---|---|---|---|---|---|---|
| M5-42 | 11361 | M/M | Whirlwind White | N/N | 39 | Normal | 4 | N/M |
| M5-29 | Whirlwind White | N/N | 11361 | M/M | 3 | Normal | | |
| M5-43 | 11361 | M/M | Kangaroo Island | N/N | 6 | Normal | 6 | N/M |
| M5-30 | Kangaroo Island | N/N | 11361 | M/M | 14 | Normal | 2 | N/M |
| M5-44 | 11361 | M/M | Scarletti | N/N | 3 | Normal | | |
| M5-31 | Scarletti | N/N | 11361 | M/M | 3 | Normal | 1 | N/M |
| M5-45 | 11361 | M/M | 16-141 | N/N | 21 | Normal | 6 | N/M |
| M5-32 | 16-141 | N/N | 11361 | M/M | 1 | Normal | | |
| M5-47 | 11361 | M/M | 16-200 | N/N | 1 | Normal | | |
| M5-34 | 16-200 | N/N | 11361 | M/M | 4 | Normal | | |
| M5-48 | 11361 | M/M | 16-204 | N/N | 10 | Normal | 6 | N/M |
| M5-35 | 16-204 | N/N | 11361 | M/M | 25 | Normal | 4 | N/M |
| M5-49 | 11361 | M/M | 16-214 | N/N | 16 | Normal | 5 | N/M |
| M5-36 | 16-214 | N/N | 11361 | M/M | 83 | Normal | 5 | N/M |
| M5-50 | 11361 | M/M | 16-221 | N/N | 11 | Normal | 6 | N/M |
| M5-37 | 16-221 | N/N | 11361 | M/M | 11 | Normal | 4 | N/M |
| M5-51 | 11361 | M/M | 16-226 | N/N | 1 | Normal | | |
| M5-52 | 11361 | M/M | 18-151 | M/M | 10 | Mutant | | |
| M5-39 | 18-151 | M/M | 11361 | M/M | 22 | Mutant | | |
| M5-54 | 11361 | M/M | 18-157 | N/N | 2 | Normal | | |
| M5-33 | 16-185 | M/N | 11361 | M/M | 10 | 10 Normal 4 Mutant | | |
| M5-40 | 18-152 | M/M | 11361 | M/M | 1 | Mutant | | |

TABLE 5

Segregation results of radially symmetrical to normal phenotype plants from intercrossing six accessions heterozygous for the FUSED mutant allele

| Female Parent | Genotype | | Male Parent | Genotype | Expected phenotype | | Observed phenotype | |
|---|---|---|---|---|---|---|---|---|
| | | | | | Normal | Fused | Normal | Fused |
| 16-144 | NM | x | All | NM | 24.75 | 8.25 | 27 | 6 |
| 16-182 | NM | x | All | NM | 21.75 | 7.25 | 21 | 8 |
| 16-184 | NM | x | All | NM | 24.75 | 8.25 | 20 | 13 |
| 16-185 | NM | x | All | NM | 12 | 4 | 13 | 3 |
| 16-203 | NM | x | All | NM | 3.75 | 1.25 | 4 | 1 |
| 17-27 | NM | x | All | NM | 30 | 10 | 30 | 10 |
| Total | | | | | 117 | 39 | 115 | 41 |
| Ratio | | | | | 3 | 1 | 2.8 | 1 |

The observed ratio of Normal to FUSED mutant plants was 2.8:1, the expected ratio was predicted to be 3:1. According to this data it can be considered that the FUSED allele is a single recessive gene, in agreement with the molecular data presented previously.

SUMMARY OF SEQUENCES

| SEQ ID NO: | Sequence type | Order/genus/species | Name | Abbreviation |
|---|---|---|---|---|
| 1 | Protein | *Scaevola aemula* | CYCLOIDEA2 wild-type | SamCYC2 |
| 2 | Protein | *Scaevola taccada* | CYCLOIDEA2 wild-type | StaCYC2 |
| 3 | Protein | *Scaevola sericea* | CYCLOIDEA2 wild-type | SseCYC2 |
| 4 | DNA-gene | *Scaevola aemula* | CYCLOIDEA2 wild-type | SamCYC2 |
| 5 | DNA-cDNA | *Scaevola aemula* | CYCLOIDEA2 wild-type | SamCYC2 |
| 6 | DNA-cDNA | *Scaevola taccada* | CYCLOIDEA2 wild-type | SamCYC2 |
| 7 | DNA-gene | *Scaevola aemula* | CYCLOIDEA2 Fused allele | SamCYC2 |
| 8 | DNA-cDNA | *Scaevola aemula* | | Fused allele SamCYC2 |
| 9 | Protein | *Asterales* | CYCLOIDEA2 | Motif 1 from Chen et al 2018 with variable amino acids shown as Xs |
| 10 | Protein | *Scaevola* | CYCLOIDEA2 | CYC2 Motif 1 (corresponding to Motif 1 from Chen et al 2018) with variable amino acids shown as Xs |
| 11 | Protein | *Scaevola* | CYCLOIDEA2 | CYC2 Motif 1 (corresponding to Motif 1 from Chen et al 2018) with options for the variable amino acids shown as Xs |
| 12 | Protein | *Scaevola aemula* | CYCLOIDEA2 | CYC2 Motif 1 (corresponding to Motif 1 from Chen et al 2018) |
| 13 | Protein | *Scaevola taccada* | CYCLOIDEA2 | CYC2 Motif 1 (corresponding to Motif 1 from Chen et al 2018) |
| 14 | Protein | *Scaevola sericea* | CYCLOIDEA2 | CYC2 Motif 1 (corresponding to Motif 1 from Chen et al 2018) |

SUMMARY OF SEQUENCES

| SEQ ID NO: | Sequence type | Order/genus/species | Name | Abbreviation |
|---|---|---|---|---|
| 15 | Protein | *Scaevola* | CYCLOIDEA2 | CYC2 Motif 2 (corresponding to Motif 1 from Chen et al 2018) with variable amino acids shown as Xs |
| 16 | Protein | *Scaevola* | CYCLOIDEA2 | CYC2 Motif 2 (corresponding to Motif 1 from Chen et al 2018) with options for the variable amino acids shown as Xs |
| 17 | Protein | *Scaevola aemula* | CYCLOIDEA2 | CYC2 Motif 2 (corresponding to Motif 1 from Chen et al 2018) |
| 18 | Protein | *Scaevola taccada* | CYCLOIDEA2 | CYC2 Motif 2 (corresponding to Motif 1 from Chen et al 2018) |
| 19 | Protein | *Scaevola sericea* | CYCLOIDEA2 | CYC2 Motif 2 (corresponding to Motif 1 from Chen et al 2018) |
| 20 | Protein | *Scaevola* | CYCLOIDEA2 | CYC2 Motif 4 (corresponding to Motif 1 from Chen et al 2018) |
| 21 | Protein | *Scaevola taccada* | CYCLOIDEA2 | CYC2 Motif 4 (corresponding to Motif 1 from Chen et al 2018) |
| 22 | Protein | *Scaevola sericea* | CYCLOIDEA2 | CYC2 Motif 4 (corresponding to Motif 1 from Chen et al 2018) |
| 23 | DNA | *Scaevola aemula* | CYCLOIDEA2 | Coding sequence-wild-type-7482 |
| 24 | DNA | *Scaevola aemula* | CYCLOIDEA2 | Coding sequence-FUSED ALLELE-11361 |
| 25 | DNA | *Scaevola taccada* | CYCLOIDEA2 | Coding sequence |
| 26 | DNA | *Goodenia pilosa* | Cycloidea-like | Coding sequence from GenBank: MG593373.1 |
| 27 | DNA | Artificial | Primer | St-cycF1 |
| 28 | DNA | Artificial | Primer | St-cycR1 |
| 29 | DNA | Artificial | Primer | CYC2rt-F |
| 30 | DNA | Artificial | Primer | CYC2rt-R |
| 31 | DNA | Artificial | Primer | actrt-F |
| 32 | DNA | Artificial | Primer | actrt-R |
| 33 | DNA | Artificial | Primer | CYC2-2F |
| 34 | DNA | Artificial | Primer | CYC2-152R |

The invention claimed is:

1. A *Scaevola aemula* plant that comprises a mutant CYC2 allele characterized by eliminated CYC2 gene expression and/or reduced or eliminated CYC2 protein activity, wherein the plant produces at least one flower with a floral phenotype characterized by a radially symmetrical arrangement of petals as a result of the plant containing the mutant CYC2 allele.

2. The plant of claim 1 wherein the floral phenotype is further characterised by at least one of:
   a) a fused dorsal slit, and
   b) delayed senescence.

3. The plant of claim 1 wherein the allele is present in the heterozygous state, and the plant expresses the floral phenotype in the first few flowers that develop on the plant, and later flowers are of wild-type appearance.

4. The plant of claim 1 wherein the allele is present in the homozygous state, and the plant expresses the floral phenotype in all, or nearly all, flowers produced.

5. The plant of claim 1 wherein the mutant CYC2 allele is characterised by at least one of:

a) the presence of an adenine (A) at position corresponding to nucleotide 39 in the sequence of SEQ ID NO: 7,
   b) the presence of an adenine (A) at position corresponding to nucleotide 39 in the sequence of SEQ ID NO: 8,
   c) the presence of an adenine (A) at position corresponding to nucleotide 99 in the sequence of SEQ ID NO: 24.

6. The plant of claim 5, wherein the adenine (A) is the result of a substitution from a cytosine (C) at the same position in the corresponding wild-type sequence.

7. The plant of claim 6 wherein:
   a) SEQ ID NO: 4 is the wild-type sequence corresponding to SEQ ID NO: 7,
   b) SEQ ID NO: 5 is the wild-type sequence corresponding to SEQ ID NO: 8, and
   c) SEQ ID NO: 23 is the wild-type sequence corresponding to SEQ ID NO: 24.

8. The plant of claim 1, wherein the plant, or the mutant CYC2 allele, comprises the sequence of any one of:
   a) SEQ ID NO: 7,
   b) SEQ ID NO: 8, and
   c) SEQ ID NO: 24.

9. The plant of claim 1 produced, or derived, from a seed deposited under Accession Number: NCIMB 43619.

10. A plant cell, plant part, propagule, seed, cutting, cell culture, tissue culture, or callus of, or capable of producing, the plant of claim 1.

11. The plant cell, plant part, propagule, seed, cutting, cell culture, tissue culture, or callus of claim 10, wherein:
   a) the plant cell, plant part, propagule, seed, cutting, cell culture, or callus is produced from a seed deposited under Accession Number: NCIMB 43619, and/or
   b) the seed is as deposited under Accession Number: NCIMB 43619.

12. A method of producing a *Scaevola aemula* plant that produces at least one flower with a floral phenotype characterised by a radially symmetrical arrangement of petals, wherein the method includes at least one of:
   a) genetically manipulating a *S. aemula* plant to produce a mutant CYC2 allele characterized by eliminated CYC2 gene expression and/or reduced or eliminated CYC2 protein activity in the plant,
   b) gene-editing a *S. aemula* plant to produce the mutant CYC2 allele in the *S. aemula* plant,
   c) inducing a mutation that produces the mutant CYC2 allele in the *S. aemula* plant,
   d) crossing the *S. aemula* plant of claim 1 with another *S. aemula* plant,
   e) selfing the *S. aemula* plant of claim 1,
   f) introducing the mutant CYC2 allele into a *S. aemula* plant, and
   g) vegetatively propagating the *S. aemula* plant of claim 1.

13. The method of claim 12 that includes the step of testing the plant produced for the presence of the mutant CYC2 allele.

14. A plant produced by the method of claim 13.

15. A method of producing seed, the method comprising growing a plant of claim 1 and harvesting the seed produced by the plant grown.

16. A method for identifying a *Scaevola aemula* plant with a genotype indicative of producing at least one flower with a floral phenotype characterised by a radially symmetrical arrangement of petals, the method comprising testing a *S. aemula* plant for:
   presence of a mutant CYC2 allele characterized by eliminated CYC2 gene expression and/or reduced or eliminated CYC2 protein activity,
   wherein presence of the mutant CYC2 allele indicates that the *S. aemula* plant will produce at least one flower with the floral phenotype.

* * * * *